United States Patent [19]

Omata

[11] Patent Number: 5,766,137
[45] Date of Patent: Jun. 16, 1998

[54] FREQUENCY DEVIATION DETECTING CIRCUIT AND MEASURING APPARATUS USING THE FREQUENCY DEVIATION DETECTING CIRCUIT

[75] Inventor: Sadao Omata, Koriyama, Japan

[73] Assignee: Axiom Co., Ltd., Koriyama, Japan

[21] Appl. No.: 713,268

[22] Filed: Sep. 12, 1996

[30] Foreign Application Priority Data

Sep. 20, 1995 [JP] Japan .............................. HEI 7-241869
Sep. 3, 1996 [JP] Japan .................................. 8-233406

[51] Int. Cl.$^6$ .............................. A61B 5/103; G01N 3/38
[52] U.S. Cl. .............................. 600/587; 73/573; 73/579
[58] Field of Search .............................. 73/54.25, 54.24,
73/573, 488, 514.29, 579, 78, 702; 128/637,
649, 737, 739, 740, 774, 552–553

[56] References Cited

U.S. PATENT DOCUMENTS

| | | | |
|---|---|---|---|
| 3,958,450 | 5/1976 | Kleesattel | 73/67.2 |
| 4,026,671 | 5/1977 | Simons et al. | 23/259 |
| 4,297,884 | 11/1981 | Leveque et al. | 128/774 X |
| 4,646,754 | 3/1987 | Seale | 128/649 X |
| 4,682,608 | 7/1987 | De Rigal et al. | 128/774 |
| 4,783,987 | 11/1988 | Hager et al. | 73/32 A |
| 5,251,627 | 10/1993 | Morris | 128/645 |
| 5,421,829 | 6/1995 | Olichney | 606/170 |
| 5,591,900 | 1/1997 | Bronowocki et al. | 73/52 |

FOREIGN PATENT DOCUMENTS

B-40-27236 11/1940 Japan .
A-1-189583 7/1989 Japan .
A-2-290529 11/1990 Japan .

OTHER PUBLICATIONS

Journal of the Society of Instrument and Control Engineers, vol. 14, No. 3 (1975), O. Takatani et al., pp. 281–292.

Technical Digest of the 9th Sensor Symposium, "New Type Tactile Sensor for Sensing Hardness Like the Human Hand and Its Applications for Living Tissue", S. Omata, pp. 257–260.

Journal of the Japan Society of Medical Electronics and Biological Engineering, vol. 28, No. 1 (1990), "Measurements of the Hardness of a Soft Material with a Piezoelectric Vibrometer and Their Analysis", Iyodenshi to Seitaokogaku, S. Omata, pp. 1–4.

Journal of the Japan Society of Medical Electronics and Biological Engineering, vol. 24, Bo. 5 (1986), "Development of Piezoelectric Transducer for Measuring Contact Compliance of a Soft Body", Iyodenshi to Seitaikogaku, S. Omata, pp. 38–42.

*Primary Examiner*—Francis Jaworski
*Attorney, Agent, or Firm*—Oliff & Berridge, PLC

[57] ABSTRACT

A hardness measuring apparatus in which a frequency deviation detecting circuit is used has a contact element, an oscillator, a self-oscillating circuit and a gain variation compensating circuit. The self-oscillating circuit feeds back oscillation information of the oscillator to generate a resonant state. The gain variation compensating circuit is disposed in the self-oscillating circuit. The gain variation compensating circuit has a central frequency different from that of the self-oscillating circuit, and increases gain in response to a change in frequency.

26 Claims, 28 Drawing Sheets

FREQUENCY DEVIATION DETECTING CIRCUIT AND MEASURING APPARATUS USING THE FREQUENCY DEVIATION DETECTING CIRCUIT

BACKGROUND OF THE INVENTION

1. Field of the Invention

The present invention relates to a frequency deviation detecting circuit and a measuring apparatus using the frequency deviation detecting circuit, particularly to a hardness measuring apparatus, which is equipped with a contact element which is suitable for a hardness measuring apparatus, oscillated by an oscillator and brought into contact with a measuring subject in order to measure the hardness of the subject. A hardness measuring apparatus provided by the present invention has advantages in measuring the hardness of soft subjects, such as rubber, resin, food, and that of biological tissue subjects, such as human skin and internal organs, whose hardness has not been accurately determined. In addition, the present invention is applicable to an acceleration measuring apparatus, fluid pressure measuring apparatus or fluid viscosity measuring apparatus in which a frequency deviation detecting circuit is used.

2. Description of the Related Art

Many measuring apparatuses which detect a change in the frequency of an applied signal to determine a property of a subject have been known. For example, Japanese Patent Publication No. Sho 40-27236, Japanese Patent Laid-Open Publication No. Hei 1-189583 and Japanese Patent Laid-Open Publication No. Hei 2-290529 disclose hardness measuring apparatuses which determine the hardness of a subject using frequency deviation. The hardness measuring apparatuses disclosed in these publications have an ultrasonically oscillating probe which is brought into contact with a subject (sample to be subjected to measurement), and determine the hardness of the subject by detecting a change in the resonance frequency or oscillation amplitude of the probe. In such a hardness measuring apparatus, a self-oscillating circuit in which an oscillation system including a subject contacting oscillator in contact with the subject forms a feedback loop causes resonance. When the subject contacting oscillator or a contact element mechanically coupled with the subject contacting oscillator comes into contact with a subject in a resonant state, the impedance of the subject brings about changes in the oscillating frequency and detection voltage of the self-oscillating circuit. These changes give information about the hardness of the subject. This kind of hardness measuring apparatus has the following advantages:

(1) The hardness of a subject can be quantitatively measured.
(2) The hardness of a subject can be electrically measured, requiring a short measuring time.
(3) The hardness of a subject can be non-destructively measured without any damage to a subject.

A hardness measuring apparatus having these advantages is promising for determining the elasticity (hardness) of human tissue, such as skin and internal organs, and that of biological tissues of animals and plants, and for being used as a tactile sensor of an industrial robot.

A circuit having a feedback loop is formed by a self-oscillating circuit or the like.

When an oscillator oscillating in a resonant state due to the circuit comes into contact with a subject, a mechanical impedance is added, leading to changes in the resonance frequency and detection voltage of the oscillator. This phenomenon is already known and described by T. Akatsuka and O. Takatani in *Journal of the Society of Instrument and Control Engineers*, Vol. 14, No. 3, pp. 281-292 (1975). According to the general frequency-gain (current amplification factor) characteristic of a self-oscillating circuit including an oscillator, the gain increases with the increase in frequency, has a peak at a resonance frequency (central frequency), and decreases with further increase in frequency. When a contact probe coupled with such an oscillating circuit is applied to a soft and elastic subject, such as biological tissues of human skin or internal organs, with a certain area, both the resonance frequency and gain decrease, as shown by S. Omata in "Technical Digest of the 9th Sensor Symposium" pp. 257-260 (1990). In particular, the hardness of a biological tissue is changed when a pathological lesion exists in the tissue. The presence of the pathological lesion can be easily detected by measuring the hardness of the tissue. Therefore, this method is expected to be applied in the field of medicine.

When the hardness of such a soft subject as a biological tissue is measured, however, neither a change in the resonant frequency nor that in the oscillation amplitude is detected as a sufficient detection voltage, due to a decreased gain. This prevents the hardness of such a biological tissue from being precisely measured. In particular, hardness information extracted by a subject contacting oscillator or contact element of a hardness measuring apparatus has a lot of noise, which is added to the detection voltage. Consequently, it is difficult to obtain accurate hardness information. In addition, the hardness is varied even among soft subjects, and the frequency characteristic and the variation in gain are different among the soft subjects. Therefore, it has been difficult to accurately obtain the hardness information of various subjects.

SUMMARY OF THE INVENTION

In order to solve the above problems, the present invention has the following objects:

(1) The first object of the present invention is to provide a frequency deviation detecting circuit which has a simple structure, is fabricated with low cost, and can accurately detect oscillation information of an oscillator in a wide frequency range.
(2) The second object of the present invention is to provide a hardness measuring apparatus which can obtain hardness information of soft and hard subjects in a wide hardness range.
(3) The third object of the present invention is to provide a hardness measuring apparatus which achieves the second object, has a simple structure, and is fabricated with low cost.
(4) The fourth object of the present invention is to provide a hardness measuring apparatus which achieves the third object, and whose size can be reduced.
(5) The fifth object of the present invention is to provide a hardness measuring apparatus by which the hardness of a biological tissue, particularly that of a human living tissue, can be easily and accurately measured, and a medical diagnosis can be easily performed for preventing a disease.
(6) The sixth object of the present invention is to provide various apparatuses equipped with the frequency deviation detecting circuit, such as an acceleration measuring apparatus, fluid pressure measuring apparatus and fluid viscosity measuring apparatus.

In order to solve the above problems, a frequency deviation detecting circuit provided by the invention comprises an oscillator for generating oscillation, a self-oscillating circuit for feeding back oscillation information of the oscillator to generate a resonant state, and a gain variation compensating circuit which is disposed in the self-oscillating circuit, has a central frequency different from that of the self-oscillating circuit, and increases gain in response to a change in frequency, wherein the oscillator and self-oscillating circuit form an electromechanical oscillation system, and the effective resonance frequency band of the electromechanical oscillation system is expanded. According to the invention, the gain variation compensation circuit increases the gain in response to a change in the resonance frequency of the electromechanical system. Since the detection voltage as the oscillation information of the oscillator can be increased by an increase in the gain, the oscillation information can be accurately detected. In addition, since the gain can be increased in response to a change in the resonance frequency of the oscillator, the oscillation information of the oscillator can be accurately detected in a wide frequency range.

The invention provides a frequency deviation detecting circuit, wherein the gain variation compensating circuit has a phase transfer function for adjusting the difference between the input and output phases, called phase difference, of the self-oscillating circuit to zero, and of promoting feedback oscillation, shifts the frequency so that the phase difference becomes zero, and increases the gain. In the invention, the gain variation compensating circuit has the phase transfer function, can further change the central frequency by a frequency corresponding to the phase difference of the electromechanical oscillation system when the frequency of the electromechanical oscillation system is changed, and can increase the gain in response to the change in the central frequency. Therefore, the detection voltage of the oscillator as oscillation information is increased by the further increased gain. This enables the oscillation information to be precisely detected. Since the gain can be increased in response to a change in the resonant frequency of the oscillator, the oscillation information of the oscillator can be precisely detected in a wide frequency range.

A hardness measuring apparatus provided by the invention comprises a contact element coming into contact with a subject, an oscillator for oscillating the contact element, a self-oscillating circuit which feeds back oscillation information of the oscillator in contact with the subject to generate a resonant state, and a gain variation compensating circuit which is disposed in the self-oscillating circuit, has a central frequency different from that of the self-oscillating circuit, and increases gain in response to a change in frequency, wherein the contact element, oscillator and self-oscillating circuit form an electromechanical oscillation system, and the effective resonance frequency band of the electromechanical oscillation system is expanded. According to the invention, when the contact element is in contact with a subject, the resonance frequency of an electromechanical oscillation system is changed in response to a change in mechanical impedance representing the hardness of the subject. The gain variation compensating circuit increases the gain in response to the change in the resonance frequency. Since the detection voltage as hardness information of the subject can be increased by the increase in the gain, the hardness of the subject can be accurately measured. In addition, when various hardnesses of subjects are measured, the gain can be increased in response to changes in resonance frequency. This enables the measurement of hardness to be accurate in a wide hardness range.

The invention further provides a hardness measuring apparatus, wherein the hardness of a subject is measured using a change in the frequency of the electromechanical oscillation system.

The invention further provides a hardness measuring apparatus, wherein the hardness of a subject is measured using a change in the phase of the electromechanical oscillation system.

The invention further provides a hardness measuring apparatus, wherein the gain compensating circuit increases the gain with a decrease in frequency, and the effective resonance frequency band of the electromechanical oscillation system is expanded in a frequency range used for measuring the hardnesses of soft subjects.

The invention further provides a hardness measuring apparatus, wherein the oscillator is any one of a piezoelectric ceramic oscillator, a layered ceramic oscillator, a PVDF-based oscillator, a magnetostrictive element, a bimorph oscillator, a quartz oscillator or a surface acoustic wave (SAW) element.

The invention provides a hardness measuring apparatus, wherein the self-oscillating circuit has an amplifying circuit for amplifying the oscillation information of the oscillator.

The invention provides a hardness measuring apparatus, wherein the gain variation compensating circuit comprises any of a band-pass filter circuit, a low-pass filter circuit, a high-pass filter circuit, a notch filter circuit, an integrating circuit, a differentiating circuit, a peaking amplifying circuit, an active filter circuit or a passive filter circuit.

The invention further provides a hardness measuring apparatus, wherein the gain variation compensating circuit is disposed between an output terminal of the oscillator and an input terminal of the amplifying circuit of the self-oscillating circuit, or between an output terminal of the amplifying circuit of the self-oscillating circuit and an input terminal of the oscillator.

A hardness measuring apparatus provided by the invention further comprises a contact element becoming in contact with a subject, an oscillator for oscillating the contact element, a self-oscillating circuit which feeds back oscillation information of the oscillator in contact with the subject to generate a resonant state, a gain variation compensating circuit which is disposed in the self-oscillating circuit, has a central frequency different from that of the self-oscillating circuit, and increases gain in response to a change in frequency, an electromechanical oscillation system formed by the contact element, oscillator and self-oscillating circuit and a frequency measuring circuit for detecting a change in the frequency of the electromechanical oscillation system.

The invention further provides a hardness measuring apparatus, wherein the gain variation compensating circuit has a phase transfer function of adjusting the difference between the input and output phases, called phase difference, of the self-oscillating circuit to zero, and of promoting feedback oscillation, shifts the frequency so that the phase difference becomes zero, and increases the gain. In the invention, the gain variation compensating circuit has the phase transfer function, can further change the central frequency by a frequency corresponding to the phase difference of the electromechanical oscillation system when the frequency of the electromechanical oscillation system is changed, and can increase the gain in response to the change in the central frequency. Therefore, the detection voltage of the oscillator as oscillation information is increased by the further increased gain. This enables the oscillation information to be precisely detected. Since the gain can be increased in response to a change in the resonant frequency of the oscillator, the hardness of a soft subject or hard subject can be precisely determined in a wide range.

The invention also provides a hardness measuring apparatus, further comprising a detecting element for detecting the oscillation information of the oscillator, wherein the oscillator includes a layered piezoelectric ceramic oscillator formed by stacking a plurality of piezoelectric ceramic layers, and the detecting element comprises a film-shaped bimorph oscillator.

The invention provides a hardness measuring apparatus, further comprising a detecting element for detecting the oscillation information of the oscillator, wherein both the oscillator and detecting element comprise a layered piezoelectric ceramic oscillator formed by stacking a plurality of piezoelectric ceramic layers.

The invention provides a hardness measuring apparatus, further comprising a detecting element for detecting the oscillation information of the oscillator, wherein both the oscillator and detecting element comprise a film-shaped piezoelectric material.

A hardness measuring apparatus provided by the invention comprises a contact element becoming in contact with a subject, an oscillator for oscillating the contact element, a phase lock loop circuit which feeds back oscillation information of the oscillator in contact with the subject to generate a resonant state, and a gain variation compensating circuit which is disposed in the phase lock loop circuit, has a central frequency different from that of the phase lock loop circuit, and increases gain in response to a change in frequency, wherein the contact element, oscillator and phase lock loop circuit form an electromechanical oscillation system, and the effective resonance frequency band of the. electromechanical oscillation system is expanded.

The invention provides a hardness measuring apparatus, wherein the subject is a biological tissue, and the contact element is made to come into contact with the biological tissue when the hardness of the biological tissue is measured.

The invention provides a hardness measuring apparatus, wherein the biological tissue is any of skin, internal organs, body cavities, bones, teeth or nails, and its hardness is measured.

The invention also provides a hardness measuring apparatus, further comprising a main probe in which the oscillator is contained, and the contact element is fixed, and a monitor for displaying hardness information based on the oscillation information.

The invention also provides a hardness measuring apparatus, further comprising a fiberscope unit, wherein an observation image obtained by the fiberscope unit is displayed on the monitor.

The invention also provides a hardness measuring apparatus, further comprising a contact needle and outer needles for puncturing a biological tissue, wherein the contact needle is used as the contact element, and the outer needles are disposed around the contact needle to form the tip portion of the main probe.

The invention further provides a hardness measuring apparatus, wherein the tip portion of the main probe is formed by a soft tube.

An acceleration measuring apparatus for measuring a change in the acceleration of a moving substance, provided by the invention, further, comprises an oscillator which is placed on the moving substance to generate oscillation, a self-oscillating circuit which feeds back oscillation information of the oscillator to generate a resonant state, and a gain variation compensating circuit which is disposed in the self-oscillating circuit, has a central frequency different from that of the self-oscillating circuit, and increases gain in response to a change in frequency, wherein the oscillator and self-oscillating circuit form an electromechanical oscillation system, and consequently the effective resonance frequency band of the electromechanical oscillation system is expanded.

A fluid viscosity measuring apparatus for measuring a change in the viscosity of a fluid, provided by the invention, further any of an oscillator for generating oscillation in the fluid or an oscillator for oscillating a fluid contacting element put into the fluid, a self-oscillating circuit which feeds back oscillation information of the oscillator to generate a resonant state, and a gain variation compensating circuit which is disposed in the self-oscillating circuit, has a central frequency different from that of the self-oscillating circuit, and increases gain in response to a change in frequency, wherein the oscillator and self-oscillating circuit form an electromechanical oscillation system, and the effective resonance frequency band of the electromechanical oscillation system is expanded.

A fluid pressure measuring apparatus for measuring a change in the pressure of a fluid, provided by the invention, further comprises a fluid contacting element whose shape is changed in response to the pressure of the fluid, an oscillator which generates oscillation, and the position of which is moved in response to the change in the pressure of the fluid, a self-oscillating circuit which feeds back oscillation information of the oscillator to generate a resonant state, and a gain variation compensating circuit which is disposed in the self-oscillating circuit, has a central frequency different from that of the self-oscillating circuit, and increases gain in response to a change in frequency, wherein the oscillator and self-oscillating circuit form an electromechanical oscillation system, and the effective resonance frequency band of the electromechanical oscillation system is expanded.

The invention further provides a measuring apparatus, wherein the gain variation compensating circuit has a phase transfer function of adjusting the difference between the input and output phases, called phase difference, of the self-oscillating circuit to zero, and of promoting feedback oscillation, shifts the central frequency so that the phase difference becomes zero, and increases the gain.

DESCRIPTION OF THE PREFERRED EMBODIMENTS

Embodiment 1

[System Structure of a Hardness Measuring Apparatus]

Figure 1:
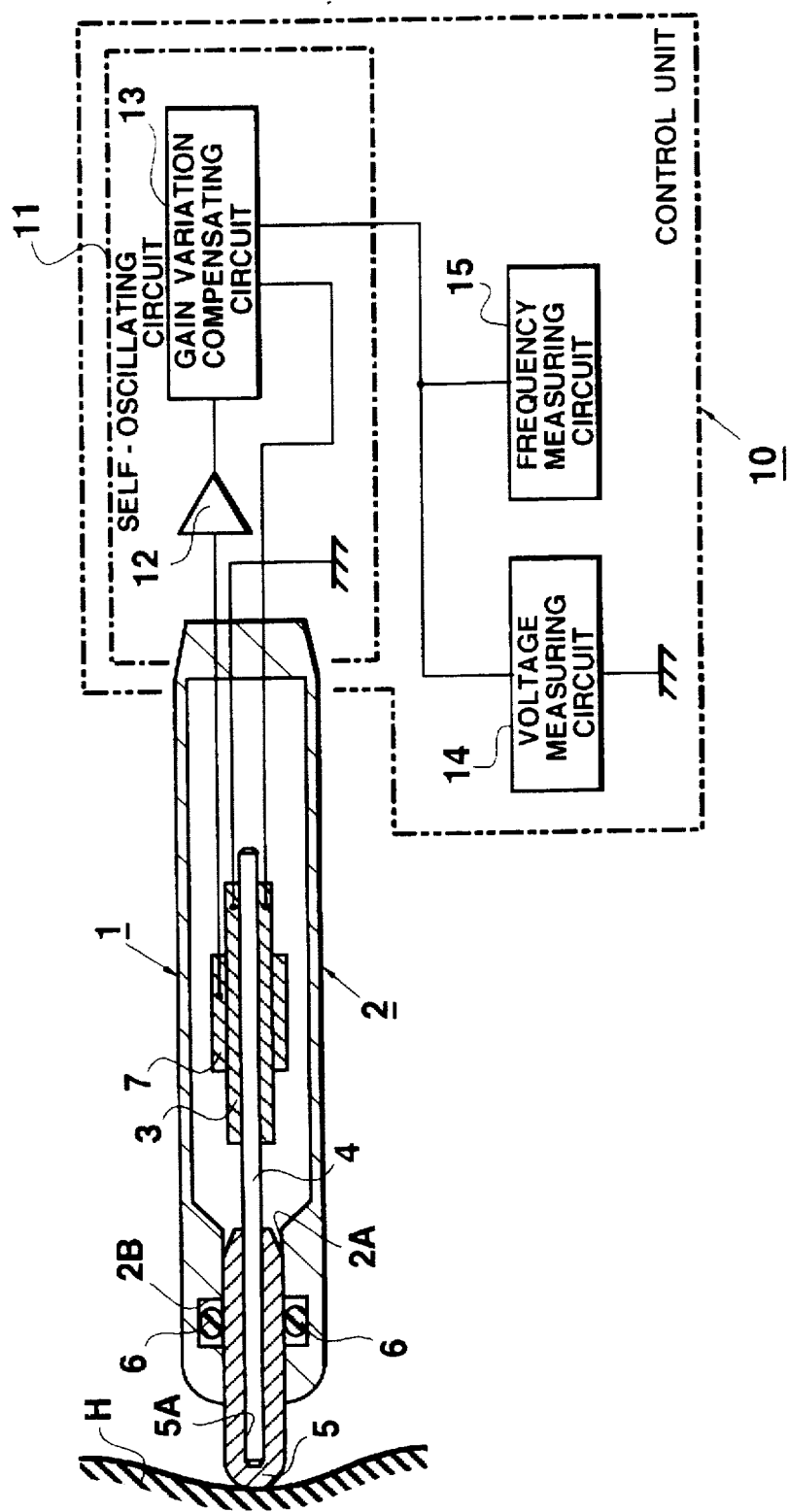
FIG. 1 shows the overall structure of a hardness measuring apparatus according to Embodiment 1 of the present invention.

In Embodiment 1 of the present invention, a hardness measuring apparatus utilizing a frequency deviation circuit is described. FIG. 1 shows the overall structure of a hardness measuring apparatus according to Embodiment 1 of the present invention. The hardness measuring apparatus has a hand piece 1 and a control unit disposed outside the hand piece 1.

Figure 2:
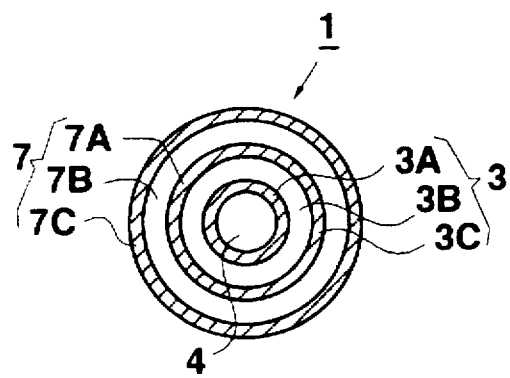
FIG. 2 shows a cross-sectional view of the main part of the oscillator.

The hand piece 1 has a casing 2 formed in a substantially cylindrical shape having a bottom. An oscillator 3 is disposed inside the middle portion of the casing 2. The oscillator 3 has a cylindrical shape. In this embodiment, a piezoelectric ceramic oscillator is used as the oscillator 3. FIG. 2 shows a cross-sectional view of the main part of the oscillator 3. The oscillator 3 comprises a first electrode 3A used as an anode, a second electrode 3C used as a cathode, and a piezoelectric crystal 3B formed between the first and second electrodes 3A and 3C. The piezoelectric crystal 3B has a cylindrical shape. The first electrode 3A is formed on the inner surface of the piezoelectric crystal 3B in a cylindrical shape. The second electrode 3C is formed on the outer surface of the piezoelectric crystal 3B in a cylindrical shape, and grounded. In the oscillator 3, a voltage varying with time is applied between the first and second electrodes 3A and 3C, causing mechanical oscillation of the piezoelectric crystal 3B. In a hardness measuring apparatus according to this embodiment, any of a quartz oscillator, a PVDF-based oscillator, a magnetostrictive element or a surface acoustic wave (SAW) element can be used as the oscillator 3, instead of the piezoelectric ceramic oscillator.

The oscillator 3 is mechanically coupled with a contact element 5 via an oscillation conducting member 4. An end portion of the oscillation conducting member 4, which extends inside the casing 2 toward its open end, is coaxially fixed on the inner surface of the second electrode 3C at a middle portion of the oscillator 3 with adhesive. The other end of the oscillation conducting member 4 is coupled with the contact element 5 with adhesive. As shown in FIG. 1, the contact element 5 is a cylinder having one closed end (tip portion), which is in contact with a subject H. The contact element 5 has a hole 5A at the center of the tip portion. The oscillation conducting member 4 is inserted into the hole 5A. The hole 5A of the contact element 5 and oscillation conducting member 4 are fixed with adhesive.

The contact element 5 is disposed inside an oscillation maintaining hole 2A formed at the end portion of the casing 2 facing toward the subject H. The tip portion of the contact element 5 facing toward the subject H projects from the end portion of the casing 2. The contact element 5 disposed inside the oscillation maintaining hole 2A can freely oscillate in the axial direction. A groove 2B is form ed on the inner surface of the oscillation maintaining hole 2A along its circumference. An elastic member 6 is put in the groove 2B. The contact element 5 is retained in the oscillation maintaining hole 2A of the casing 2 via the elastic member 6. The oscillation to be conducted to the contact element 5 from the oscillator 3 via the oscillation conducting member 4 is absorbed by the elastic member 6, and consequently it is not conducted to the hand piece 1. For example, an O-ring is used as the elastic member 6. In a hardness measuring apparatus according to this embodiment, the elastic member 6 works as a node of the oscillation of an electromechanical oscillation system described later. The node is formed at a connecting point of the oscillation conducting member 6 and the contact element 5, between the casing 2 and the contact element 5. The elastic member 6 is not always disposed at this position, and can be disposed between the electromechanical oscillation system and casing 2 at such a position that the oscillation of the electromechanical oscillation system is not conducted to the casing, and the casing 2 does not adversely affect the oscillation of the electromechanical oscillation system.

A detecting element 7 is placed on the outer surface of the oscillator 3 inside the casing 2. The detecting element 7 comprises a first electrode 7A used as a cathode, a second electrode 7C used as an anode, and a piezoelectric crystal 7B formed between the first and second electrodes 7A and 7C. An electrode cylindrically formed on the outer surface of the oscillator 3 is commonly used as the first electrode 7A of the detecting element 7 and the second electrode 3C of the oscillator 3. The piezoelectric crystal 7B is formed on the outer surface of the first electrode in a cylindrical shape. The second electrode 7C is formed on the outer surface of the piezoelectric crystal 7B in a cylindrical shape. The detecting element 7 basically comprises piezoelectric ceramic, as the oscillator 3. The detecting element 7 oscillates in synchronism with the oscillation of the oscillator 3, and is used as a sensor for detecting the oscillation as an electrical signal. The detecting element 7 outputs hardness information capable of monitoring the oscillation amplitude, frequency and phase of the oscillator 3 as a detection voltage.

A control unit 10 of the hardness measuring apparatus comprises a self-oscillating circuit 11, a gain variation compensating circuit 13, a voltage measuring circuit 14 and a frequency measuring circuit 15. The self-oscillating circuit 11 has an amplifying circuit 12, whose input terminal is connected to the output terminal (second electrode 7C) of the detecting element 7. The output terminal of the amplifying circuit 12 is connected to the input terminal (first electrode 3A) of the oscillator 3 via the gain variation compensating circuit 13.

The self-oscillating circuit 11 has the oscillator, detecting element 7 and amplifying circuit 12. The detecting element 7 detects oscillation information of the oscillator 3, and converts it into an electrical signal. The amplifying circuit 12 amplifies the electrical signal. The amplified electrical signal is fed back to the oscillator 3, leading to the formation of a feedback loop. The self-oscillating circuit 11 feeds back the oscillation information of the oscillator 3 via the detecting element 7 and amplifying circuit 12, forming an electrical oscillation system setting the oscillator 3 in a resonant state. The oscillator 3, oscillation conducting member 4 and contact element 5 form a mechanical oscillation system in which the oscillation information of the oscillator 3 is conducted to a subject H via the oscillation conducting member 4 and contact element 5. In a hardness measuring apparatus according to this embodiment, the electrical and mechanical oscillation systems are combined into an electromechanical oscillation system. The gain of the self-oscillation circuit 11 is almost proportional to the driving voltage of the self-oscillation circuit 11. The input terminal of this self-oscillating circuit 11 (input terminal of the electromechanical oscillation system) corresponds to the output terminal of the oscillator 3. The output terminal of the self-oscillating circuit 11 (output terminal of the electromechanical oscillation system) corresponds to the input terminal of the oscillator 3.

Figure 3:
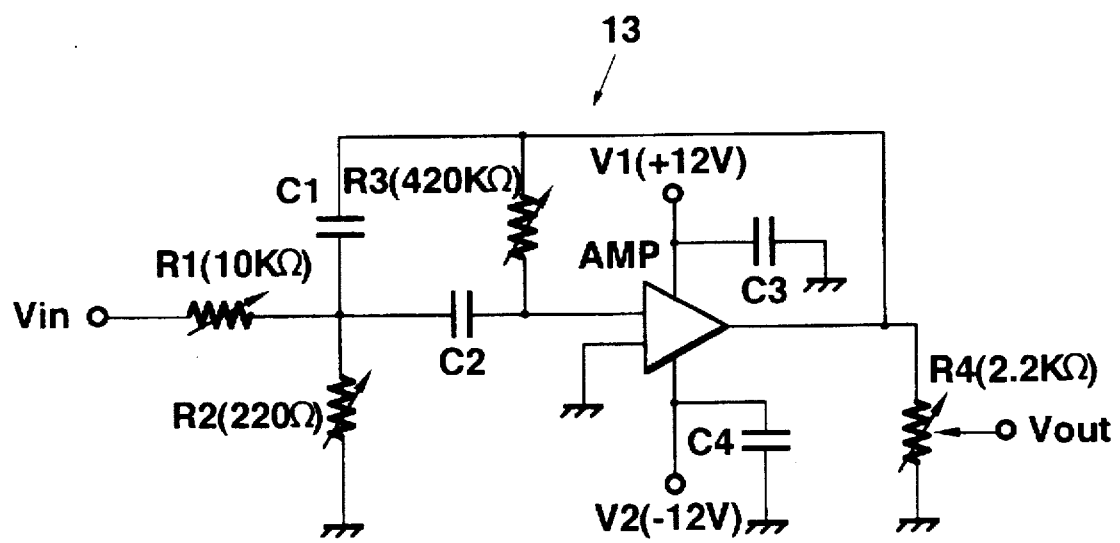
FIG. 3 shows the structure of a filter used as a gain variation compensating circuit.

The gain variation compensating circuit 13 increases the gain in response to a change in the resonance frequency of the electromechanical oscillation system, and has a function of increasing a detection voltage with an increase in the gain. In addition, the gain variation compensating circuit 13 has a phase transfer function of adjusting the difference between the input and output phases, called phase difference, of the self-oscillating circuit 11 to zero, and of promoting feedback oscillation, shifts the central frequency so that the phase difference becomes zero, and increases the gain in response to the change in the central frequency. In this embodiment, a filter circuit having a frequency-gain characteristic realizing a change in the gain in response to a change in frequency is used as the gain variation compensating circuit 13. FIG. 3 shows the structure of an example of the filter circuit used as the gain variation compensating circuit 13. This filter circuit has resistance elements R1, R2, R3 and R4, capacitance elements C1, C2, C3 and C4 and an amplifying circuit AMP. The resistance of the resistance element R1 is set at 10 k$\Omega$, that of the resistance element R2 at 220 $\Omega$, that of the resistance element R3 at 470 k$\Omega$, and that of the resistance element R4 at 2.2 k$\Omega$. A voltage of 12 V is supplied to the power terminal V1 of the amplifying circuit AMP. A reference supply voltage of $-12$ V is supplied to a reference supply voltage terminal V2. $V_{in}$ shown in FIG. 3 denotes the input terminal for a signal, and $V_{out}$ the output terminal. This filter circuit can work as a band-pass filter circuit. The input terminal $V_{in}$ of the filter circuit is connected to the output terminal of the amplifying circuit 12 included in the self-oscillating circuit 11. The output terminal $V_{out}$ is connected to the first electrode 3A (input terminal) of the oscillator 3. The gain variation compensating circuit 13 can be disposed between the oscillator 3 and amplifying circuit 12 of the self-oscillating circuit 11. In this case, the input terminal $V_{in}$ of the filter circuit is connected to the second electrode 7C (output terminal of the oscillator 3) of the detecting element 7. The output terminal $V_{out}$ is connected to the input terminal of the amplifying circuit 12.

In a hardness measuring apparatus according to this embodiment, the gain variation compensating circuit 13 is not limited to the band-pass filter circuit. Since any circuit having such a characteristic that it changes the gain in response to a change in frequency, and then increases the detection voltage with the increase in the gain, can be used as the gain variation compensating circuit 13, any of a low-pass filter circuit, high-pass filter circuit, notch filter circuit, integrating circuit, differentiating circuit or peaking amplifying circuit can be used.

The voltage measuring circuit 14 and frequency measuring circuit 15 of the control unit 10 shown in FIG. 1 are respectively connected to the gain variation compensating circuit 13. The voltage measuring circuit 14 and frequency measuring circuit 15 is connected to the output terminal $V_{out}$ of the filter circuit (gain variation compensating circuit 13). The voltage measuring circuit 14 is used for measuring a change in the voltage of the electromechanical oscillation system, and the frequency measuring circuit 15 for measuring a change in the frequency of the electromechanical oscillation system. In a hardness measuring apparatus according to this embodiment, the hardness of a subject can be determined by the change in the frequency of the electromechanical oscillation system formed as described above. The gain is increased by the gain variation compensating circuit 13, leading to an increased detection voltage. In addition, the hardness information of a subject can be monitored by the voltage measuring circuit 14 and frequency measuring circuit 15 of the control unit 10. The voltage measuring circuit 14 and frequency measuring circuit 15 are not always connected to the output terminal of the gain variation compensating circuit 13. They may be coupled with the electromechanical oscillation system in any manner.

[Basic Principle of Hardness Measurement]

Figure 4:
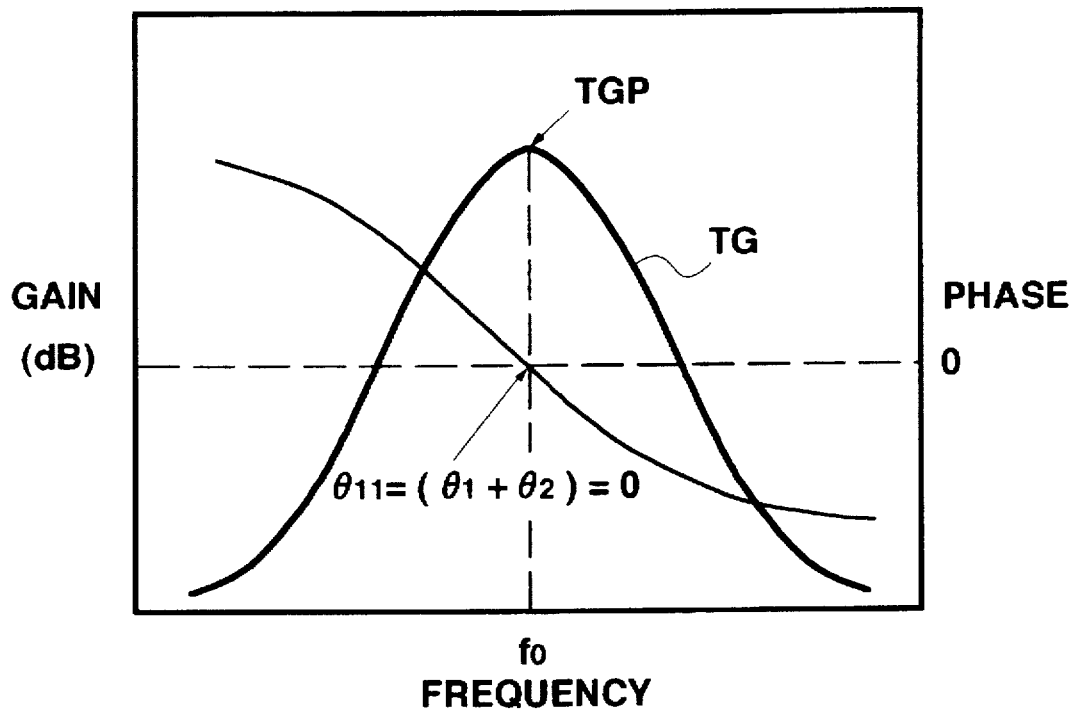
FIG. 4 shows characteristic curves which represent a total gain-frequency characteristic and total phase-frequency characteristic, which are obtained by combining the gain-frequency characteristics and the phase-frequency characteristics of the self-oscillating circuit and gain variation compensating circuit.

The basic principle of a hardness measuring apparatus provided by the present invention will be described. FIG. 4 shows a total gain-frequency characteristic and a total phase-frequency characteristic, which are obtained by combining the gain-frequency characteristics, and the phase-frequency characteristics of the self-oscillating circuit 11 and gain variation compensating circuit 13. In FIG. 4, the horizontal axis represents frequency, and the vertical axes gain and phase, respectively. The characteristic curve TG shows a gain-frequency characteristic of the self-oscillating circuit 11 in which a signal is outputted from the output terminal of the oscillator 3 (actually the output terminal of the detecting element 7), and fed back to the oscillator 3 via the gain variation compensating circuit 13. The gain-frequency characteristic curve TG shows a total frequency characteristic obtained by combining the frequency characteristic of the self-oscillating circuit 11 with that of the gain variation compensating circuit 13. The gain-frequency characteristic curve TG shows that the gain increases with the increase in frequency in a lower frequency band, has a peak at a resonance frequency $f_0$, and then decreases with the increase in frequency in a higher frequency band, making an arched curve. The phase characteristic curve $\theta_{11}$ shows the difference between the input and output phases (phase difference) of the self-oscillation circuit 11.

In a hardness measuring apparatus according to this embodiment, the difference between the input and output phases of the self-oscillation circuit 11 is adjusted to zero at a resonance frequency $f_0$ at which the gain-frequency characteristic curve TG shows a maximum value TGP. In the self-oscillating circuit 11, the phase difference $\theta_{11}$ between the phase $\theta_1$ (input phase) of a signal outputted from the oscillator 3 at a resonance frequency and phase $\theta_2$ (output phase) of a signal which is outputted from the gain variation compensating circuit 13, and fed back to the input terminal of the oscillator 3 after increasing the gain of the signal, is adjusted to zero ($\theta_{11}=\theta_1+\theta_2=0$). When the phase difference between the input phase $\theta_1$ and output phase $\theta_2$ is not equal to zero, the feedback is repeatedly carried out until the phase difference becomes zero. The oscillation is performed at a phase difference of zero. Consequently, the feedback oscillation of the self-oscillating circuit 11 including the gain variation compensating circuit 13 is ensured and promoted by the adjustment of the phase difference $\theta_{11}$, to zero. In a hardness measuring apparatus according to this embodiment, the gain variation compensating circuit 13 carries out the adjustment of the phase difference $\theta_{11}$, and can easily adjust the phase difference $\theta_{11}$ by shifting the central frequency in the frequency characteristic.

Figure 5:
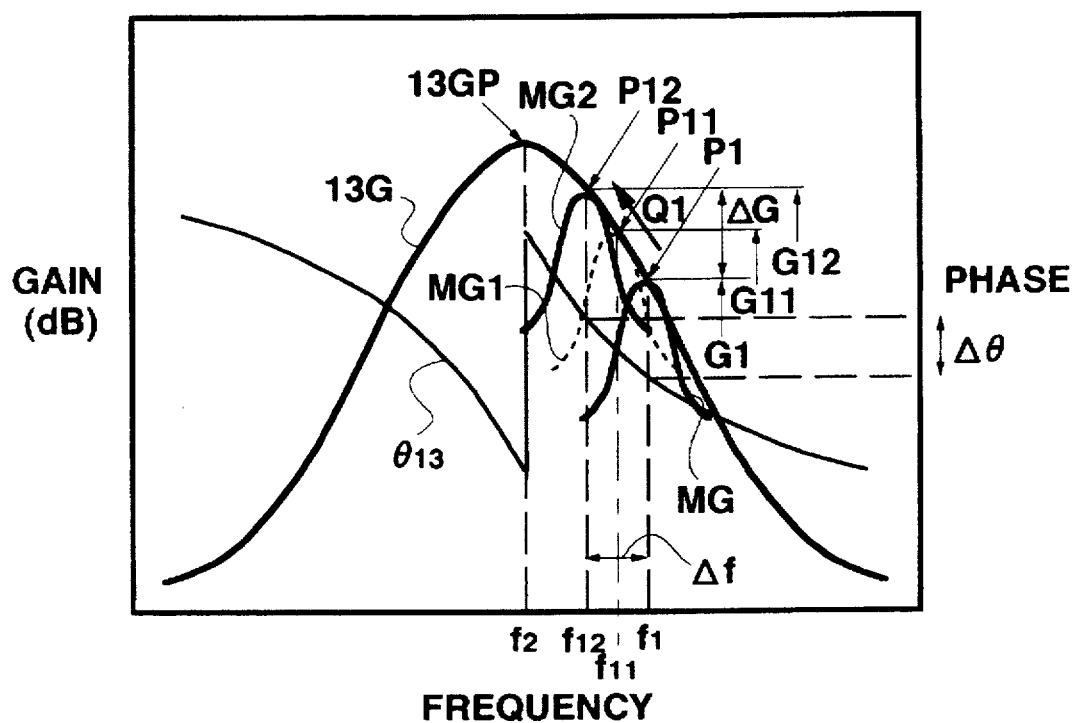
FIG. 5 shows characteristic curves representing gain-frequency and phase-frequency characteristics of the self-oscillating circuit and gain variation compensating circuit.

FIG. 5 shows characteristic curves representing gain-frequency and phase-frequency characteristics of the self-oscillating circuit 11 and gain variation compensating circuit 13. The horizontal axis represents frequency, and the vertical axes represent gain and phase, respectively. The characteristic curve 13G shows a gain-frequency characteristic of the gain variation compensating circuit 13. In the gain-frequency characteristic curve 13G, the gain increases with the increase in frequency in a lower frequency band, reaches a maximum value, and then decreases in a higher frequency band, showing an arched curve. The characteristic curve $\theta_{13}$ shows a phase difference between the input and output phases of the gain variation compensating circuit 13. The characteristic curve MG shows a gain-frequency characteristic of the self-oscillating circuit, that is, the electromechanical oscillation system itself, not including a characteristic of the gain variation compensating circuit 13. The gain-frequency characteristic curve MG is also an arched curve as the frequency characteristic of the gain variation compensating circuit 13, although the central frequency and maximum value of the gain are different. This gain-frequency characteristic curve MG is obtained when the contact element 5 is not in contact with a subject H.

In a hardness measuring apparatus according to this embodiment, as shown by the gain-frequency characteristic curves MG and 13G, the central frequency $f_1$ (resonance frequency) of the electromechanical oscillation system, at which the gain has a maximum value P1, and the central frequency $f_2$, at which the gain of the gain variation compensating circuit 13 has a maximum value 13GP, are intentionally set in different frequency bands. When the contact element 5 is in contact with a soft subject H, such as human skin or a human internal organ, the total gain should be increased. Therefore, the central frequency $f_2$ of the gain of the gain variation compensating circuit 13 is set at a lower frequency than the central frequency $f_1$ of the gain of the electromechanical oscillation system. When the contact element 5 is in contact with a hard subject H, such as metal, bone or tooth, the central frequency $f_2$ of the gain of the gain variation compensating circuit 13 is set at a higher frequency than the central frequency $f_1$ of the gain of the electromechanical oscillation system in order to increase the total gain.

When the contact element 5 of a hardness measuring apparatus according to this embodiment comes into contact with a soft subject H, the mechanical or acoustic impedance of the soft subject is increased. This causes a change in the oscillation mode of the oscillator 3, leading to a change in the frequency characteristic of the electromechanical oscillation system. All the oscillation frequency, gain, phase and oscillation amplitude included in the oscillation information can be varied. The oscillation frequency is shifted toward a lower frequency due to the impedance of the soft subject H. A maximum value of the gain is originally decreased in general but in contrast, it is increased in a hardness measuring apparatus according to this embodiment due to the gain increasing function of the gain variation compensating circuit 13. The maximum value of the gain increases from the maximum value P1 along the gain-frequency characteristic curve 13G of the gain variation compensating circuit 13. At the instant the contact element 5 comes into contact with a soft subject H, the central frequency $f_1$ of the electromechanical oscillation system is changed to a resonance frequency $f_{11}$ determined by the impedance of the subject H. The gain-frequency characteristic curve MG of the electromechanical oscillation system is shifted to a gain-frequency characteristic curve MG1. As shown in the gain-frequency characteristic curve MG1, the maximum value P1 of the gain is changed to a maximum value P11, and the gain G1 to G11, leading to an increase in the gain. Oscillation information, including the changes in the frequency and gain, is detected by the detecting element 7. This oscillation information detected by the detecting element 7 is fed back to the oscillator 3 by the feedback loop of the self-oscillating circuit 11.

The feedback loop of the self-oscillating circuit 11 has a circuit in which a combination of resistance and capacitance elements is used. Therefore, the phase difference $\Delta\theta$ between the input phase $\theta_1$ and output phase $\theta_2$ is always non-zero. The gain variation compensating circuit 13 has a phase transfer function of adjusting the phase difference $\theta_{11}$ between the input and output phases of the feedback loop including itself to zero. Therefore, the frequency further changes, and the gain increases until they both reach a stable point in the feedback oscillation at a phase difference $\theta_{11}$ of zero. The gain-frequency characteristic curve MG1 of the electromechanical oscillation system is changed to a gain-frequency characteristic curve MG2, and the resonance frequency $f_{11}$ to a resonance frequency $f_{12}$. The maximum value P11 of the gain is changed to a maximum value P12, and the gain G11 to a gain G12 in response to the change in the resonance frequency to $f_{12}$, leading to a further increase in the gain. The central frequency $f_1$ of the electromechanical oscillation system is continuously varied to the resonance frequency $f_{12}$ by a frequency corresponding to the phase difference $\Delta\theta$, and the gain G1 is continuously increased to G12. Consequently, a variation $\Delta f$ in the frequency and a variation $\Delta G$ in the gain are obtained in the electromechanical oscillation system. When the variation $\Delta f$ and variation $\Delta G$ are obtained, the phase difference $\theta_{11}$ between the input and output phases becomes zero, enabling the self-oscillation circuit to carry out feedback oscillation.

A hardness measuring apparatus according to this embodiment detects the variation $\Delta f$ between the frequencies before and after contacting the contact element 5 with a soft subject H, as hardness information. This enables the hardness of a soft subject H to be measured. Similarly, the hardness measuring apparatus according to this embodiment detects the phase difference $\Delta\theta$ between the phases before and after contacting the contact element 5 with a soft subject H, as hardness information. This also enables the hardness of a soft subject H to be measured. In addition, the hardness measuring apparatus according to this embodiment enables the gain to be increased in response to the variation $\Delta f$ and phase difference $\Delta\theta$ (a sufficient variation $\Delta G$ in the gain to be obtained), obtaining a detection voltage sufficient for hardness measurement.

Figure 6:
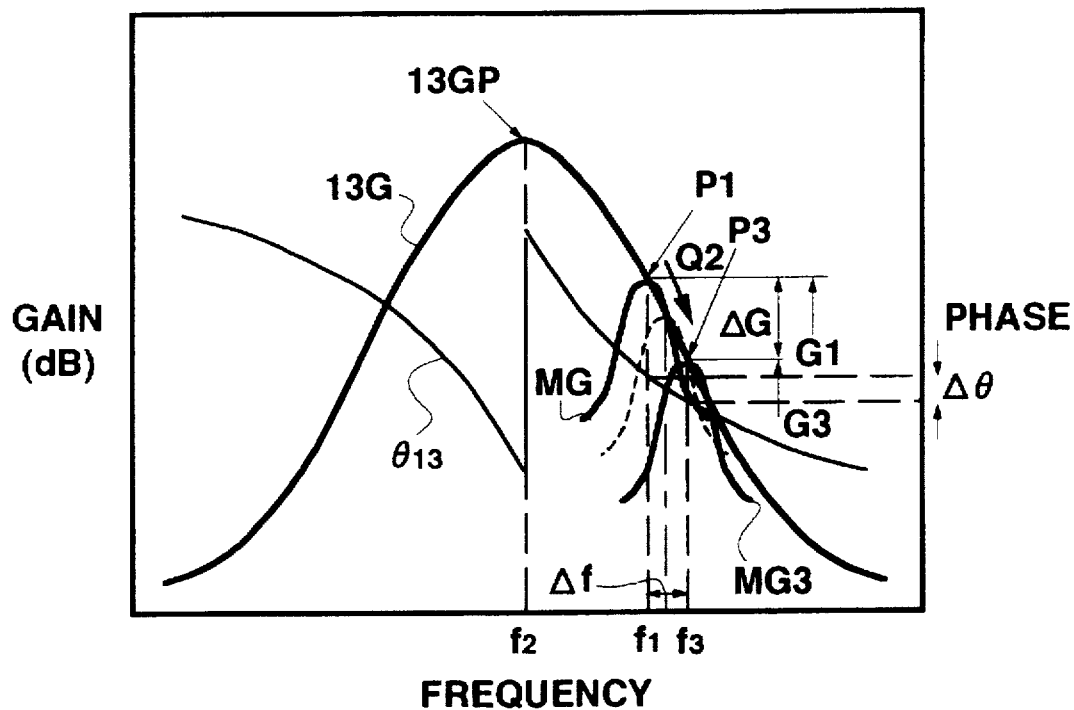
FIG. 6 shows characteristic curves representing gain-frequency and phase-frequency characteristics of the self-oscillating circuit and gain variation compensating circuit.

In a hardness measuring apparatus according to this embodiment, when contacting the contact element 5 with a hard subject H, the frequency, gain, phase and oscillation amplitude are changed, but the gain is not increased, because an adjustment appropriate to measuring the hardness of a soft subject H is made. FIG. 6 shows gain-frequency characteristic curves and phase-frequency characteristic curves of the self-oscillating circuit 11 and gain variation compensating circuit 13. The characteristic curve MG3 shows a gain-frequency characteristic of the electromechanical oscillation system when contacting the contact element 5 with a hard subject H. When contacting the contact element 5 with a hard subject H, the resonance frequency is changed to a frequency determined by the impedance of the subject H at the instance of contacting. Subsequently, the frequency is changed by a frequency corresponding to the phase difference $\Delta\theta$ to a resonance frequency $f_3$ at which the phase difference $\theta_{11}$ between the input and output phases becomes zero, enabling feedback oscillation to be carried out. The change in the frequency is shifted toward a higher frequency, and then the variation $\Delta f$ in the frequency is increased until the phase difference $\theta_{11}$ becomes zero, leading to a larger value. Consequently, the gain-frequency characteristic curve MG1 of the electromechanical oscillation system is shifted to a gain-frequency characteristic curve MG3. The maximum value P1 of the gain is changed to a maximum value P3 at which feedback oscillation is stably carried out.

The gain variation compensating circuit 13 of a hardness measuring apparatus according to this embodiment has both the gain increasing function and phase transfer function. In the present invention, the gain variation compensating circuit 13 may have only the gain increasing function.

The relationship between the resonance frequency of an oscillator and the mechanical properties of a material with which the oscillator is to be in contact with is described by S. Omata in "Measurements of the hardness of a soft material with a piezoelectric vibrometer and their analysis" *Iyodenshi to Seitaikogaku* (*Journal of the Japan Society of Medical Electronics and Biological Engineering*), Vol. 28, No. 1, pp. 1–4 (1990).

[Use of a Hardness Measuring Apparatus]

The use of a hardness measuring apparatus according to this embodiment will be described. In the above mentioned hardness measuring apparatus shown in FIG. 1, an electromechanical oscillation system, which includes the oscillator 3, detecting element 7, oscillation conducting member 4 and contact element 5, is oscillated in a resonant state by the self-oscillating circuit 11, so that the hardness measuring apparatus is set in operation. Oscillation information, that is, the frequency, gain, phase and oscillation amplitude, of this electromechanical oscillation system, is outputted from the output terminal of the gain variation compensating circuit 13. The detection voltage is monitored by the voltage measuring circuit 14, and the frequency is monitored by the frequency measuring circuit 15. A person measuring the hardness holds the hand piece I by hand, and contacts the tip of the contact element 5 oscillating in a resonant state with a subject H.

At this time, the detection voltage and frequency for the electromechanical oscillation system detected by the voltage measuring circuit 14 and frequency measuring circuit 15 respectively, are changed in response to the hardness of the subject H, as follows:

A highly elastic and soft subject, such as a biological soft tissue (human skin, human internal organs) or rubber, has a low mechanical or acoustic impedance, reducing the resonance frequency of the electromechanical oscillation system. As shown in FIG. 5, the electromechanical oscillation system has a gain-frequency characteristic shown by the characteristic curve MG having a maximum value P1 of the gain at a central frequency $f_1$ before contacting the contact element 5 with the subject H. A hardness measuring apparatus according to this embodiment has the gain variation compensating circuit 13 which increases the gain in response to a change in the resonance frequency. In the gain variation compensating circuit 13, the gain is set to be increased in response to a change in the frequency when contacting the contact element 5 with a soft subject H. The gain-frequency characteristic curve MG of the electromechanical oscillation system is corrected by the gain-frequency characteristic curve 13G of the gain variation compensating circuit when bringing the contact element 5 into contact with a soft subject H. Consequently, the gain-frequency characteristic curve MG of the electromechanical oscillation system is shifted in the direction indicated by the arrow Q1 shown in FIG. 5. In addition, the gain variation compensating circuit has the phase transfer function, and the phase difference $\theta_{11}$ between the input and output phases in the feedback (closed) loop formed by the self-oscillating circuit 11 is adjusted to zero, enhancing the variation in the frequency by a frequency corresponding to a phase difference $\Delta\theta$. The increase in the gain is enhanced by this change in the frequency. At an appropriate stable point of feedback oscillation, the change in the frequency and the increase in the gain stop, and the feedback oscillation of the electromechanical oscillation system occurs. The gain-frequency characteristic curve MG is changed into a gain-frequency characteristic curve MG2, and the maximum value P1 of the gain is increased to a maximum value P12.

A hardness measuring apparatus according to this embodiment is set to be suitable for measuring the hardness of a soft subject H. When measuring the hardness of a hard subject H, such as iron or an alloy at room temperature, the frequency is changed, but the gain is not increased. As shown in FIG. 6, the gain-frequency characteristic curve MG of the electromechanical oscillation system is shifted in the direction indicated by the arrow Q2 to a gain-frequency characteristic curve MG3. Although the gain is decreased, the variation in the frequency is enhanced by the phase transfer function. The hardness of a hard subject H can be determined by monitoring this variation in the frequency using the frequency measuring circuit 15. In order to set the gain to be increased when measuring the hardness of a hard subject H, the central frequency of the electromechanical oscillation system is set in a lower frequency band, in which the gain is increased with an increase in the frequency, in the gain-frequency characteristic curve 13G of the gain variation compensating circuit 13.

In a hardness measuring apparatus according to this embodiment, a change in the voltage of the electromechanical oscillation system is monitored by the voltage measuring circuit 14, and a change in the resonance frequency is monitored by the frequency measuring circuit 15, in order to determine the hardness of a subject.

[Results of the Measurement of Hardness]

Figure 7:
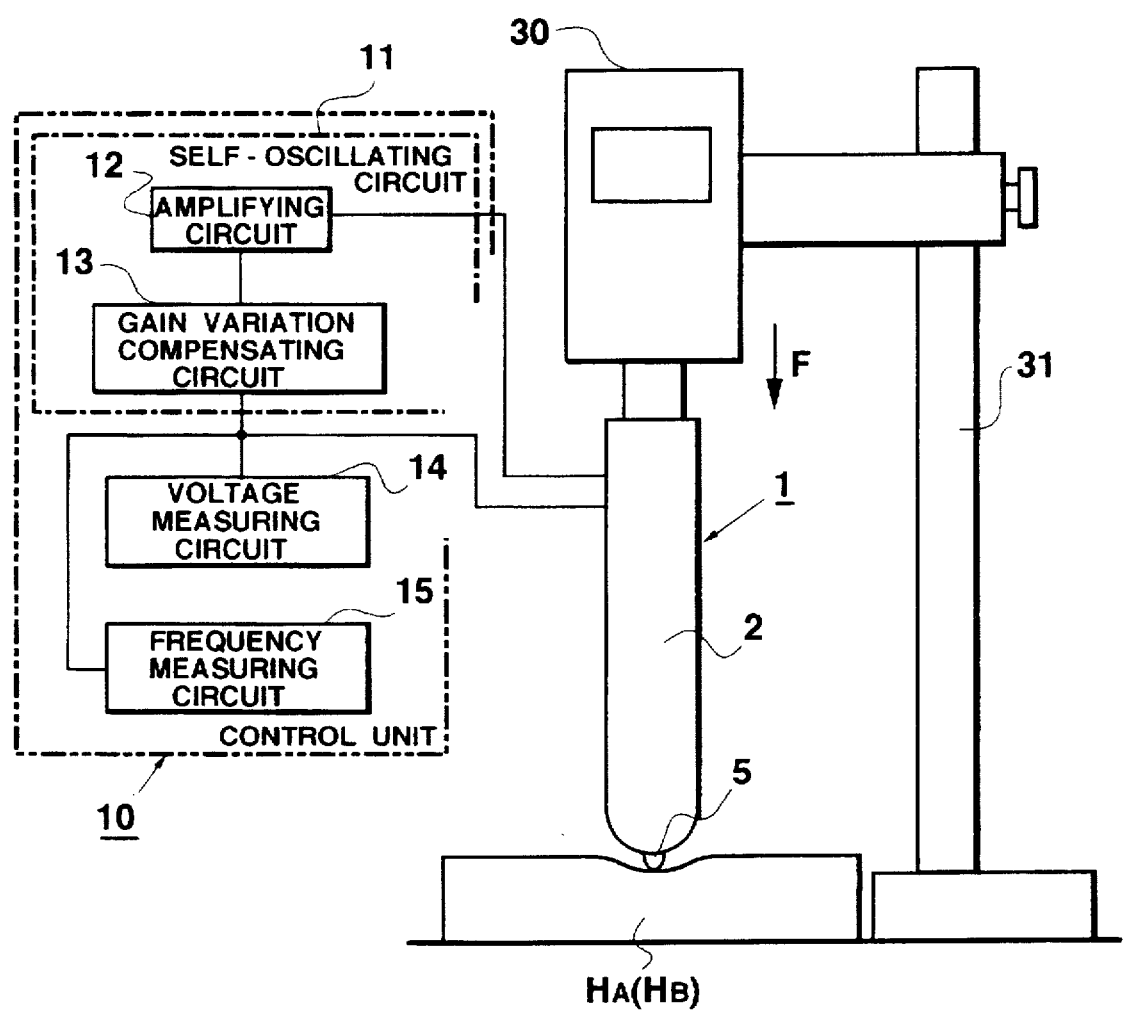
FIG. 7 shows the structure of an actual system for measuring the hardness of a subject.

FIG. 7 shows the structure of an actual system for measuring the hardness of a subject H. The hand piece 1 of a hardness measuring apparatus is coupled with a holding stand 31 via a load cell 30 to be used for measuring the hardness of a subject H. The compressive force applied to the subject H by the contact element 5 can be measured by the load cell 30.

Figure 8:
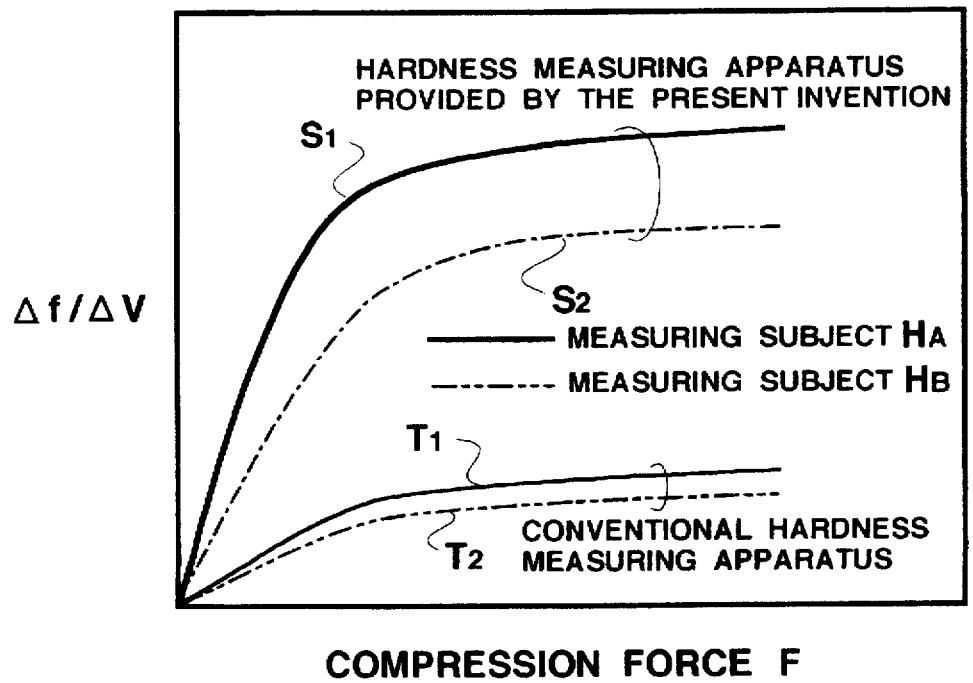
FIG. 8 shows variations in resonance frequency and detection voltage plotted against compressive force.

FIG. 8 shows variations in the frequency and detection voltage of a hardness measuring apparatus according to this apparatus and those in a conventional one, which are plotted against the compressive force. The horizontal axis indicates a compressive force F measured by the load cell 30, and the vertical axis indicates a variation in the resonance frequency $\Delta f$ or in the detection voltage $\Delta V$. Two subjects $H_A$ and $H_B$ having different hardnesses are used as the subject H. The curves $S_1$ and $S_2$ show variations in the frequency and voltage in a hardness measuring apparatus according to this embodiment, plotted against the compressive force. The curve $S_1$ shows the variation for the subject $H_A$, and the curve $S_2$ the variation for the subject $H_B$. The curves $T_1$ and $T_2$ show variations in the frequency and detection voltage in a conventional hardness measuring apparatus, plotted against the compressive force. The curve $T_1$ shows the variation for the subject $H_A$, and the curve $T_2$ the variation for the subject $H_B$.

As shown in FIG. 8, the variations in the frequency and detection voltage increase with the increase in compressive force to a small extent in a conventional hardness measuring apparatus, and the difference between the variations for the subjects $H_A$ and $H_B$ is small, even when the hardnesses (acoustic impedance) of the subjects $H_A$ and $H_B$ are different. Sufficient variations in the frequency and detection voltage for measuring the hardnesses of the subjects $H_A$ and $H_B$ cannot be obtained. In contrast, the variations in frequency and detection voltage increase with the increase in compressive force to a much larger extent in a hardness measuring apparatus according to this embodiment than the variations in a conventional hardness measuring apparatus, and the difference between the variations for the subjects $H_A$ and $H_B$ is large. A hardness measuring apparatus according to this embodiment can enhance a slight difference between variations in the resonance frequency or detection voltage which is derived from the difference between the hardnesses (acoustic impedances) of subjects.

When a hardness measuring apparatus has the gain variation compensating circuit 13, and the resonance frequency of the electromechanical oscillation system is set in a frequency band in which the gain is increased in response to a change in the frequency of the gain variation compensating circuit 13, the gain is increased in response to a change in the frequency due to a slight difference between the hardnesses of subjects H. When the hardness of a subject H with a similar hardness and having a similar frequency characteristic is measured, the phase transfer function of the gain variation compensating circuit 13 enhances the variation in the frequency until the phase difference is cancelled to zero, and further increases the gain. This enables a sufficient detection voltage for determining the hardness of a subject to be obtained. In addition, when the hardnesses of various subjects H are measured, the variation in the frequency is enhanced, enabling the measurement of hardness for soft and hard subjects H to be realized in a wide range. The effective resonance frequency band of the electromechanical oscillation system of a hardness measuring apparatus is expanded, realizing measurement of the hardness of various subjects H in a wide range.

In a hardness measuring apparatus according to this embodiment, the gain variation compensating circuit 13 can be easily achieved by a filter circuit comprising a simple combination of resistance elements, capacitance elements and the like. Complicated circuitry is not necessary for the gain variation compensating circuit 13, enabling a simple structure and fabrication with low cost.

[Modification 1]

Figure 9:
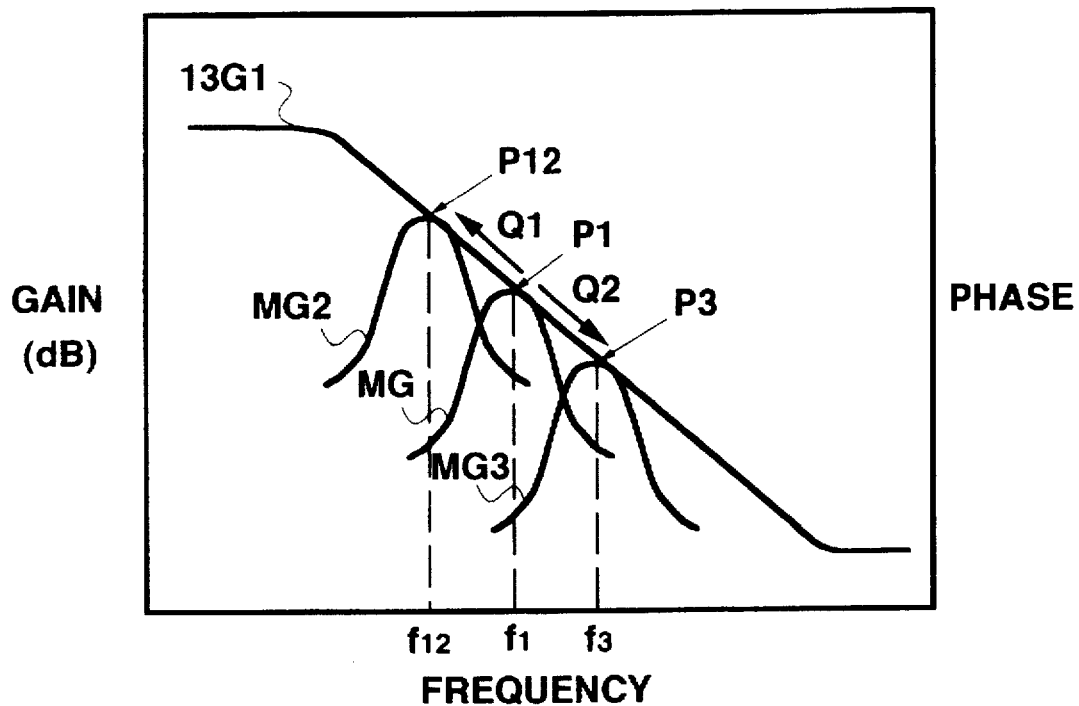
FIG. 9 shows gain-frequency characteristic curves of a hardness measuring apparatus according to a modification of Embodiment 1.
Figure 10:
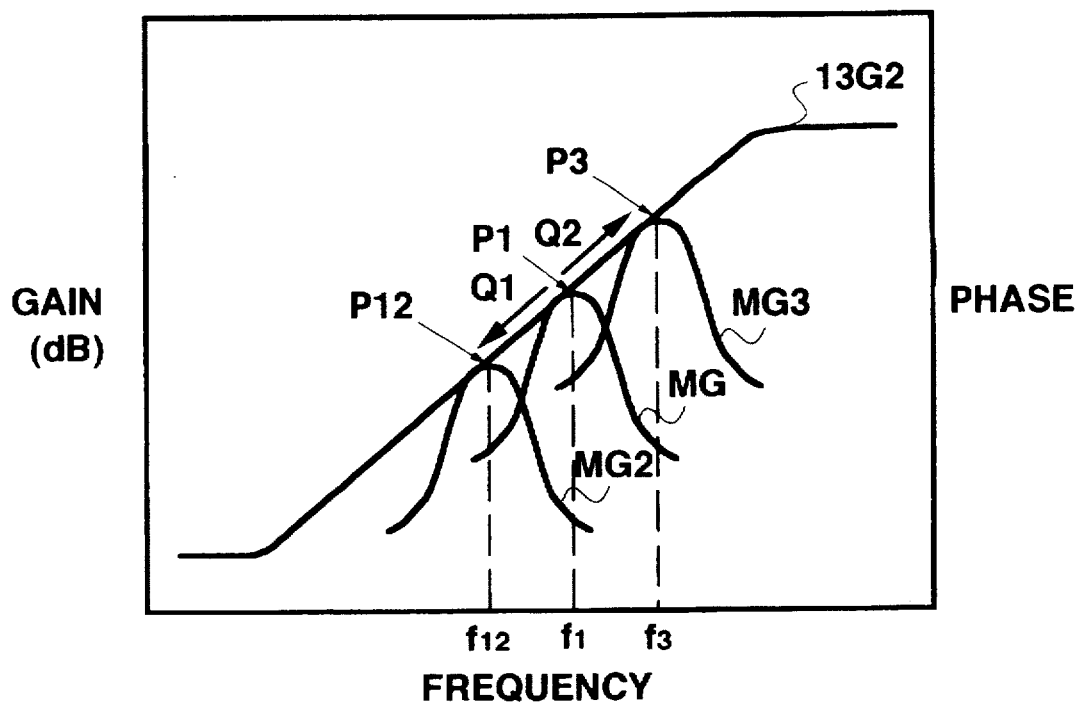
FIG. 10 shows gain-frequency characteristic curves of a hardness measuring apparatus according to a modification of Embodiment 1.

FIGS. 9 and 10 show gain-frequency characteristic curves of a hardness measuring apparatus according to Modification 1 of Embodiment 1. FIG. 9 shows gain-frequency characteristic curves when a low-pass filter is used as the gain variation compensating circuit 13. A gain-frequency characteristic curve 13G1 of the gain variation compensating circuit 13 and gain-frequency characteristic curve MG of the electromechanical oscillation system are shown. In this hardness measuring apparatus, a variation in frequency is basically amplified in a similar manner to that in a hardness measuring apparatus including a band-pass filter circuit (see FIG. 3). In particular, when the contact element 5 is in contact with a soft subject H, the frequency is changed. The variation in the frequency is enhanced, and the gain is increased by the variation in the frequency. As described before, the gain variation compensating circuit 13 has both the gain increasing function and the phase transfer function. Having both functions enables a larger variation in the frequency and a larger gain.

FIG. 10 shows gain-frequency characteristic curves when a high-pass filter circuit is used as the gain variation compensating circuit 13. A gain-frequency characteristic curve 13G2 of the gain variation compensating circuit 13 and gain-frequency characteristic curve MG of the electromechanical oscillation system are shown. This hardness measuring apparatus is suitable for measuring the hardness of a hard subject H, such as a metal like iron or an alloy, and a human hard tissue such as a bone or tooth. In this hardness measuring apparatus, when the contact element 5 comes into contact with a soft subject H, the frequency is changed, the variation in the frequency is enhanced, and the gain is increased by the variation in the frequency. In FIG. 10, a gain-frequency characteristic curve MG when the contact element 5 is not in contact with a hard subject is shifted to a gain-frequency characteristic curve MG3. A detection voltage sufficient for the measurement of hardness can be obtained by increasing the gain. In this hardness measuring apparatus, when the contact element 5 is in contact with a soft subject H, the gain-frequency characteristic curve MG of the electromechanical oscillation system is shifted to a gain-frequency characteristic curve MG1, decreasing the gain.

[Modification 2]

Figure 11:
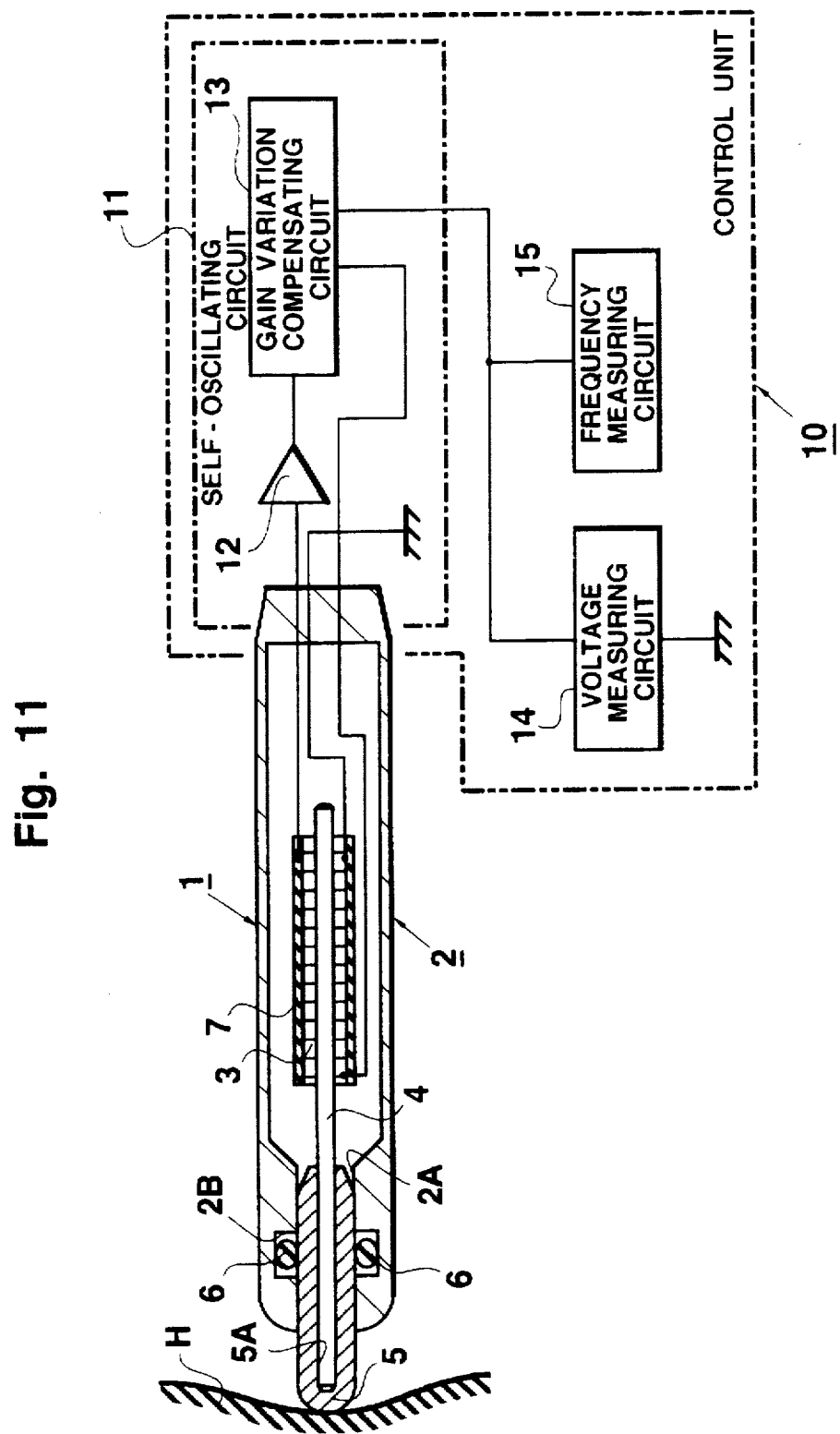
FIG. 11 shows the overall structure of a hardness measuring apparatus according to Modification 2 of Embodiment 1.

FIG. 11 shows the overall structure of a hardness measuring apparatus according to Modification 2 of Embodiment 1. This hardness measuring apparatus includes an oscillator 3 comprising a layered piezoelectric ceramic oscillator and a detecting element 7 comprising a film bimorph oscillator. These oscillator 3 and detecting element 7 form the electromechanical oscillation system. In the layered piezoelectric ceramic oscillator 3, a ring-shaped piezoelectric ceramic is fixed around an oscillation conducting member 4 with adhesive, and is layered numerous times in the axial direction of the oscillation conducting member 4. The size of the layered piezoelectric ceramic oscillator is small, and an input voltage of large amplitude can be obtained.

The detecting element 7 comprising the bimorph oscillator is fixed on the outer surface of the oscillator 3 (layered piezoelectric ceramic oscillator). The detecting element 7 fabricated in a film form has a small weight, and only requires a small space in the casing 2 of the hand piece 1 for disposition. An oscillator comprising a PVDF film can be used in the detecting element 7 instead of the bimorph oscillator.

A hardness measuring apparatus having such a structure includes the oscillator 3 comprising a layered piezoelectric ceramic oscillator and the detecting element 7 comprising a film bimorph oscillator. Therefore, it has the advantage obtained by the hardness measuring apparatus shown in FIG. 1, and also its oscillator 3 outputs a sufficiently large amplitude, enabling the size and weight to be reduced. The detecting element 7 of the hardness measuring apparatus is fabricated in a film form, also enabling its size and weight to be reduced. Consequently, the size and weight of composite elements inside the hand piece 1 can be reduced, enabling the size and weight of the hand piece 1 itself to be reduced. The operability of the hand piece 1, that is, of the hardness measuring apparatus, can be improved.

[Modification 3]

Figure 12:
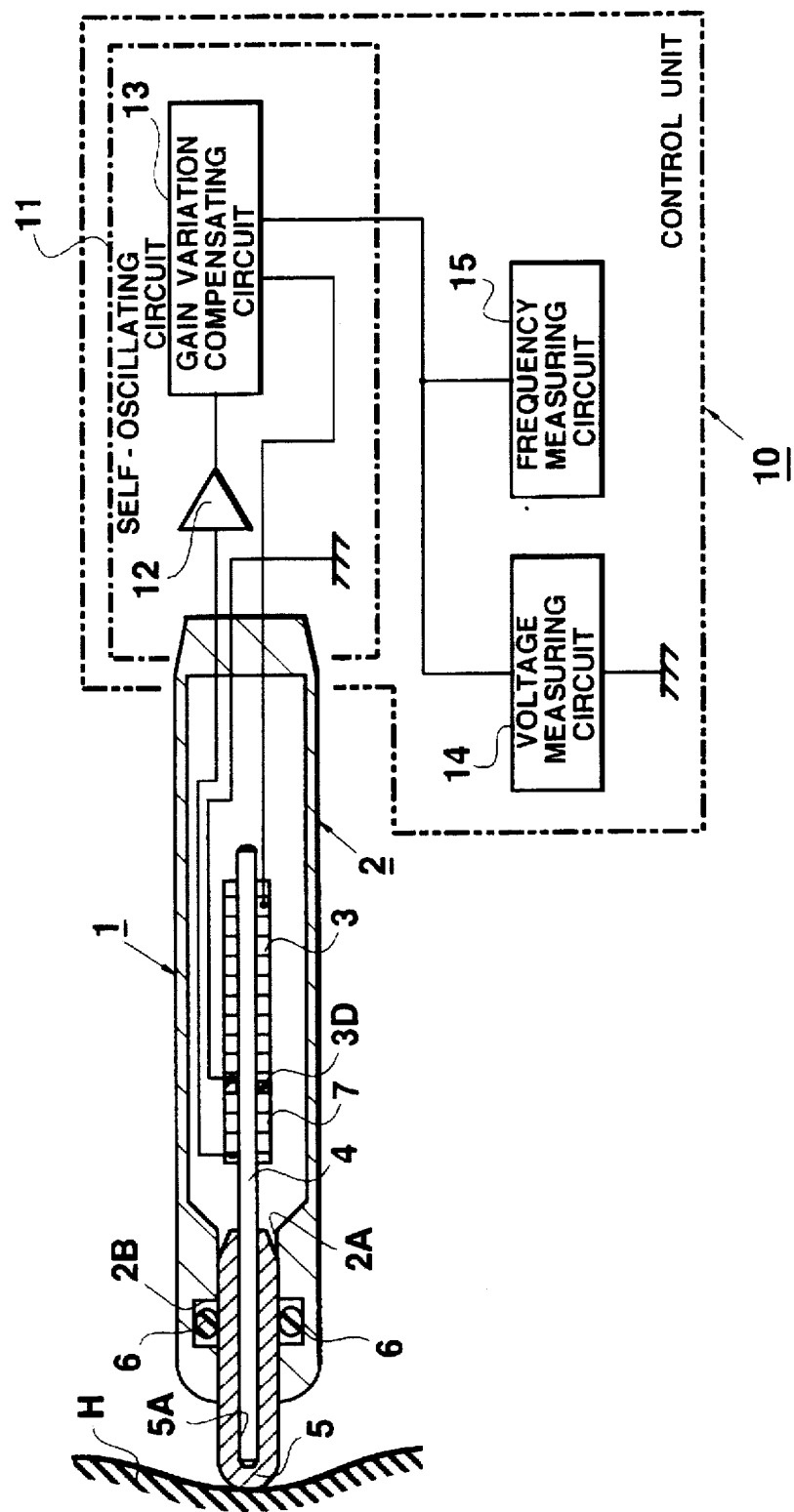
FIG. 12 shows the overall structure of a hardness measuring apparatus according to Modification 3 of Embodiment 1.

FIG. 12 shows the overall structure of a hardness measuring apparatus according to Modification 3 of Embodiment 1. This hardness measuring apparatus includes an oscillator 3 comprising a layered piezoelectric ceramic oscillator, a detecting element 7 comprising a layered piezoelectric ceramic oscillator and an insulation material 3D. These oscillator 3 and detecting element 7 form the electromechanical oscillation system. In the layered piezoelectric ceramic oscillator of the oscillator 3, a ring-shaped piezoelectric ceramic is fixed around an oscillation conducting member 4 with adhesive, and is layered numerous times in the axial direction of the oscillation conducting member 4. As mentioned above , the size of the layered piezoelectric ceramic is small, and an input voltage of large amplitude can be obtained.

The layered piezoelectric ceramic oscillator comprising the detecting element 7 is disposed closer to the contact element 5 than to the oscillator 3. As in the oscillator 3, a ring-shaped piezoelectric ceramic is fixed around an oscillation conducting member 4 with adhesive, and is layered numerous times in the axial direction of the oscillation conducting member 4.

The insulation material 3D is disposed between the oscillator 3 and detecting element 7. The oscillator 3 of the layered piezoelectric ceramic oscillator, insulation material 3D and detecting element 7 are fabricated as an integrated assembly.

A hardness measuring apparatus having such a structure includes the oscillator 3 comprising layered piezoelectric ceramic oscillator and the detecting element 7 comprising a film bimorph oscillator. Therefore, it has the advantage obtained by the hardness measuring apparatus shown in FIG. 1, and also its oscillator 3 outputs a sufficiently large amplitude, enabling the size and weight to be reduced. The detecting element 7 of the hardness measuring apparatus is fabricated in a film form, also enabling its size and weight to be reduced. Consequently, the size and weight of composite elements inside the hand piece 1 can be reduced, enabling the size and weight of the hand piece 1 itself to be reduced. The operability of the hand piece 1, that is, of the hardness measuring apparatus, can be improved.

[Modification 4]

Figure 13:
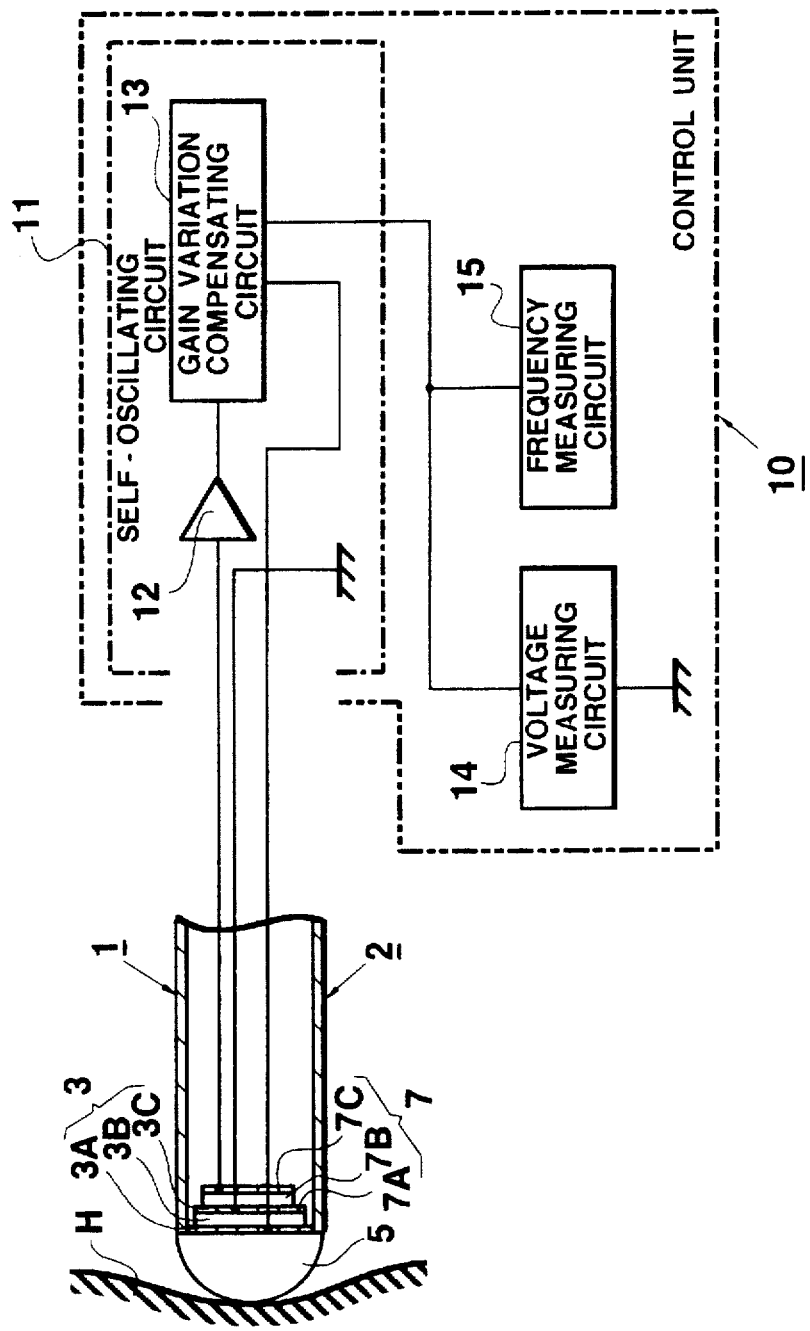
FIG. 13 shows the overall structure of a hardness measuring apparatus according to Modification 3 of Embodiment 1.

FIG. 13 shows the overall structure of a hardness measuring apparatus according to Modification 3 of Embodiment 1. This hardness measuring apparatus includes a cylindrical-shaped casing 2 of a hand piece 1. A hemispherical tip of a contact element 5 fits into an end of the casing 2. An oscillator 3 is disposed on a flat surface of the contact element 5 facing toward the casing 2, and then a detecting element 7 is disposed on the oscillator 3. The oscillator 3 comprises a first electrode 3A used as an anode, a second electrode 3C used as a cathode and a piezoelectric crystal 3B formed between the first and second electrodes 3A and 3C, as in the hardness measuring apparatus shown in FIG. 1. A detecting element 7 comprises a first electrode 7A used as a cathode, a second electrode 7C used as an anode and a piezoelectric crystal 7B formed between the first and second electrodes 7A and 7C. Each layer of these first electrode 3A, piezoelectric crystal 3B, second electrode 3C, first electrode 7A, piezoelectric crystal 7B and second electrode 7C can be easily fabricated with a fine pattern by a film fabricating method, such as sputtering used in semiconductor production. The sequence of the layers of the oscillator 3 and detecting element 7 can be reversed. Alternatively, the oscillator 3 can be easily made by laminating a sheet-formed piezoelectric material, such as piezoelectric ceramic or oscillating quartz, with adhesive.

A hardness measuring apparatus having such a structure includes the hemi-spherical contact element 5. The oscillator 3 and detecting element 7 are directly fabricated on the flat surface of the contact element facing toward the casing 2 as an integrated assembly. The mechanical oscillation part of the electromechanical oscillation system, which is in contact with a subject H, can be significantly reduced in size and weight. When a semiconductor producing technique is used for fabricating the oscillator 3 and detecting element 7, the measuring section can be fabricated in a small size, enabling the hardness measuring apparatus to be used for measuring the hardness of a small subject, such as a biological tissue.

In a hardness measuring apparatus according to this embodiment, the contact element 5 and oscillator 3 can be formed as an integrated assembly. In this structure, the oscillation of the oscillator 3 is directly conducted to a subject H. In addition, the feedback loop of a phase-lock loop (PLL) circuit can be used instead of the feedback loop of the self-oscillating circuit 11.

Embodiment 2

In Embodiment 2, a hardness measuring apparatus for measuring the hardness of a biological tissue in a human living body, in which a frequency deviation circuit is used, will be described.

[System Structure of a Hardness Measuring Apparatus for Palpation of Internal Organs]

Figure 14:
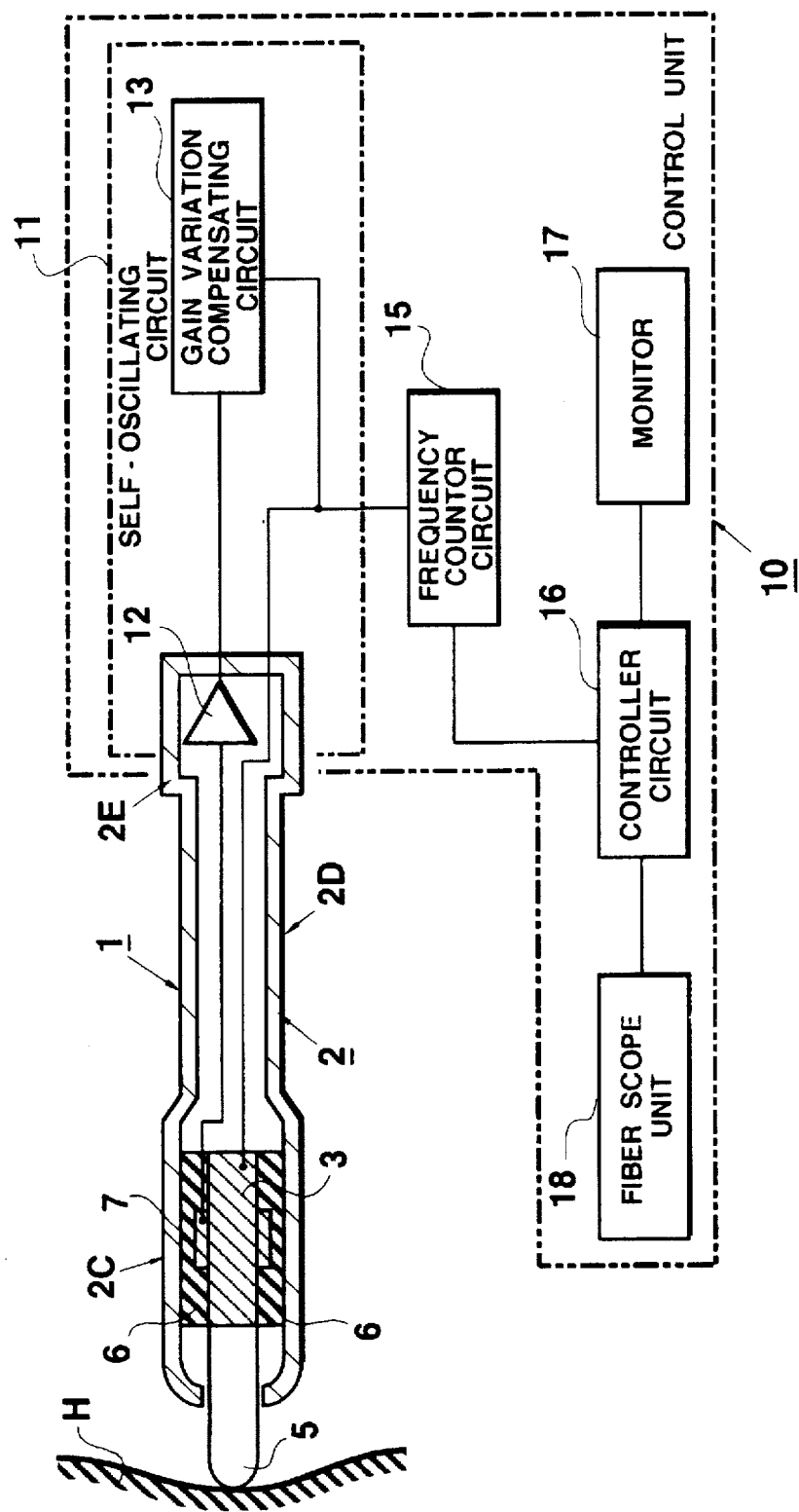
FIG. 14 shows the overall structure of a hardness measuring apparatus for palpation of internal organs according to Embodiment 2.

FIG. 14 shows the overall structure of a hardness measuring apparatus for palpation of internal organs according to Embodiment 2. The hardness measuring apparatus has a main probe 1 used for palpation of internal organs and a control unit 10 placed outside the main probe 1. The main probe 1 of the hardness measuring apparatus for palpation of internal organs has a casing 2, which is formed by a tubular pipe insertable into a living body (for example, a human body). The casing 2 has a touch section 2C which is brought into contact with a subject H (living body), a middle section in its middle portion and a hold section 2E held by a person carrying out the measurement. The outer diameters of the touch and hold sections 2C and 2E are a little larger than that of the middle section 2D. Since the casing 2 is inserted into a living body, it is made of a highly rigid and corrosion resistive material, such as stainless steel.

An oscillator 3 for generating ultrasonic oscillation and a detecting element 7 for detecting oscillation are disposed inside the touch section 2C of the casing 2. The oscillator 3 comprises a piezoelectric ceramic oscillator, as in the hardness measuring apparatus according to Embodiment 1. The oscillator 3 is brought into contact with a subject H of a biological tissue in a living body. A contact element 5 (touch member) is mechanically coupled with the subject H whose hardness is to be measured. The tip of the contact element 5 sticks out from an opening formed at the end of the touch section 2C of the casing 2. The tip of the contact element has a hemi-spherical shape. Therefore, the contact element 5 is widely usable for contacting with a subject H both at a point and over an area. The detecting element 7 is fixed on the oscillator 3, and detects the oscillation of the oscillator 3. The detecting element 7 comprises piezoelectric ceramics, as the oscillator 3. The detecting element 7 is integrated with the oscillator 3, as in the hardness measuring apparatus according to embodiment 1. Alternatively, the detecting element 7 can be separately fabricated, and then mechanically coupled with the oscillator 3.

Inside the touch section 2C of the casing, an elastic member 6 is disposed between the inner surface of the touch section 2C and oscillator 3, or detecting element 7. The elastic member 6 retains the electromechanical oscillation system comprising the oscillator 3, detecting element 7 and contact element 5, and absorbs the oscillation generated by the electromechanical oscillation system and proceeding toward the casing 2. The elastic member 6 is made of silicone rubber. Any oscillation absorbing material or urethane resin, fluororubber or nitrile rubber (NBR) can be used as the elastic member 6.

The control unit 10 has a self-oscillating circuit 11, a gain variation compensating circuit 13, a frequency counter circuit 15, a controller circuit 16, a monitor 17 and a fiberscope unit 18. The self-oscillating circuit 11 of the control unit 10 has an amplifying circuit 12. The amplifying circuit 12 is disposed inside the hold section in a hardness measuring apparatus for palpation of internal organs according to this embodiment. The input terminal of the amplifying circuit 12 is connected to the output terminal of the detecting element 7. The output terminal is connected to the input terminal of the oscillator 3 via the gain variation compensating circuit 13. The amplifying circuit 12 amplifies oscillation information outputted from the detecting element 7. The amplified oscillation information is fed back to the oscillator 3 to form a feedback loop. The mechanical oscillation system comprising the oscillator 3, detecting element 7 and contact element 5, and the electrical oscillation system comprising the self-oscillating circuit 11 form an electromechanical oscillation system. In this electromechanical oscillation system, the self-oscillating circuit 11 oscillates the oscillator 3 in a resonant state, and the oscillator 3 oscillates the contact element 5. When the contact element 5 is brought into contact with a subject H, the mechanical or acoustic impedance of the subject H changes the oscillation mode of the oscillator 3. This causes a change in the frequency characteristic of the electromechanical oscillation system. The hardness of the subject H can be determined by the change in the frequency characteristic.

The gain variation compensating circuit 13 is connected between the amplifying circuit 12 and oscillator 3. The gain variation compensating circuit 13 has a gain increasing function of increasing the gain in response to a change in the frequency characteristic of the electromechanical oscillation system according to a principle of basic operation similar to that of the hardness measuring apparatus according to Embodiment 1. The gain variation compensating circuit 13 also has a phase transfer function of adjusting the difference between the input and output phases (phase difference) of the self-oscillating circuit 11, and of promoting feedback oscillation.

The input terminal of the frequency counter circuit 15 is connected to the output terminal of the gain variation compensating circuit 13. The frequency counter circuit measures the frequency of the electromechanical oscillation system.

The input terminal of the controller circuit 16 is connected to the output terminal of the frequency counter circuit 15. The controller circuit 16 generates an image. The frequency counter circuit 15 measures the difference between the frequencies of the electromechanical oscillation system before and after the contact element 5 in a resonant state becomes in contact with a subject H. The controller circuit 16 detects the difference in the frequency of the electromechanical oscillation system from the data measured by the frequency counter circuit 15. Hardness information representing the mechanical property of the subject H is obtained in the controller circuit 16.

Figure 15:
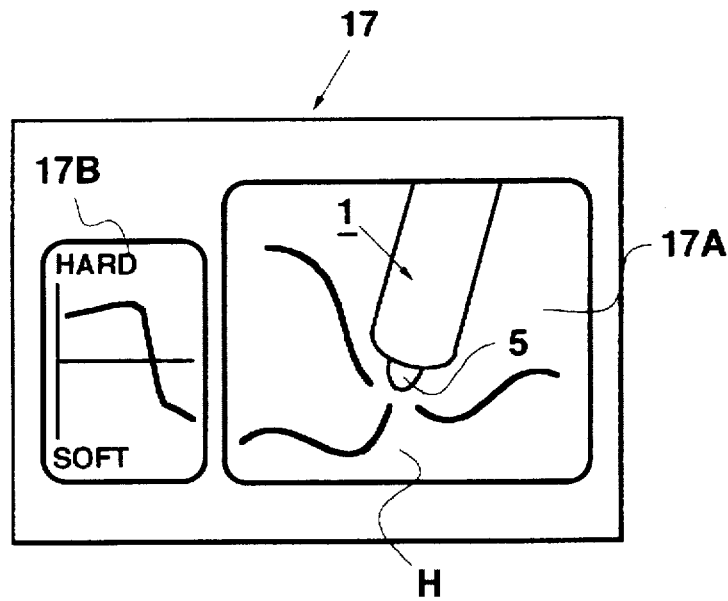
FIG. 15 shows an image displayed on a monitor.
Figure 16:
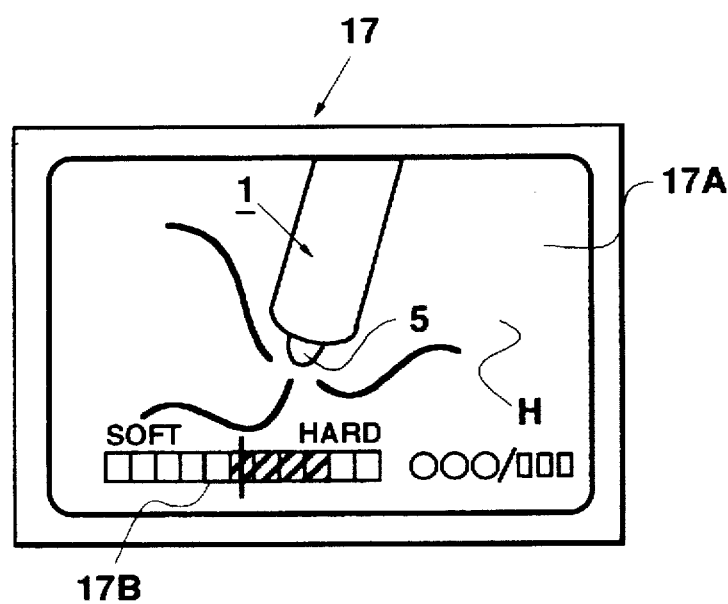
FIG. 16 shows an image displayed on a monitor.

The fiberscope unit 18 and monitor 17 are connected to the controller circuit 16. The fiberscope unit 18 images a location whose hardness is to be measured. Obtained image data (image data generated by endoscopic image or observation image) are outputted to the controller circuit 16. In a hardness measuring apparatus for palpation of internal organs according to Embodiment 2, an endoscope is used as the fiberscope unit 18. The monitor 17 combines the image data from the fiberscope unit 18 and hardness information based on the measured data from frequency counter circuit 15. The monitor 17 displays the combined hardness information as an image. FIG. 15 shows an image displayed on the monitor 17. In a hardness measuring apparatus for palpation of internal organs according to this embodiment, the screen of the monitor 17 is divided into two areas 17A and 17B, one is an endoscopic image display area 17A, the other is a hardness information display area 17B. In the endoscopic image display area 17A, an endoscopic image taken by the fiberscope unit 18 is displayed. As shown in FIG. 15, an image showing that the main probe 1 is in contact with a subject H is displayed in the endoscopic image display area 17A. In the hardness information display area 17B, a graph representing the hardness of the subject H is displayed. FIG. 16 shows another image displayed in the monitor 17. As shown in FIG. 16, the monitor 17 has the endoscopic image display area 17A and hardness information display area 17B, and a specific part of the endoscopic image display area 17A (for example, a lower-left part) overlaps the hardness information display area 17B.

Figure 17:
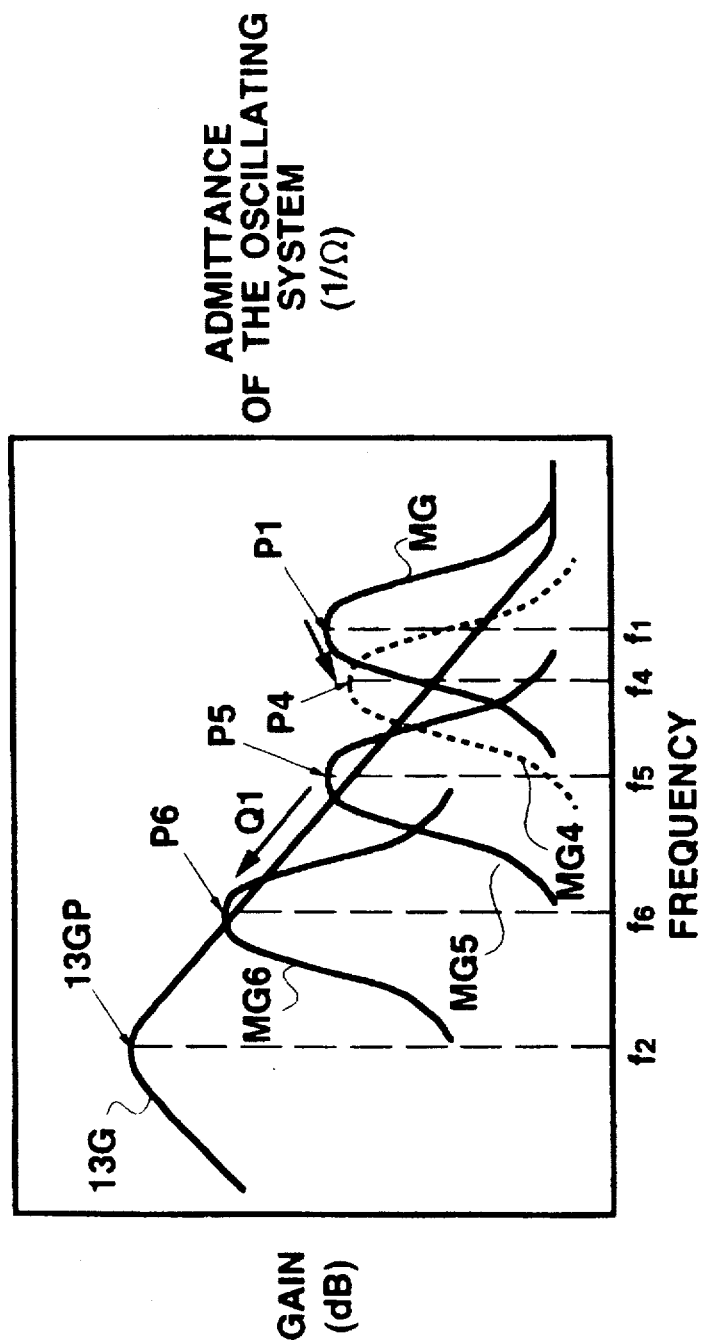
FIG. 17 shows gain-frequency and admittance-frequency characteristic curves.

FIG. 17 shows gain-frequency and admittance-frequency characteristic curves of the electromechanical oscillation system and gain variation compensating circuit 13. In FIG. 17, the horizontal axis indicates frequency, and vertical axes respectively indicate gain and admittance of the oscillation system. The characteristic curve MG shows a gain-frequency characteristic (admittance-frequency characteristic) of the electromechanical oscillation system excepting the gain variation compensating circuit 13 when the contact element 5 is not in contact with a subject H. The characteristic curve 13G shows a gain-frequency characteristic of the gain variation compensating circuit 13. In the gain variation compensating circuit 13 of a hardness measuring apparatus for palpation of internal organs according to Embodiment 2, a band-pass filter circuit is used, as in a hardness measuring apparatus according to Embodiment 1. The gain-frequency characteristic curve 13G of the gain variation compensating circuit 13 is set in a frequency band in which the gain of the electromechanical oscillation system is changed in response to a change in the frequency. A central frequency $f_2$, at which the gain has a maximum value 13GP in the gain-frequency characteristic curve 13G of the gain variation compensating circuit 13, is lower than a central frequency $f_1$ at which the gain in the characteristic curve MG of the electromechanical oscillation system has a maximum value P1 (maximum value of the admittance).

Therefore, the electromechanical oscillation system resonantly oscillates at a frequency lower than the central frequency $f_1$, and higher than the central frequency $f_2$, when the contact element 5 is in contact with subject H.

When the contact element 5 of the main probe 1 is brought into contact with a soft subject with an area the gain-frequency characteristic curve MG of the electromechanical oscillation system is changed to a gain-frequency characteristic curve MG4 in a conventional hardness measurement apparatus without the gain variation compensating circuit 13. In the gain-frequency characteristic curve MG4, because the acoustic impedance is low, the resonance frequency $f_4$ at which the gain has the maximum value P4 is lowered, and the gain is also decreased. Such a phenomenon has been reported by S. Omata in "Development of piezoelectric transducer for measuring contact compliance of a soft body" Iyodenshi to Seitaikogaku (Journal of the Japan Society of Medical Electronics and Biological Engineering), Vol. 24, No. 5, pp. 38–42 (1986).

A hardness measuring apparatus for palpation of internal organs according to Embodiment 2 has a characteristic shown by a gain-frequency characteristic curve MG5, when the contact element 5 of the main probe 1 is not in contact with anything. The gain-frequency characteristic curve MG5 has a maximum value P5 at a central frequency $f_5$. When bringing the contact element 5 into contact with a subject H having an area, the gain-frequency characteristic curve MG5 is changed to a gain-frequency characteristic curve MG6. Because the acoustic impedance of the subject H is low, the central frequency $f_5$ is shifted toward a lower frequency, and becomes stable at a frequency f6. The gain is increased along the gain-frequency characteristic curve 13G of the gain variation compensating circuit 13 by the gain increasing and phase transfer functions of the gain variation compensating circuit 13, leading to the obtaining of a maximum value P5 of the gain. This increased gain enables a sufficient detection voltage for hardness measurement to be obtained.

[Use of a Hardness Measuring Apparatus for Palpation of Internal Organs]

Figure 18:
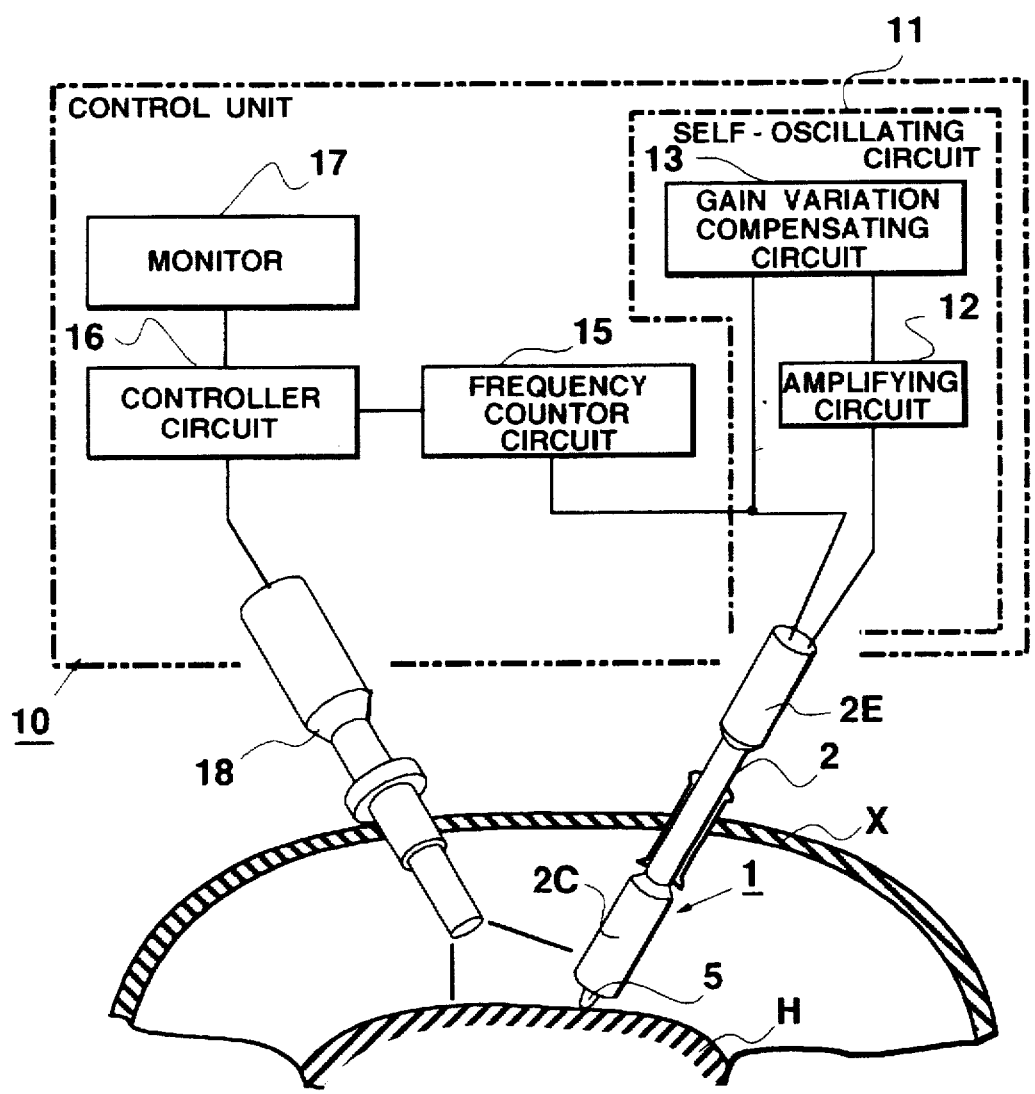
FIG. 18 shows the system structure of a hardness measuring apparatus for palpation of internal organs according to Embodiment 2.

The use of a hardness measuring apparatus for palpation of internal organs according to this embodiment will be described. A lung in a human thoracic cavity is used as a subject, and its hardness is measured for medical investigation. FIG. 18 shows the system structure of a hardness measuring apparatus for palpation of internal organs according to this embodiment. The fiberscope unit 18 is inserted into the thoracic cavity X of a human body (subject) through an opening formed on the surface of a thoracic part. The fiberscope unit 18 sends an endoscopic image in the thoracic cavity to the controller circuit 16 as image data, the controller circuit 16 generates an endoscopic image, which is displayed in the endoscopic image display area 17A of the monitor 17. A person carrying out the measurements can observe the endoscopic image in a field of view by looking at the endoscopic image displayed in the endoscopic image display area 17A of the monitor 17.

Another opening is formed on the surface of the thoracic part of the subject. A probe guide 19 is inserted through the opening. The main probe 1 of the hardness measuring apparatus for palpation of internal organs is inserted into the thoracic cavity X via the probe guide 19. The measurer contacts the contact element 5 disposed at the tip of the main probe 1 inserted into the thoracic cavity with the objective subject H (lung) in the human body, while observing the endoscopic image display area 17A of the monitor 17. In the endoscopic image display area 17A, an endoscopic image showing that the contact element 5 is in contact with the objective subject H can be observed. Using a hardness measuring apparatus for palpation of internal organs according to this embodiment, at the instant the contact element 5 is brought into contact with a subject H, the hardness of the subject H can be measured from a change in the frequency of the electromechanical oscillation system. A result of this, a hardness measurement is displayed in the hardness information display area 17B of the monitor as hardness information.

Figure 19:
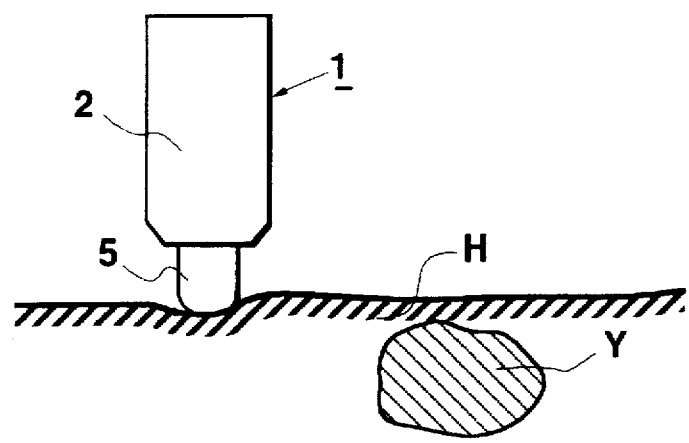
FIG. 19 shows a cross-sectional view of a biological tissue (subject) for explaining the operation of a main probe.
Figure 20:
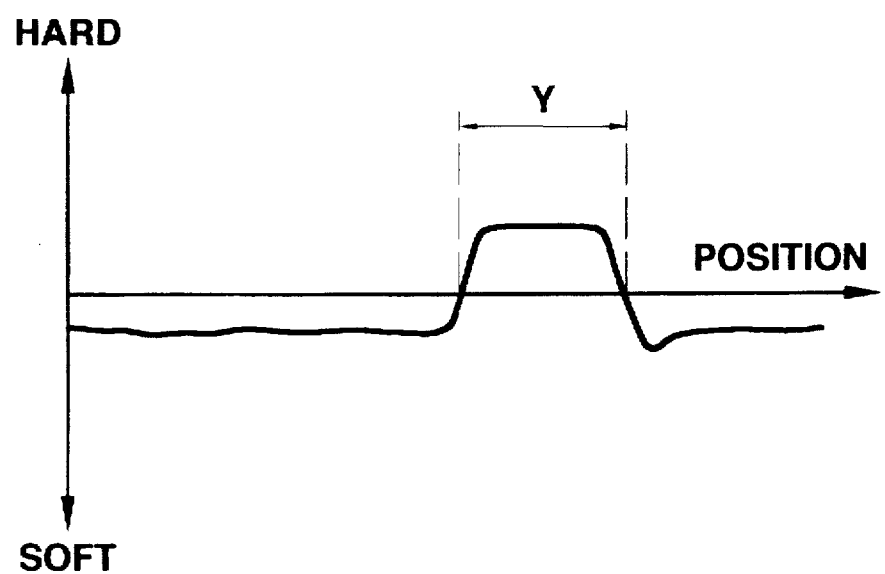
FIG. 20 shows a magnified view of a hardness information display area.

FIG. 19 shows a cross-sectional view of a biological tissue (subject H) for explaining the operation of the main probe 1. FIG. 20 shows a magnified view of the hardness information display area 17B representing the hardness information corresponding to a cross-section of a biological tissue. As shown in FIG. 19, the contact element 5 of the main probe is slid in the direction indicated by the arrow, keeping contact with the subject H. The hardness measuring apparatus for palpation of internal organs measures the hardness of the subject H in the range of the sliding. When a tumor Y such as a cancer exists on the surface of a lung (subject H) or in a deeper part of a pulmonary tissue, the tissue is usually harder than a normal pulmonary tissue. Therefore, when the contact element 5 of the main probe 1 moves from a normal tissue to the tumor, the hardness of the subject H shown in the hardness information display area 17B increases, as shown in FIG. 20. The tumor Y located in the pulmonary tissue can be detected, and its position can also be identified.

A hardness measuring apparatus for palpation of internal organs can be used for measuring the hardness of a liver (for example, a liver suffering from cirrhosis) or a muscle tissue. The biological tissue in a living body to which the hardness measuring apparatus for palpation of internal organs is applied is not limited. In addition, a hardness measuring apparatus for palpation of internal organs can be used for measuring the hardness of animal or plant tissues.

As a hardness measuring apparatus according to Embodiment 1, a hardness measuring apparatus for palpation of internal organs has the gain variation compensating circuit 13. The gain increasing and phase transfer functions of the gain variation compensating circuit 13 increases the gain in response to a change in the frequency. This enables a sufficient detection voltage for hardness measurement to be obtained. A slight difference in the hardness of a subject can be detected to precisely determine the hardness. When the hardness of different materials, which have similar hardnesses resulting in similar resonance frequencies, is measured, the phase transfer function of the gain variation compensating circuit 13 changes the frequency, and increases the gain until a slight difference between the phases becomes zero, where the feedback oscillation is stably carried out. This enables a sufficient detection voltage for hardness measurement to be obtained. When the hardness of various soft and hard subjects H is measured, the frequency is changed, a variation in the frequency is enhanced, and then the gain is increased in response to the enhanced variation in the frequency. This enables a detection voltage sufficient for hardness measurement to be obtained. Therefore, the hardness of various soft and hard subjects can be measured in a wide range of hardness. In this hardness measuring apparatus, the effective resonance frequency band of the electromechanical oscillation system is widened, and the hardness of various soft and hard subjects H can be measured.

In a hardness measuring apparatus for palpation of internal organs, the gain variation compensating circuit 13 can be easily realized by a filter circuit comprising a simple combination of resistance elements and capacitance elements. This does not require a complicated circuit structure, enabling the system to be simple and fabricated with low cost.

A hardness measuring apparatus for palpation of internal organs according to this embodiment can detect a tumor Y located on the surface or at a deeper position of a biological tissue by bringing the contact element 5 of the main probe 1 inserted into a living body into contact with a biological tissue (subject H) in the living body, and identifying the position of the tumor Y. Therefore, medical diagnosis of a disease, such as cancer, a tumor or cirrhosis, can be easily carried out. In addition, when a physician cannot directly touch an affected part of a biological tissue, the hardness measuring apparatus for palpation of internal organs easily realizes palpation similar to that conducted by a physician with high accuracy. This enables an early prophylaxis.

Since a hardness measuring apparatus for palpation of internal organs according to this embodiment has the endoscopic image display area 17A and hardness information display area 17b in the monitor 17 of the control unit 10, the contact of the main probe 1 with a biological tissue (subject H) in a living body is confirmed by an endoscopic image displayed in the endoscopic image display area 17A. At the same time, measurement of the hardness (diagnosis) of the biological tissue can be carried out. This always enables the measurement of hardness to be performed at a correct location safely and with high efficiency.

[Application of a Hardness Measuring Apparatus for Palpation of Internal Organs]

The hardness measuring apparatus for palpation of internal organs according to Embodiment 2 can be used for measuring the hardness of a biological tissue located not only within a living body, but also that located on the surface of the living body, such as skin, as a hardness measuring apparatus for ectal organs. The hardness of an ectal biological tissue (subject H), such as skin, which is treated with an electrical cautery, laser treatment device or microwave treatment device can be measured by this hardness measuring apparatus for ectal organs. The postoperative healing of the treated tissue can be easily monitored by continuously measuring the hardness of the treated tissue.

In both hardness measuring apparatus for palpation of internal organs and hardness measuring apparatus for ectal organs according to this embodiment, a layered piezoelectric ceramic oscillator, bimorph oscillator, quartz oscillator, PVDF-based oscillator, magnetostrictive element or SAW element can be used as the oscillator 3 instead of the piezoelectric ceramic oscillator, as in a hardness measuring apparatus according to Embodiment 1. A layered piezoelectric ceramic oscillator, bimorph oscillator, quartz oscillator, PVDF-based oscillator, magnetostrictive element or SAW element can also be used as the detecting element 7. A low-pass filter circuit, high-pass filter circuit, notch filter circuit, integrating circuit, differentiating circuit or peaking amplifying circuit can be used as the gain variation compensating circuit 13. In addition, an active filter circuit or passive filter circuit can be used as the gain variation compensating circuit 13.

[Modification 1]

Figure 21:
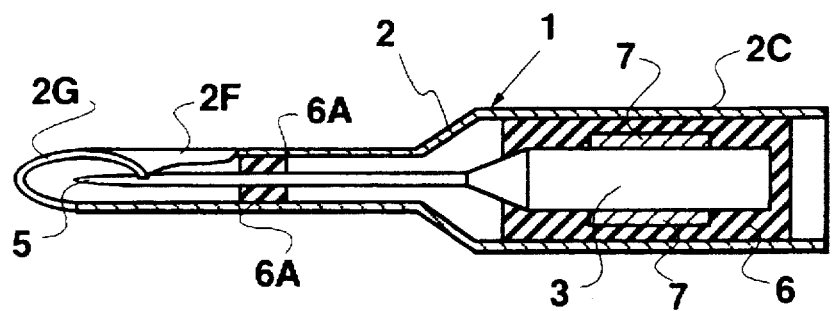
FIG. 21 shows a partial cross-sectional view of the tip of a main probe.

In a hardness measuring apparatus for palpation of internal organs according to Modification 1 of Embodiment 2, a main probe 1 is used instead of the hand piece 1. The shape of the tip of the main probe 1 and that of the contact element 5 are changed. FIG. 21 shows a partial cross-sectional view of the tip of the main probe 1 of a hardness measuring apparatus for palpation of internal organs. The contact element 5 of the hardness measuring apparatus for palpation of internal organs is formed as a contact needle that can puncture a biological tissue. An outer needle 2F having a lumen is formed surrounding the contact needle 5 of the main probe 1, which is to be brought into contact with a subject H, in order to protect the contact needle 5. A puncture edge 2G is formed at the tip of the outer needle 2F by cutting at a sharp angle to the longitudinal axis, and can puncture a biological tissue in a living body. Only the tip of the contact needle 5 (contact element) sticks out of the puncture edge 2G of the outer needle 2F. The contact element 5 is disposed inside the outer needle 2F except its tip, which can be brought into contact with a subject H (biological tissue).

Figure 22:
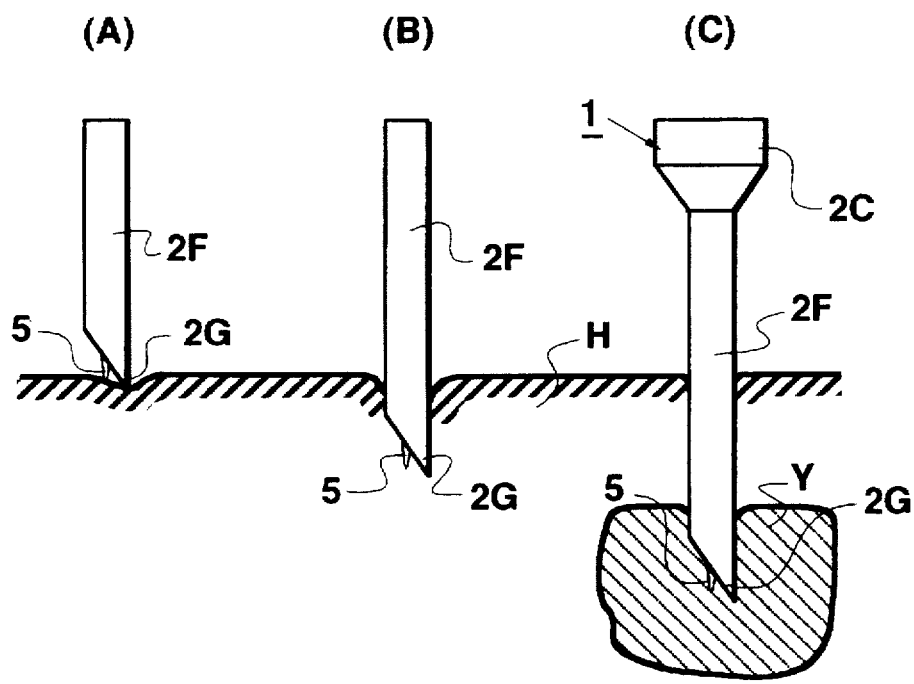
FIG. 22 shows cross-sectional views of a main probe and the main part of a subject in the respective steps of palpation.

A supporting member 6A is disposed in a middle portion of the lumen of the outer needle 2F. The contact element 5 is held at the central axis of the outer needle 2F by the supporting member 6A, and prevents the contact element 5 from coming into contact with the outer needle 2F. The supporting member 6A blocks the inside of the outer needle 2F in order to prevent an unnecessary substance from entering the inside of the main probe 1. The supporting member 6A is disposed so that it is a node of the resonance oscillation of the electromechanical system, as it is disposed between the oscillator 3, and detecting element 7 and the casing 2. This enables the oscillation not to be conducted to the casing 2, such as the outer needle 2F, and only the contact element is oscillated. In this hardness measuring apparatus for palpation of internal organs, the overall structure is the same as that according to Embodiment 2 described before, except for the contact element 5, outer needle 2F, puncture edge 2G and supporting member 6A. The hardness measuring apparatus for palpation of internal organs will be described. FIG. 22 shows cross-sectional views of the main probe 1 and the main part of a subject H (biological tissue) in the respective steps of palpation. In the hardness measuring apparatus for palpation of internal organs, the hardness of the subject H (biological tissue) is measured according to the sequence of the steps (A), (B) and (C). The outer needle 2F of the main probe 1 punctures the subject H (biological tissue) from the surface a living body, and then the hardness of the subject is measured. Since the outer needle 2F has the puncture edge 2G at its tip, puncture of the biological tissue is smoothly carried out. In a hardness measuring apparatus for palpation of internal organs according to Modification I of Embodiment 2, the contact element 5 (contact needle) is placed inside the outer needle 2F, and the hardness of a part of the biological tissue in contact with it is measured. The step (C) shows that the contact element 5 reaches a tumor Y located in a deeper part of the biological tissue. As in the hardness measuring apparatus for palpation of internal organs according to Embodiment 2, when the hardness of a biological tissue in contact with the contact element 5 is changed, the frequency of the electromechanical oscillation system is changed. The gain variation compensating circuit 13 increases the gain in response to the change in the frequency of the electromechanical oscillation system, leading to the obtaining of a sufficient detection voltage for measuring the hardness of the biological tissue. The hardness of the biological tissue is finally displayed in the hardness information display area 17B of the monitor 17 as a graph.

Figure 23:
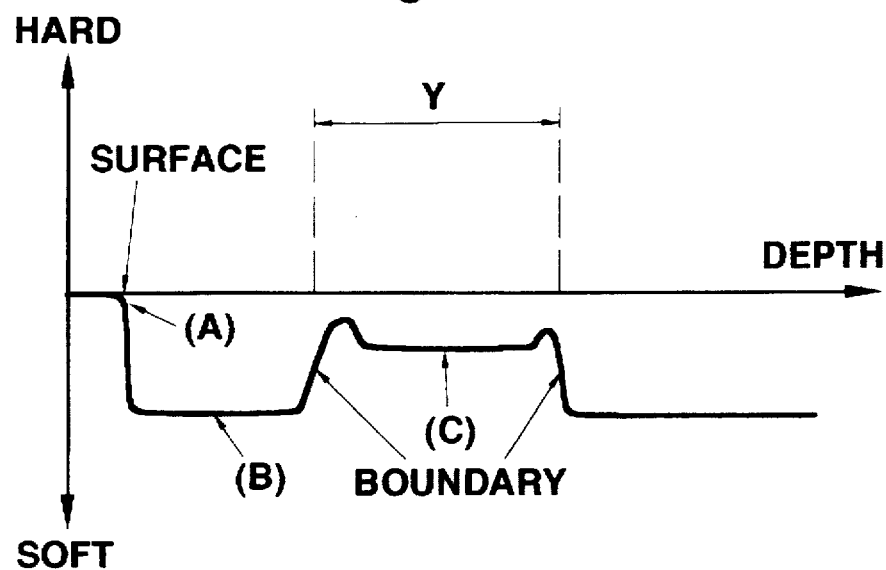
FIG. 23 shows a graph displayed in a hardness information display area.

FIG. 23 shows a graph displayed in the hardness information display area 17B of the monitor 17. The vertical axis rep resents the hardness of a subject H (biological tissue), and the horizontal axis the depth of the subject H from the surface of a living body. In the step (A) in which the puncture edge 2G of the outer needle 2F has just begun to puncture, the surface of the biological tissue is pressed by the outer needle 2F and elongated. This makes the surface harder. Since the contact element 5 is in contact with the hardened surface, an increased hardness is measured. In the step (B) during which the puncture of the outer needle 2F into the subject H proceeds, the contact element 5 stays in contact with an internal tissue. A constant and small hardness is measured during this step. In the step (C), the contact element 5 reaches a tumor Y and is further inserted into it. As in the step (A), at the boundary between the tumor Y and normal tissue, the puncture edge 2G of the outer needle 2F presses the surface of the tumor Y, which is elongated. This makes the surface harder. Since the contact element 5 is in contact with the hardened surface, an increased hardness is measured. After that, the contact element 5 further proceeds into the tumor Y. A constant hardness larger than that measured for the normal tissue is measured. The hardness of the tumor Y is slightly larger than that of the surrounding normal tissue. The difference between these hardnesses can be surely detected by a hardness measuring apparatus for palpation of internal organs according to Embodiment 2.

The contact of the outer needle 2F of the main probe 1 with a biological tissue (subject H) is monitored by observing an endoscopic image which is sent from the fiberscope unit 18 and displayed in the endoscopic image display area 17A of the monitor 17 (see FIGS. 14, 15 and 18), for example, when puncturing a biological tissue located on the surface of a lung with the outer needle 2F. The puncture position of the outer needle 2F on the surface of a lung is displayed in the endoscopic image display area 17A. The hardness of the lung in the depth direction at the puncture position can be measured while observing the puncture region. Therefore, a tumor Y can be surely detected and both the position and depth of the tumor Y can be identified.

In such a hardness measuring apparatus for palpation of internal organs, a contact needle is used as the contact element 5 of the main probe 1, and it is surrounded by the outer needle 2F having the puncture edge 2G at the tip. This enables the contact element 5 to puncture a deeper part of a biological tissue. Hardness information of the deeper part of a biological tissue can be directly obtained. As described before, the hardness measuring apparatus for palpation of internal organs according to Embodiment 2 can obtain a sufficient detection voltage for measuring the hardness of a biological tissue, even when the difference between the hardnesses is slight. The hardness of a deeper part of a biological tissue can be directly measured by the contact element 5, enabling an affected part of a biological tissue to be detected with high accuracy. This realizes an effective medical prophylaxis.

In a hardness measuring apparatus for palpation of internal organs according to this embodiment, the monitor 17 has the two endoscopic image display area 17A and hardness information display area 17B. An actual contact position, at which the contact element 5 is in contact with a biological tissue via the outer needle 2F, can be confirmed by observing an endoscopic image displayed in the endoscopic image display area 17A. While observing the endoscopic image, the hardness of a biological tissue, in particular that of a deeper part of the biological tissue, can be measured. This enables a diagnosis of a biological tissue at a correct position safely and with high efficiency.

A hardness measuring apparatus for palpation of internal organs according to Embodiment 2 is not restrictively used for measuring the hardness of a lung or liver as described before, but can be also used for measuring the hardness of a living tissue of a thyroid gland. When the hardness of a living tissue of a thyroid gland is measured, the outer needle 2F is inserted toward the thyroid gland with puncture, and the contact element is brought into contact with a thyroid gland tissue. When the contact element 5 is in contact with the thyroid gland tissue, hardness information of the thyroid gland tissue is displayed in the hardness information display area 17B of the monitor 17. In measurement of the hardness of a thyroid gland tissue, the fiberscope unit is not needed.

[Modification 2]

Figure 24:
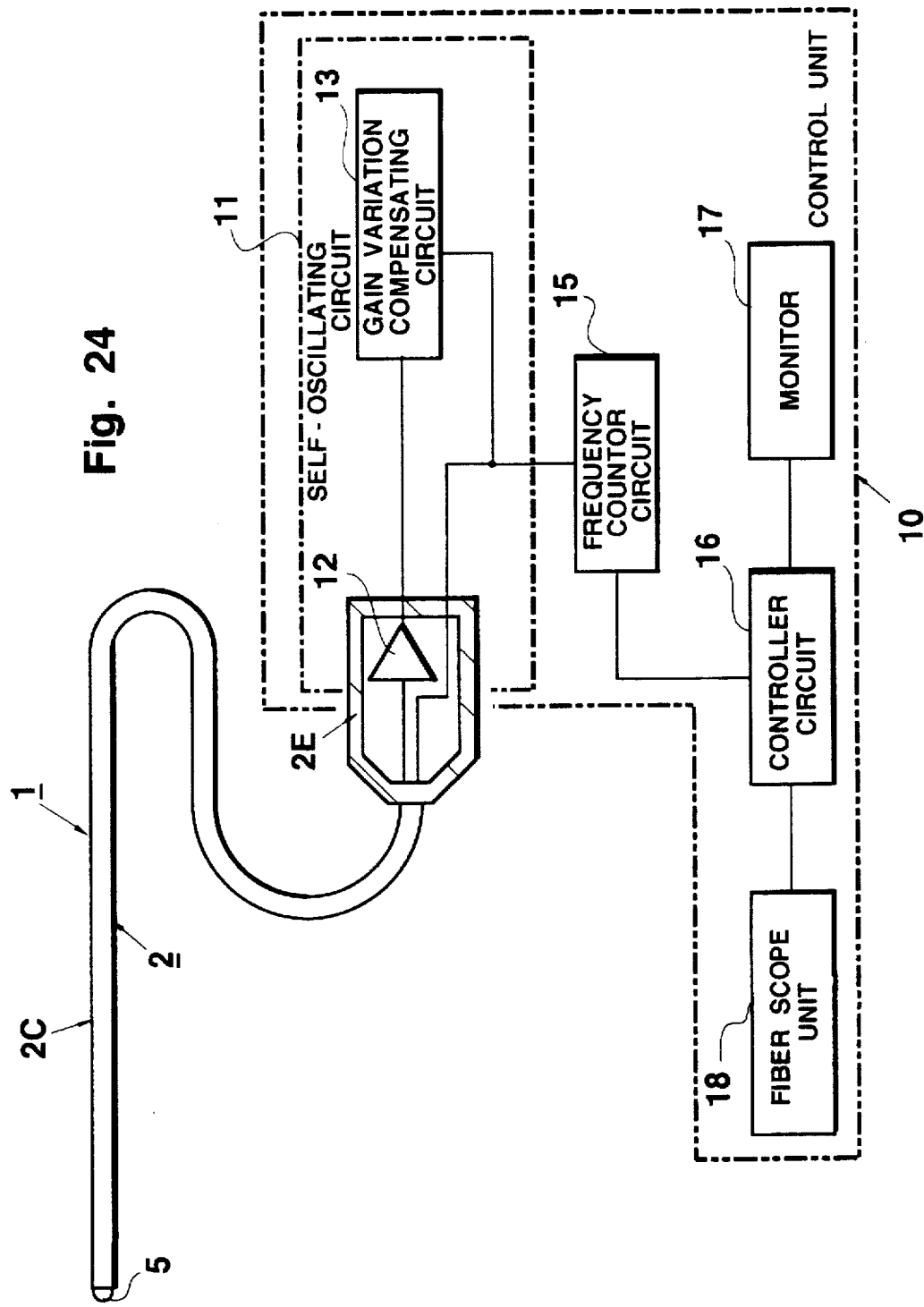
FIG. 24 shows the overall structure of a hardness measuring apparatus for palpation of internal organs according to Modification 2 of Embodiment 2.

A hardness measuring apparatus for palpation of internal organs according to Modification 2 of Embodiment 2 is the same as one described in Modification 1 except that a soft main probe 1 used instead of the main probe 1. FIG. 24 shows the overall structure of a hardness measuring apparatus for palpation of internal organs according to Modification 2 of Embodiment 2. This hardness measuring apparatus for palpation of internal organs has a soft main probe 1 insertable into a cavity in a human body. The touch section 2C of the soft main probe 1 is formed by a flexible (soft) tube which can be inserted into a cavity. A fluororesin tube is used as the flexible tube. A polyvinyl chloride tube, polyurethane tube or coil sheath tube can be used as the flexible tube.

Figure 25:
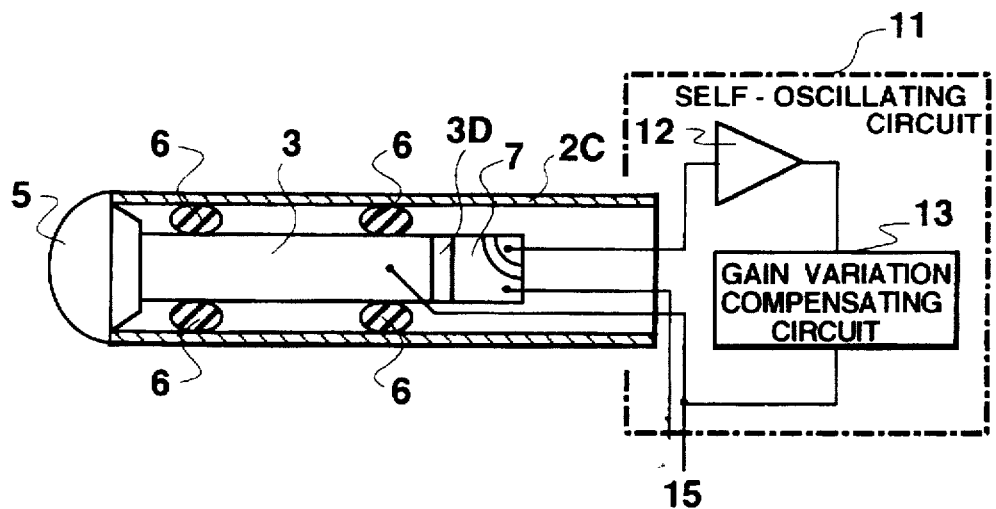
FIG. 25 shows a magnified cross-sectional view of a touch section of a soft main probe.

The soft main probe basically has the touch section 2C and holding section 2E. The amplifying circuit 12 of the self-oscillating circuit 11 is disposed inside the holding section 2E, as in the hardness measuring apparatus for palpation of internal organs according to Embodiment 2. FIG. 25 shows a magnified cross-sectional view of the touch section 2C of the soft main probe 1. In the touch section 2C formed by a soft tube, the oscillator 3 for generating ultrasonic oscillation is disposed at the tip facing a subject H on the central axis of the soft tube. The contact element 5 to be brought into contact with the subject H is placed at the tip of the touch section 2C. The contact element 5 has a hemi-spherical shape, and sticks out from the tip toward the subject H. The contact element 5 is coupled with the oscillator 3, and the ultrasonic oscillation of the oscillator 3 is conducted to the contact element 5.

The oscillator 3 is connected to the detecting element 7 detecting the oscillation of the oscillator 3. The detecting element 7 is connected to the amplifying circuit 12 of self-oscillating circuit 11 placed inside the holding section 2E of the soft main probe 1.

In the touch section 2C formed by a soft tube, the supporting member 6 for supporting the electromechanical oscillation system including the oscillator 3, detecting element 7 and contact element 5 is placed. As in the hardness measuring apparatus for palpation of internal organs according to Embodiment 2, the supporting member 6 holds the electromechanical oscillation system at the axial center of the touch section 2C, and prevents the oscillation of the mechanical oscillation system from being conducted to the touch section 2C. In the hardness measuring apparatus for palpation of internal organs described here, a round ring-shaped supporting member is used as the supporting member 6. The contact areas between the oscillator 3 and supporting member 6, and the supporting member 6 and the inner surface of the touch section 2C are set smaller. The oscillator 3 is fairly flexibly supported to enable it to follow the bending of the touch section 2C to some extent. This keeps the oscillator 3 from being excessively pressed and adversely affected from outside. The supporting member 6 is made of a rubber material, such as silicone rubber or NBR, or of a resin material, such as polyurethane resin or fluororesin.

Figure 26:
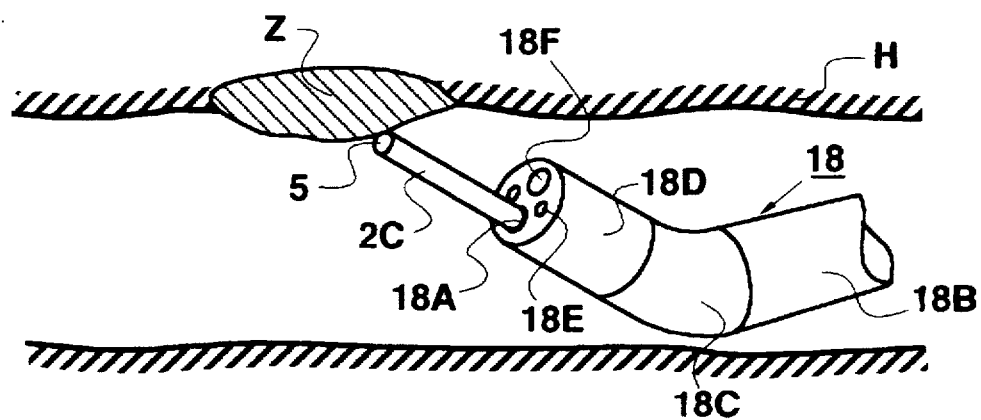
FIG. 26 shows a cross-sectional view of a fiberscope unit and a biological tissue.

FIG. 26 shows a cross-sectional view of the fiberscope unit 18 having the soft main probe 1 and a biological tissue into which the fiberscope unit 18 is inserted. The touch section 2C of the hardness measuring apparatus for palpation of internal organs, formed by a soft tube, is inserted into an instrument guide channel 18A of the fiberscope unit 18, and introduced to a cavity through the instrument guide channel 18A. A fiberscope unit having a flexible structure, such as a digestive tract videoscope or digestive tract fiberscope, is used as the fiberscope 18. The fiberscope unit 18 has an insertion section 18B which can be inserted into a cavity. A tip section 18D is coupled with the tip of the insertion section 18B facing the cavity via a flexible tube section 18C. The flexible tube section 18C connects the insertion section 18B and tip section 18D, and permits the tip section 18D to freely turn around the insertion section 18B. The end surface of the tip section 18D has an exit of the instrument guide channel 18A, an illumination window 18E of a light guide for introducing illumination light and an observation window 18F coupled with observation optics. The touch section 2C of the soft main probe 1 is formed by a soft tube, and has such an outer diameter that it can be inserted into the instrument guide channel 18A of the fiberscope unit 18 having a flexible structure.

The structure of this hardness measuring apparatus for palpation of internal organs is the same as that of the hardness measuring apparatus for palpation of internal organs according to Embodiment 2 except for the soft main probe and fiberscope unit 18 having a soft structure.

The use of this hardness measuring apparatus for palpation of internal organs will be described. The hardness of the inner surface (subject H) of an esophagus suffering from esophageal varices is measured by this hardness measuring apparatus for palpation of internal organs. As shown in FIG. 26, the insertion section 18B of the soft fiberscope unit 18 is inserted into the esophagus of a patient from his mouth. The inner surface of the esophagus is observed by looking at an endoscopic image displayed in the endoscopic image display area 17A. When varices Z are found on the inner surface of the esophagus by the observation, the touch section 2C of the soft main probe 1 is inserted into the instrument guide channel 18A of the insertion section 18B of the fiberscope unit 18. The tip of the touch section 2C of the soft main probe 1 is stuck out into the esophagus from the exit of the instrument guide channel in the end surface so that the contact element 5 is brought into contact with the varix Z (subject H). In the fiberscope unit 18 having a flexible structure, the flexible tube section 18C is so flexibly bent that the tip section 18D freely turns around. This enables the tip section 18D to freely turn to a place to be observed, and the contact element 5 to freely turn to a place to be diagnosed.

When the contact element 5 is in contact with a varix, the frequency counter circuit 15 shown in FIG. 24 measures the frequency of the electromechanical oscillation system. The controller circuit 16 detects a change in the frequency of the electromechanical oscillation system, in which the contact element 5 is in contact with the varix Z, by data measured by the frequency counter circuit 15 to obtain hardness information of the varix Z. Data of an endoscopic image of the inner surface of the esophagus, which are sent from the fiberscope unit 18, and the hardness information of the varix Z obtained by the data measured by the frequency counter circuit 15 are combined in the controller circuit 16. The endoscopic image and hardness information are displayed in the monitor 17, respectively. As the monitor 17 of the aforementioned hardness measuring apparatus for palpation of internal organs (see FIGS. 15 and 16), the monitor 17 has the two endoscopic image display area 17A and hardness information display area 17B. The endoscopic image including the varix Z is displayed in the endoscopic image display area 17A, and the hardness information of the varix Z in the hardness information display area 17B.

A hardness measuring apparatus for palpation of internal organs according to Modification 2 of Embodiment 2, can be used not only for measuring the hardness of an esophagus, but also for measuring the hardness of a biological tissue of a prostate. The contact element 5 of the soft main probe 1 is brought into contact with the prostate (subject H) using a urethroscope. A change in the frequency of the electromechanical oscillation system, in which the contact element 5 is in contact with the prostate, is measured by the frequency counter circuit 15. The hardness of a biological tissue of the prostate can be determined by measuring the change. A result of the hardness measurement is displayed in the hardness information display area 17B of the monitor 17. In the endoscopic image display area 17A, an endoscopic image of the inner surface of the bladder is displayed.

In addition, this hardness measuring apparatus for palpation of internal organs can be used for measuring the hardness of a biological tissue of a bladder. The contact element 5 of the soft main probe 1 is inserted into the inside of a bladder (subject H) using an urethroscope, so that the contact element 5 is brought into contact with the inner surface of the bladder. A change in the frequency of the electromechanical oscillation system, in which the contact element 5 is in contact with the inner surface of the bladder, is measured by the frequency counter circuit 15. The hardness of a biological tissue of the bladder can be determined by measuring the change. A result of the hardness measurement is displayed in the hardness information display area 17B of the monitor 17. In the endoscopic image display area 17A, an endoscopic image of the inner surface of the bladder is displayed. When the hardness of biological tissues of the prostate and bladder is measured by the hardness measuring apparatus for palpation of internal organs according to Embodiment 2, the progress of prostatomegaly can be diagnosed. A hardness measuring apparatus for palpation of internal organs according to Embodiment 2 can be used for measuring the hardness of any biological tissues in a human body, as well as those of a human lung, lever, esophagus, prostate and bladder, and for medically diagnosing the tissues. The obtained diagnosis results are useful for treatment and prophylaxis.

A hardness measuring apparatus for palpation of internal organs having such a structure comprises the soft main probe 1, in which the touch section 2C is formed by a flexible tube, so that the touch section freely turns around. The contact element 5 can be inserted into a cavity via the instrument guide channel 18A of the insertion section 18B of the fiberscope unit 18 having a flexible structure. The fiberscope section 18 has the flexible tube section 18C at the tip of the insertion section 18B. The flexible tube section 18C enables the tip section 18D to freely turn around. The contact element 5 can freely move in the cavity due to the free turning of the tip section 18D. The illumination window 18E and observation window 18F disposed in the end surface of the tip section 18D of the fiberscope unit 18 can freely turn to a pathological part. The contact element 5 can be surely set in contact with the pathological part to measure the hardness of the pathological part. This hardness measuring apparatus for palpation of internal organs easily enables a precise diagnosis of a biological tissue in a cavity.

This hardness measuring apparatus for palpation of internal organs has the soft main probe 1 which can be inserted into a cavity, enabling the hardness of a biological tissue in the cavity to be measured without performing a painful surgical operation on a patient.

This hardness measuring apparatus for palpation of internal organs has the endoscopic image display area 17A and hardness information display area 17B in the monitor 17. The hardness of an affected part of a biological tissue in a cavity, with which the contact element 5 should be in contact, can be measured while identifying the actual position of the affected part by observing an endoscopic image. This enables a safe diagnosis of a biological tissue at the correct position with high efficiency.

[Modification 3]

Figure 27:
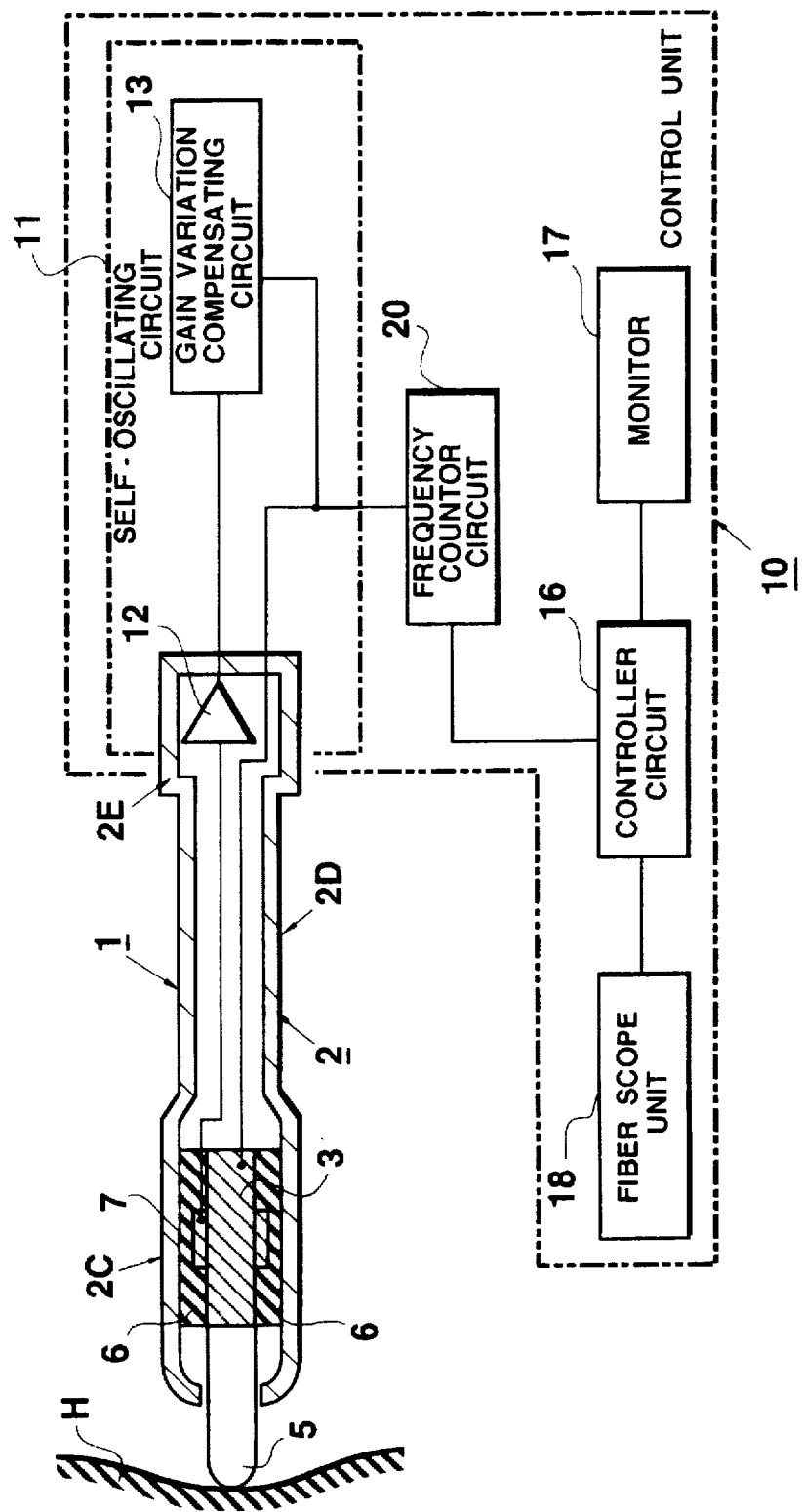
FIG. 27 shows the overall structure of a hardness measuring apparatus for palpation of internal organs according to Modification 3 of Embodiment 2.

A hardness measuring apparatus for palpation of internal organs according to Modification 3 of Embodiment 2 has a structure of the control unit 10 partly different from that in the hardness measuring apparatus for palpation of internal organs according to Embodiment 2. FIG. 27 shows the overall structure of a hardness measuring apparatus for palpation of internal organs according to Modification 3 of Embodiment 2. This hardness measuring apparatus for palpation of internal organs has an amplitude voltage measuring circuit 20 instead of the frequency counter circuit 15. When the contact element 5 of the main probe 1 is brought into contact with a subject H, the resonance frequency and resonance amplitude voltage of the electromechanical oscillation system are changed due to the acoustic impedance of the subject H. The amplitude voltage measuring circuit 20 measures the amplitude voltage of the electromechanical oscillation system.

In FIG. 17 (gain-frequency and admittance-frequency characteristic curves) shown before, the central frequency $f_2$ of the gain variation compensating circuit 13 shown in the gain-frequency characteristic curve 13G is set lower than the central frequency $f_1$ of the electromechanical oscillation system shown in the gain-frequency characteristic curve MG. Therefore, when the contact element 5 is brought into contact with the subject H, the frequency of the electromechanical oscillation system is changed, the gain is increased in response to this change in the frequency, and then the amplitude voltage is increased.

A hardness measuring apparatus for palpation of internal organs having such a structure has advantages similar to those provided by the aforementioned hardness measuring apparatus for palpation of internal organs according to Embodiment 2. The frequency counter circuit 15 in the respective hardness measuring apparatuses for palpation of internal organs according to Modifications 1 and 2 of Embodiment 2 can be replaced with the amplitude voltage measuring circuit 20.

[Modification 4]

Figure 28:
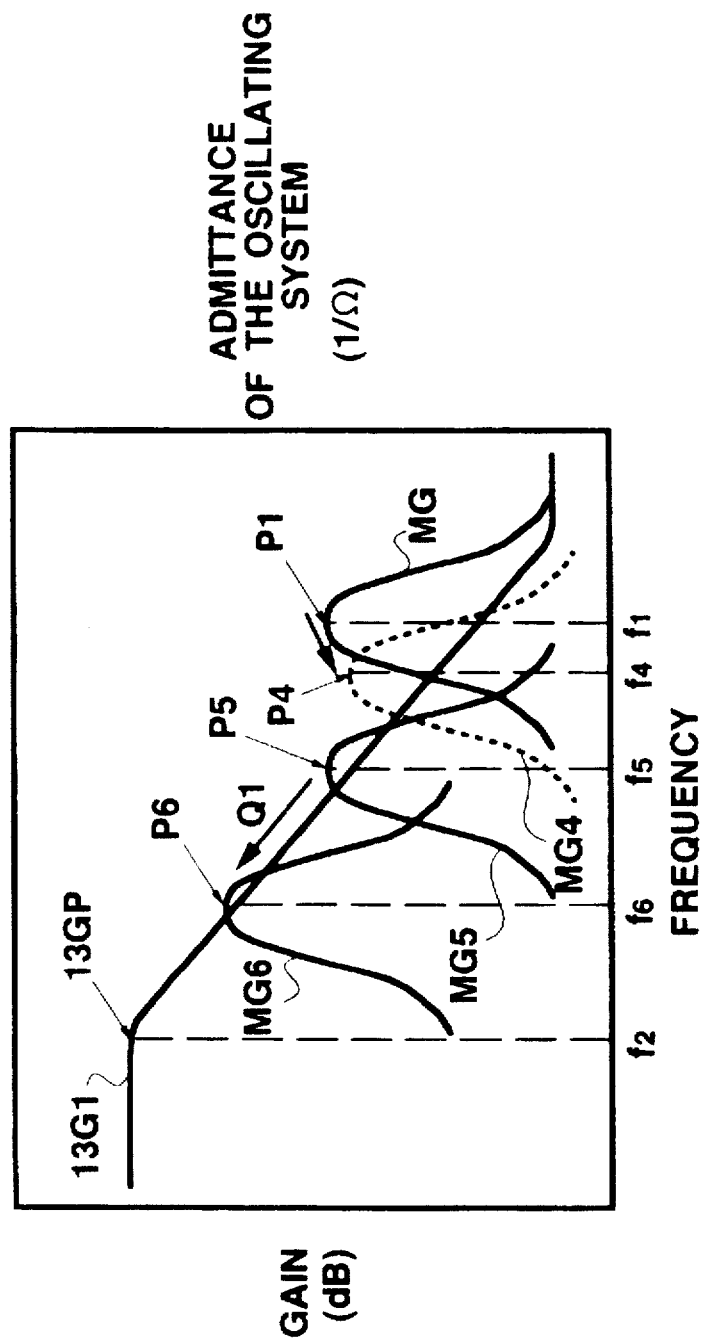
FIG. 28 shows gain-frequency and admittance-frequency characteristic curves of a hardness measuring apparatus for palpation of internal organs according to Modification 4 of Embodiment 2.

In a hardness measuring apparatus for palpation of internal organs according to Modification 4 of Embodiment 2, a low-pass filter circuit is used as the gain variation compensating circuit 13 instead of the band-pass filter circuit. FIG. 28 shows gain-frequency and admittance-frequency characteristic curves of the electromechanical oscillation system and gain variation compensating circuit 13 in a hardness measuring apparatus for palpation of internal organs according to Modification 4 of Embodiment 2. The horizontal axis represents frequency, and the vertical axes respectively represent gain and admittance of the oscillation system. As the gain-frequency and admittance-frequency characteristic curves shown in FIG. 17, the characteristic curve MG shows a gain-frequency characteristic (admittance-frequency characteristic) of the electromechanical oscillation system excepting the gain variation compensating circuit 13, when the contact element 5 is not in contact with a subject H. The characteristic curve 13G1 shows a gain-frequency characteristic of the gain variation compensating circuit 13. In the gain variation compensating circuit 13 of a hardness measuring apparatus for palpation of internal organs according to Modification 4 of Embodiment 2, a low-pass filter circuit is used. The gain-frequency characteristic of the gain variation compensating circuit 13 is set in a frequency band in the gain-frequency characteristic curve 13G1, in which the gain of the electromechanical oscillation system is changed in response to a change in the frequency. A central frequency $f_2$, at which the gain has a maximum value 13GP in the gain-frequency characteristic curve 13G of the gain variation compensating circuit 13, is set lower than a central frequency $f_1$ at which the gain in the characteristic curve MG of the electromechanical oscillation system has a maximum value P1 (maximum value of the admittance). Therefore, the electromechanical oscillation system resonantly oscillates at a frequency lower than the central frequency $f_1$, and higher than the central frequency $f_2$, when the contact element 5 is in contact with subject H.

When the contact element 5 of the main probe 1 (see FIG. 14) is in contact with a biological tissue (subject H), the gain-frequency characteristic curve MG of the electromechanical oscillation system is changed to a gain-frequency characteristic curve MG4 in a conventional hardness measuring apparatus. In this gain-frequency characteristic curve MG4, the resonance frequency given by the maximum value P4 is changed to a frequency $f_4$ because the acoustic impedance of the subject H is low.

A hardness measuring apparatus for palpation of internal organs according to Embodiment 2 shows a gain-frequency characteristic curve MG5 when the contact element 5 of the main probe 1 is not in contact with anything. The gain-frequency characteristic curve MG5 has a maximum value P5 at a central frequency $f_5$. When contacting the contact element 5 with a subject H, the gain-frequency characteristic curve MG5 is changed to a gain-frequency characteristic curve MG6. Because the acoustic impedance of the subject H is low, the central frequency $f_5$ is shifted to a frequency $f_6$. The gain is increased along the gain-frequency characteristic curve 13G1 of the gain variation compensating circuit 13 by the gain increasing and phase transfer functions of the gain variation compensating circuit 13, leading to obtaining a maximum value P5 of the gain. This increased gain enables a sufficient detection voltage for hardness measurement to be obtained.

A hardness measuring apparatus for palpation of internal organs having such a structure has advantages similar to those provided by the aforementioned hardness measuring apparatus for palpation of internal organs according to Embodiment 2.

[Modification 5]

Figure 29:
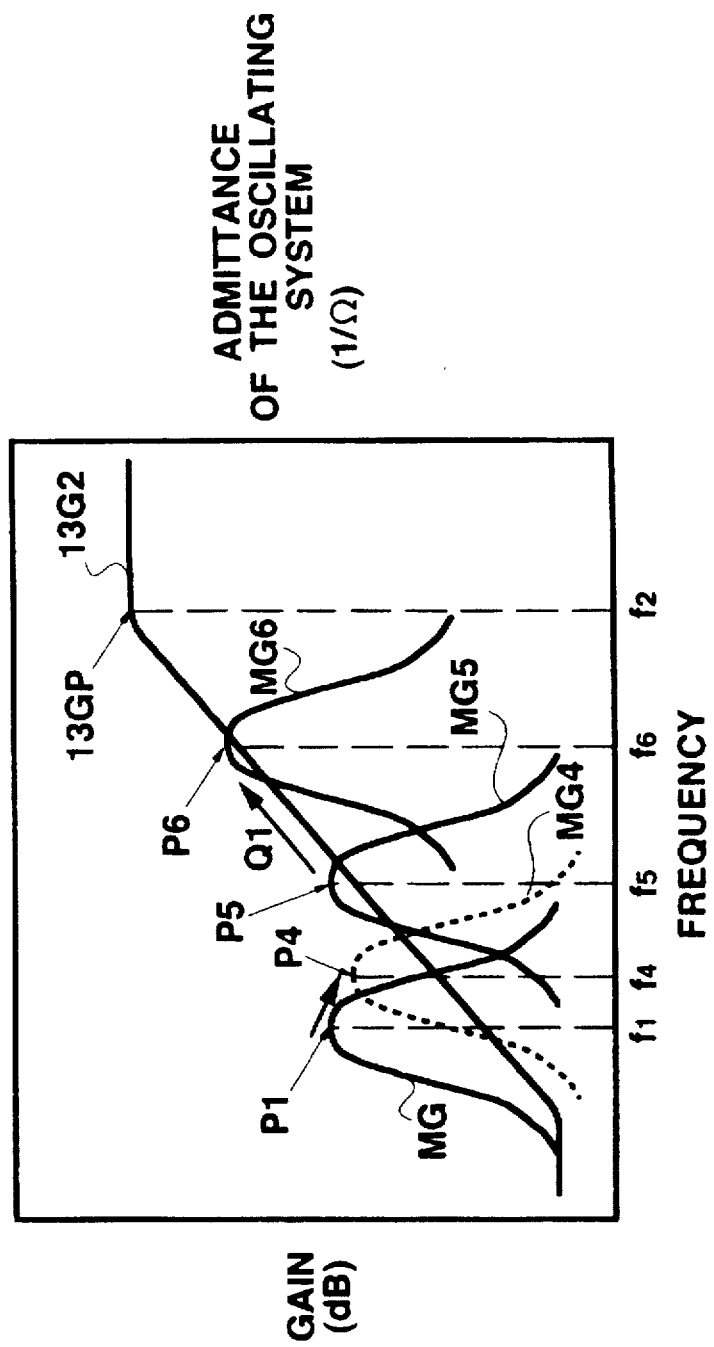
FIG. 29 shows gain-frequency and admittance-frequency characteristic curves of a hardness measuring apparatus for palpation of internal organs according to Modification 5 of Embodiment 2.

In a hardness measuring apparatus for palpation of internal organs according to Modification 5 of Embodiment 2, a high-pass filter circuit is used as the gain variation compensating circuit 13 instead of the band-pass filter circuit. FIG. 29 shows gain-frequency and admittance-frequency characteristic curves of the electromechanical oscillation system and gain variation compensating circuit 13 in a hardness measuring apparatus for palpation of internal organs according to Modification 5 of Embodiment 2. The horizontal axis represents frequency, and the vertical axes respectively represent gain and admittance of the oscillation system. The characteristic curve MG shows a gain-frequency characteristic (admittance-frequency characteristic) of the electromechanical oscillation system excepting the gain variation compensating circuit 13, when the contact element 5 is in contact with a subject H. The characteristic curve 13G2 shows a gain-frequency characteristic of the gain variation compensating circuit 13. In the gain variation compensating circuit 13 of a hardness measuring apparatus for palpation of internal organs according to Modification 5 of Embodiment 2, a high-pass filter circuit is used. The slope of the gain-frequency characteristic curve 13G2 of the gain variation compensating circuit 13 is opposite to that of the gain-frequency characteristic curves 13G and 13G1, which are obtained by using band-pass and low-pass filter circuits, respectively. A central frequency $f_2$, at which the gain has a maximum value 13GP in the gain-frequency characteristic curve 13G2 of the gain variation compensating circuit 13, is set higher than a central frequency $f_1$ at which the gain in the characteristic curve MG of the electromechanical oscillation system has a maximum value P1. Therefore, the electromechanical oscillation system resonantly oscillates at a frequency higher than the central frequency $f_1$, and lower than the central frequency $f_2$, when the contact element 5 is in contact with subject H.

A hardness measuring apparatus for palpation of internal organs is particularly suitable for measuring the hardness of a hard subject H. Therefore, the hardness of a relatively hard biological tissue, such as a human bone, tooth or nail, can be measured by this hardness measuring apparatus for palpation of internal organs. When the contact element 5 of the main probe 1 (see FIG. 14) is in contact with a hard subject H, the gain-frequency characteristic curve MG of the electromechanical oscillation system is changed to a gain-frequency characteristic curve MG4 in a conventional hardness measuring apparatus. In this gain-frequency characteristic curve MG4, the resonance frequency $f_4$ at which the maximum value P4 is given is shifted toward a higher frequency, because the acoustic impedance of the subject H is high.

A hardness measuring apparatus for palpation of internal organs according to Embodiment 2 shows a gain-frequency characteristic curve MG5 when the contact element 5 of the main probe 1 is not in contact with anything. The gain-frequency characteristic curve MG5 has a maximum value P5 at a central frequency $f_5$. When bringing the contact element 5 into contact with a hard subject H, the gain-frequency characteristic curve MG5 is changed to a gain-frequency characteristic curve MG6. Because the acoustic impedance of the subject H is high, the central frequency $f_5$ is shifted to a resonance frequency $f_6$. The gain is increased along the gain-frequency characteristic curve 13G2 of the gain variation compensating circuit 13, leading to the obtaining of a maximum value P5 of the gain. This increased gain enables a sufficient detection voltage for hardness measurement to be obtained. A hardness measuring apparatus for palpation of internal organs having such a structure has advantages similar to those provided by the aforementioned hardness measuring apparatus for palpation of internal organs according to Embodiment 2.

The hardness measuring apparatus for palpation of internal organs can detect a slight change in the hardness of a hard biological tissue in a patient's body. The fiberscope unit 18 (for example, an arthroscope) is inserted into a knee joint. When the contact element 5 of the main probe 1 is brought into contact with periosteum on a synovial membrane in the knee joint, the hardness of the synovial membrane can be measured. A medical diagnosis of the knee joint can be conducted based on a result of this hardness measurement. The hardness of a relatively hard biological tissue, such as a bone, cartilage or synovial membrane, can be easily measured with high accuracy by a hardness measuring apparatus for palpation of internal organs according to Modification 5 of Embodiment 2.

The hardness of a tooth can be measured by this hardness measuring apparatus for palpation of internal organs. The tooth has enamelum and dentinum, whose hardnesses can be measured. Soft teeth easily suffer from dental caries. When results of the measurement of their hardnesses show that the tooth is soft, fluoridization is carried out for the tooth, preventing the tooth from being decayed.

[Modification 6]

Figure 30:
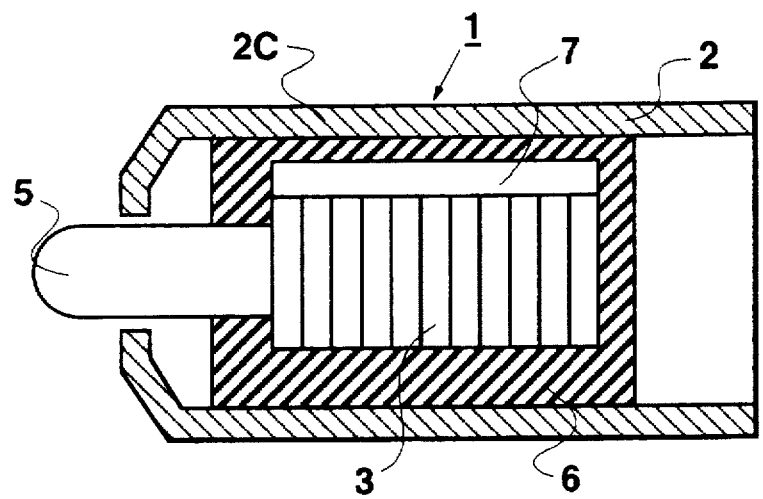
FIG. 30 shows a magnified cross-sectional view of the main part of a main probe of a hardness measuring apparatus for palpation of internal organs according to Modification 6 of Embodiment 2.

A hardness measuring apparatus for palpation of internal organs according to Modification 6 of Embodiment 2 has a structure of the main probe 1, which is partly different from that in a hardness measuring apparatus for palpation of internal organs according to Embodiment 2 shown in FIG. 14. FIG. 30 shows a magnified cross-sectional view of the main part of the main probe 1 of a hardness measuring apparatus for palpation of internal organs according to Modification 6 of Embodiment 2. The main probe 1 of this hardness measuring apparatus for palpation of internal organs has the oscillator 3 comprising a layered piezoelectric ceramic oscillator and the detecting element 7 comprising a bimorph oscillator. The oscillator 3 and detecting element 7 form the electromechanical oscillation system. The layered piezoelectric ceramic oscillator of the oscillator 3 is formed by stacking plural piezoelectric ceramic sheets in the direction of the longitudinal axis of the casing 2. The oscillator 3 is mechanically coupled with the contact element 5. The layered piezoelectric ceramic oscillator has a small size, and outputs a large amplitude for an input voltage.

The detecting element 7 comprising the bimorph oscillator is fixed on the outer surface of the oscillator 3 (layered piezoelectric ceramic oscillator). The detecting element 7 is formed in a film shape. This causes the detecting element 7 to be light in weight, and to require only a small space for its disposition inside the casing 2 of the main probe 1. A film-shaped PVDF-based oscillator can be used as the detecting element 7 instead of the bimorph oscillator.

A hardness measuring apparatus for palpation of internal organs having such a structure has the oscillator 3 comprising a layered piezoelectric ceramic oscillator and the detecting element 7 comprising a bimorph oscillator. Therefore, it has advantages similar to those provided by the aforementioned hardness measuring apparatus for palpation of internal organs according to Embodiment 2. In addition, the size of the oscillator 3 can be reduced since a sufficient amplitude is obtained. The size of the detecting element 7 can be also reduced since the detecting element 7 is formed in a film shape. These enable the size of components inside the main probe 1 to be reduced, realizing a reduced size and weight of the main probe 1 itself. Consequently, the operability of the main probe 1 can be improved, realizing improved operability of the hardness measuring apparatus for palpation of internal organs.

[Modification 7]

Figure 31:
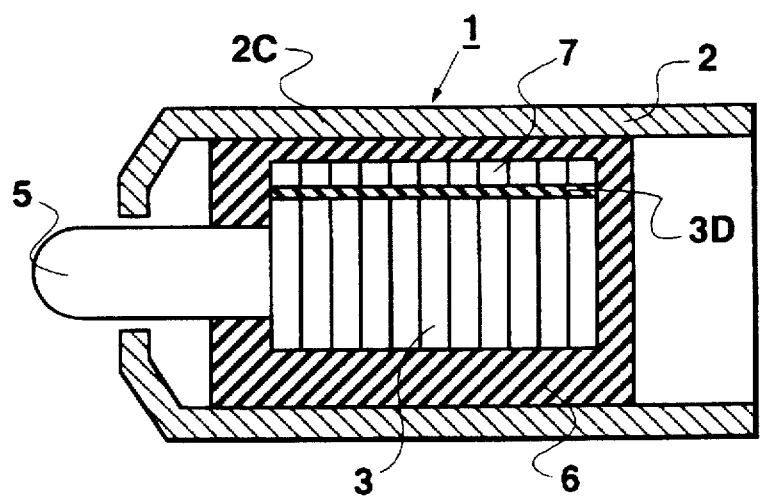
FIG. 31 shows a magnified cross-sectional view of the main part of a main probe of a hardness measuring apparatus for palpation of internal organs according to Modification 7 of Embodiment 2.

A hardness measuring apparatus for palpation of internal organs according to Modification 7 of Embodiment 2 has a structure of the main probe 1, which is partly different from that according to Embodiment 2 shown in FIG. 14. FIG. 31 shows a magnified cross-sectional view of the main part of the main probe 1 of a hardness measuring apparatus for palpation of internal organs according to Modification 7 of Embodiment 2. The main probe 1 of this hardness measuring apparatus for palpation of internal organs has the oscillator 3 comprising a layered piezoelectric ceramic oscillator, the detecting element 7 comprising a layered piezoelectric ceramic oscillator and an insulation material 3D. The oscillator 3 and detecting element 7 form the electromechanical oscillation system. The layered piezoelectric ceramic oscillator of the oscillator 3 is formed by stacking plural piezoelectric ceramic sheets in the direction of the longitudinal axis. This layered piezoelectric ceramic oscillator is small in size, and a large amplitude can be obtained for an input voltage.

The layered piezoelectric ceramic of the detecting element 7 is also formed by stacking plural piezoelectric ceramic sheets in the direction of the longitudinal axis, as that of the oscillator 3. This detecting element 7 is fixed around the oscillator 3.

The insulation material 3D is formed between the oscillator 3 and detecting element 7. The layered piezoelectric ceramic oscillator of the oscillator 3, layered piezoelectric ceramic of the detecting element 7 and insulation material 3D are fabricated as an integrated assembly.

A hardness measuring apparatus for palpation of internal organs having such a structure has both the oscillator 3 and detecting element 7 comprising a layered piezoelectric ceramic oscillator. Therefore, the size of the oscillator 3 can be reduced since a sufficient amplitude is obtained. The size of the detecting element 7 can be also reduced since the detecting element 7 is formed in a film shape. These enable the size of components inside the main probe 1 to be reduced, realizing a reduced size and weight of the main probe 1 itself. Consequently, the operability of the main probe 1 can be improved, realizing improved operability of the hardness measuring apparatus for palpation of internal organs.

[Modification 8]

Figure 32:
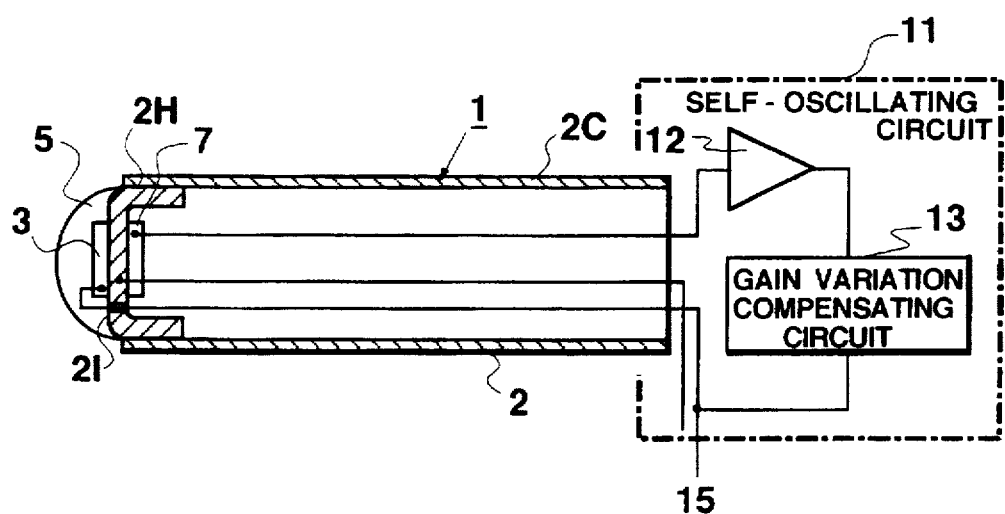
FIG. 32 shows a magnified cross-sectional view of the main part of a soft main probe of a hardness measuring apparatus for palpation of internal organs according to Modification 8 of Embodiment 2.

A hardness measuring apparatus for palpation of internal organs according to Modification 8 of Embodiment 2 has a structure of the soft main probe 1, which is partly different from that according to Embodiment 2 shown in FIGS. 24, 25 and 26. FIG. 32 shows a magnified cross-sectional view of the main part of the soft main probe 1 of a hardness measuring apparatus for palpation of internal organs according to Modification 8 of Embodiment 2. The soft main probe 1 of the hardness measuring apparatus for palpation of internal organs is formed by a soft tube. A supporting member 2H is inserted and fitted into an opening of the soft main probe 1 at the tip facing toward a subject H. The supporting member 2H has a cylindrical shape with a closed end, and is formed by an electroconductive material, such as a metal. The oscillator 3 is fixed to the supporting member 2H on the surface facing to the contact element 5. The detecting element 7 is fixed to the supporting member 2H on the opposite surface facing to the touch section 2C. Both the oscillator 3 and detecting element 7 may comprise a plate-shaped piezoelectric ceramic oscillator. Although details are not shown in FIG. 32, the oscillator has a layer structure in which an electrode (anode), a piezoelectric crystal and an electrode (cathode) are stacked. The detecting element 7 has a similar structure in which an electrode (cathode), a piezoelectric crystal and an electrode (anode) are stacked.

The contact element 5 is mechanically coupled with the oscillator 3 to conduct oscillation generated by the oscillator 3. The contact element 5 has a hemi-spherical shape, and is disposed on the supporting member 2H. This contact element 5 has a function of separating a subject (biological tissue), the oscillator 3 and supporting member 2H. A wiring cable passing aperture 2I for a cable electrically connecting the output terminal (anode) of the oscillator 3 and the output terminal of the gain variation compensating circuit is formed. The supporting member 2H is also used as a common reference potential plate, to which the cathodes of the oscillator 3 and detecting element 7 are electrically connected. The output terminal (anode) of the detecting element 7 is electrically connected to the amplifying circuit 12 of the self-oscillating circuit 11.

A hardness measuring apparatus for palpation of internal organs having such a structure has advantages similar to those provided by the aforementioned hardness measuring apparatus for palpation of internal organs according to Modification 2 of Embodiment 2. In addition, in this hardness measuring apparatus for palpation of internal organs, the supporting member 2H is fixed to an opening at the tip of the touch section 2C of the soft probe 1, enabling the size of the electromechanical oscillation system to be reduced. The flexibility of the tip of the touch section 2C is not adversely affected by the oscillator 3 and detecting element 7. Therefore, the touch section 2C can be smoothly inserted into the instrument guide channel 18A of the fiberscope unit 18 having a soft structure. Consequently, the operability of the soft main probe 1 can be improved, realizing improved operability of the hardness measuring apparatus for palpation of internal organs.

[Modification 9]

Figure 33:
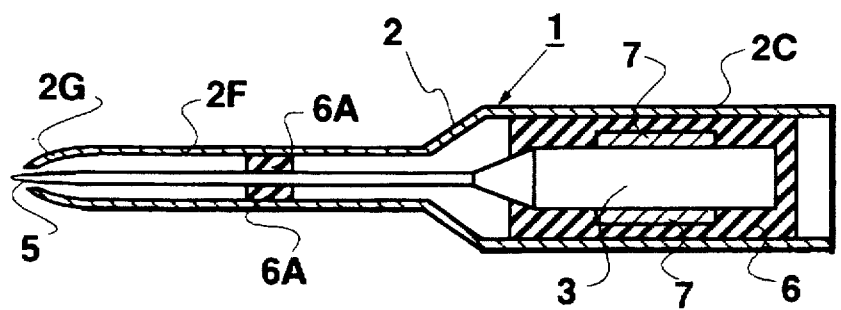
FIG. 33 shows a magnified cross-sectional view of the main part of a main probe of a hardness measuring apparatus for palpation of internal organs according to Modification 9 of Embodiment 2.

A hardness measuring apparatus for palpation of internal organs according to Modification 9 of Embodiment 2 has a structure of the main probe 1, which is partly different from that according to Modification 1 of Embodiment 2 shown in FIGS. 21, 22 and 23. FIG. 33 shows a magnified cross-sectional view of the main part of the main probe 1 of a hardness measuring apparatus for palpation of internal organs according to Modification 9 of Embodiment 2. The main probe 1 of this hardness measuring apparatus for palpation of internal organs has the outer needle 2F in the touch section 2C. The outer diameter of the puncture edge 2G at the tip of the outer needle 2F is gradually decreased toward the tip, making the puncture edge very sharp. The contact element 5 included in the outer needle 2F is stuck out from the opening at the tip of the puncture edge 2G of the outer needle 2F, and is not in contact with puncture edge 2F.

A hardness measuring apparatus for palpation of internal organs having such a structure has advantages similar to those provided by the aforementioned hardness measuring apparatus for palpation of internal organs according to Modification 1 of Embodiment 2. In addition, in this hardness measuring apparatus for palpation of internal organs, the puncture edge 2G having a sharp shape is formed in the outer needle 2F of the main probe 1, realizing smooth puncturing of the outer needle 2F into a biological tissue. The shape of the outer needle 2F including the puncture edge 2G becomes symmetrical. Therefore, the contact of the contact element 5 with the biological tissue is stable, irrespective of puncturing conditions into the biological tissue. In addition, the space between the outer needle 2F and contact element 5 can be made small. This prevents an unnecessary substance, such as a biological tissue, from being put in the space or entering the inside of the outer needle 2F, and then realizes stable hardness measurement.

Embodiment 3

In Embodiment 3 of the present invention, an acceleration measuring, fluid viscosity measuring apparatus and fluid pressure measuring apparatus in which a frequency deviation circuit is used will be described.

[Acceleration Measuring Apparatus]

Figure 34:
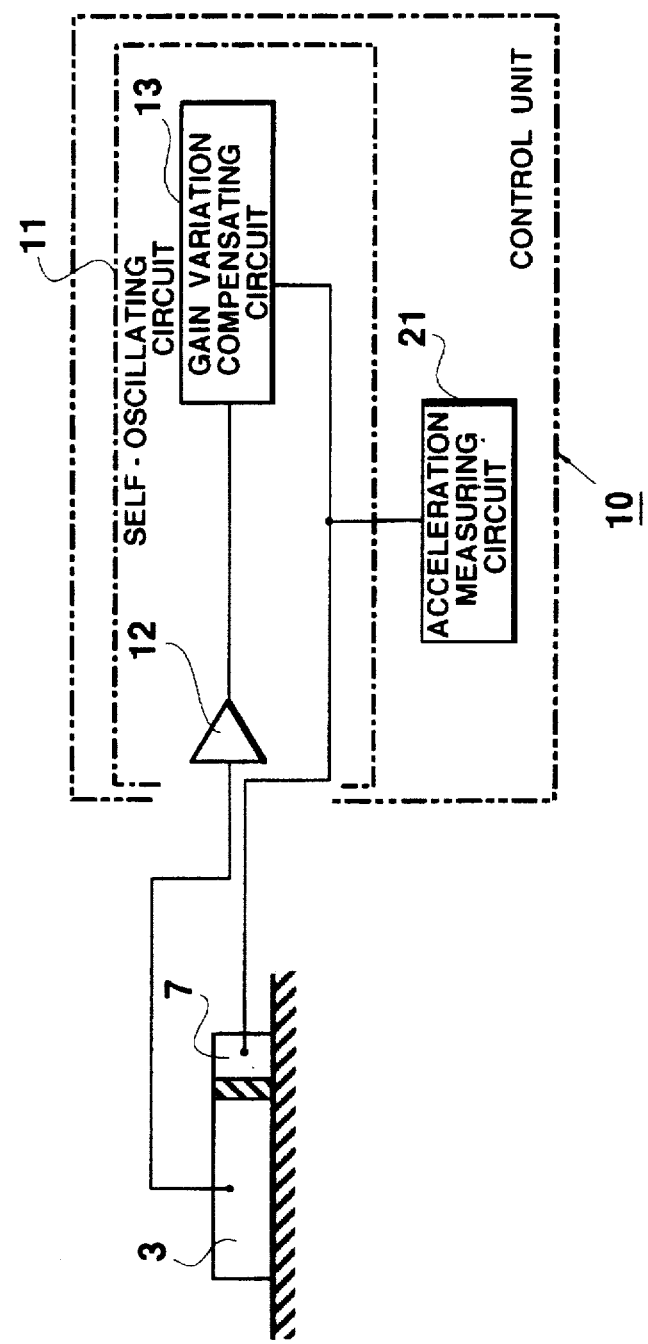
FIG. 34 shows the system structure of an acceleration measuring apparatus according to Embodiment 3 of the present invention.

FIG. 34 shows the system structure of an acceleration measuring apparatus (gyroscope) according to Embodiment 3 of the present invention. The acceleration measuring apparatus basically has a structure similar to that of the aforementioned hardness measuring apparatuses. It has an acceleration measuring section comprising an oscillator 3 and a detecting element 7, and a control unit 10. The oscillator 3 is fixed to a moving body. The oscillation mode in the oscillator 3 is changed by an acceleration (Coriolis force) acting on the moving body. The detecting element 7 detects a change in the oscillation mode of the moving body.

The control unit 10 has a self-oscillating circuit 11 including an amplifying circuit 12, a gain variation compensating circuit 13 and an acceleration measuring circuit 21. The gain variation compensating circuit 13 has a gain increasing function and phase transfer function, and increases the gain in response to a change in the frequency. The acceleration measuring circuit 21 detects a change in the acceleration from the change in the frequency. An acceleration measuring apparatus having such a structure can detect an acceleration acting on a moving body as a change in the oscillation mode of the oscillator 3. A change in the acceleration can be determined by a change in the frequency of an electromechanical oscillation system. In addition, since the gain variation compensating circuit 13 can increase the gain of the electromechanical oscillation system, a sufficient detection voltage for acceleration measurement can be obtained.

[Fluid Viscosity Measuring Apparatus]

Figure 35:
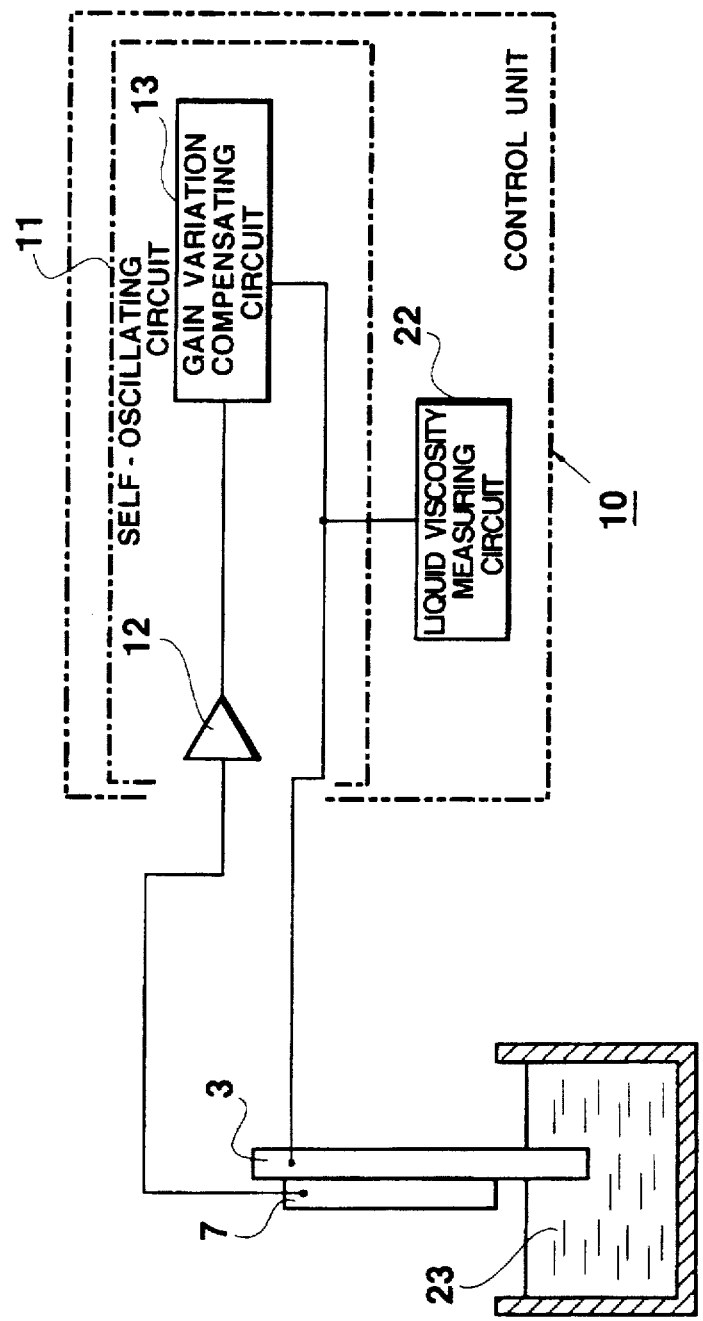
FIG. 35 shows the system structure of a fluid viscosity measuring apparatus according to Embodiment 3 of the present invention.

FIG. 35 shows the system structure of a fluid viscosity measuring apparatus according to Embodiment 3 of the present invention. The fluid viscosity measuring apparatus basically has a structure similar to that of the aforementioned hardness measuring apparatuses. It has a viscosity measuring section comprising an oscillator 3 and a detecting element 7, and a control unit 10. The oscillator 3 is directly in contact with a fluid 23 whose viscosity is to be measured, or indirectly in contact with the fluid 23 via a fluid contact element (not shown in FIG. 35). The oscillation mode in the oscillator 3 is changed by the viscosity of the fluid 23. The detecting element 7 detects a change in the oscillation mode of the moving body.

The control unit 10 has a self-oscillating circuit 11 including an amplifying circuit 12, a gain variation compensating circuit 13 and a fluid viscosity measuring circuit 21. The gain variation compensating circuit 13 has a gain increasing function and phase transfer function, and increases the gain in response to a change in the frequency. The fluid viscosity measuring circuit 21 detects the viscosity of the fluid 23 from the change in the frequency.

In a fluid viscosity measuring apparatus having such a structure, the oscillation mode of the oscillator 3 is changed by the viscosity of a fluid 23. Therefore, the viscosity of the fluid 23 can be determined by a change in the frequency of an electromechanical oscillation system. In addition, since the gain variation compensating circuit 13 can increase the gain of the electromechanical oscillation system, a sufficient detection voltage for acceleration measurement can be obtained.

Figure 36:
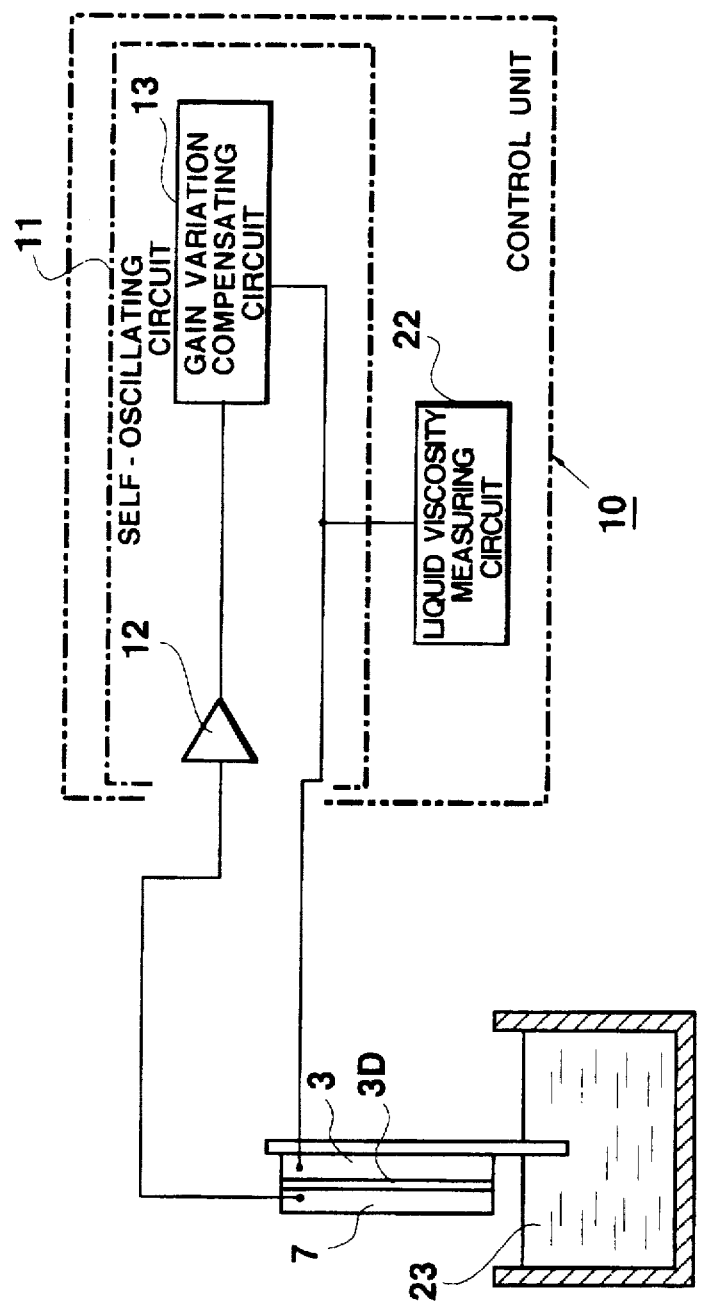
FIG. 36 shows the system structure of a fluid viscosity measuring apparatus according to a modification of Embodiment 3 of the present invention.

FIG. 36 shows the system structure of a fluid viscosity measuring apparatus according to a modification of Embodiment 3. In this fluid viscosity measuring apparatus, the oscillator 3 and detecting element 7 are bimorph oscillators, and an insulation material 3D is disposed between them.

[Fluid Pressure Measuring Apparatus]

Figure 37:
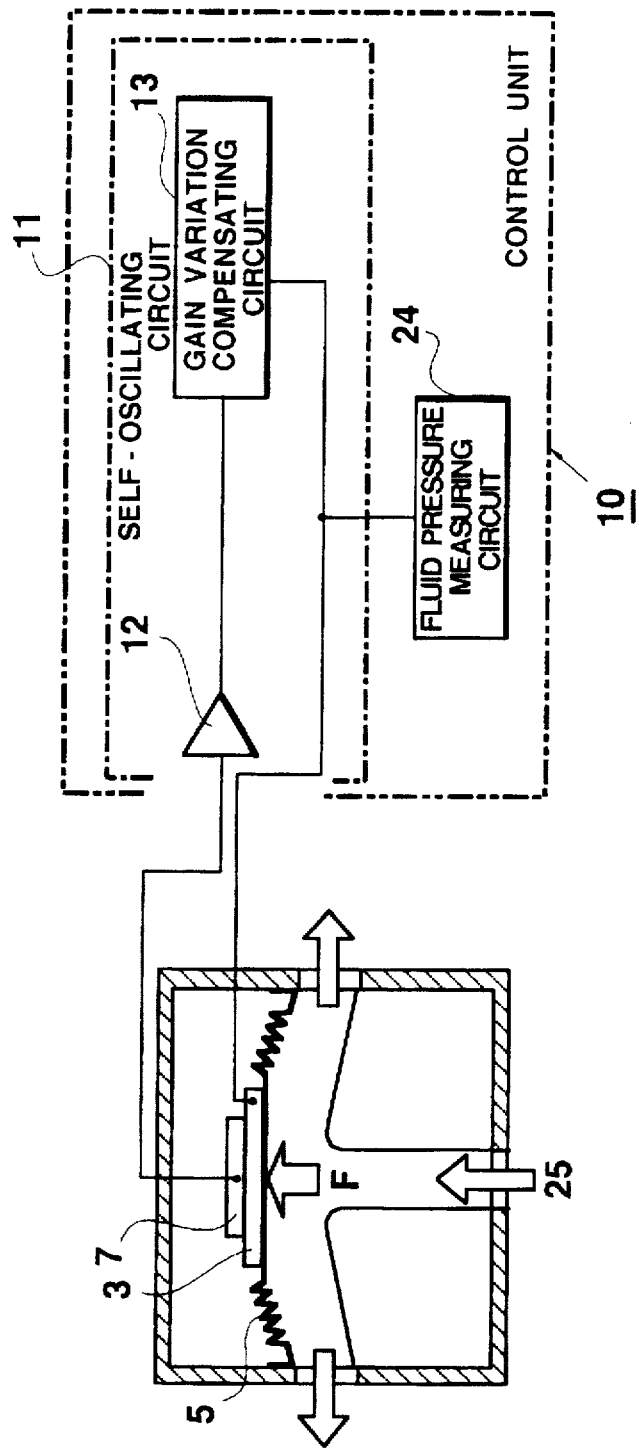
FIG. 37 shows the system structure of a fluid pressure measuring apparatus according to Embodiment 3 of the present invention.

FIG. 37 shows the system structure of a fluid pressure measuring apparatus (pressure sensor) according to Embodiment 3 of the present invention. The fluid pressure measuring apparatus basically has a structure similar to that of the aforementioned hardness measuring apparatuses. It has a fluid pressure measuring section comprising a fluid contact element 5, an oscillator 3 and a detecting element 7, and a control unit 10. The fluid contact element 5 is directly in contact with a fluid 25. The shape of the fluid contact element 5 is changed by a pressure F generated in the fluid 25. A diaphragm or the like is used as the fluid contact element 5. The oscillator 3 is coupled with the fluid contact element 5, and then the position of the oscillator 3 is changed in response to a change in the shape of the fluid contact element 5. As shown in FIG. 37, when a fluid 25 flows upward from the bottom, the fluid contact element 5 is deformed by a pressure F. The position of the oscillator 3 is changed up and down in the vertical direction. The oscillation mode of the oscillator 3 is changed by the change in the position. The detecting element 7 detects a change in the oscillation mode.

The control unit 10 has a self-oscillating circuit 11 including an amplifying circuit 12, a gain variation compensating circuit 13 and a fluid pressure measuring circuit 24. The gain variation compensating circuit 13 has a gain increasing function and phase transfer function, and increases the gain in response to a change in the frequency. The fluid pressure measuring circuit 24 detects a change in the fluid pressure from the change in the frequency.

In a fluid pressure measuring apparatus having such a structure, the position of the oscillator 3 is changed by the pressure F of a fluid 25, and then the oscillation mode of the oscillator 3 is changed. Therefore, a change in the pressure of the fluid 25 can be determined by a change in the frequency of an electromechanical oscillation system. In addition, since the gain variation compensating circuit 13 can increase the gain of the electromechanical oscillation system, a sufficient detection voltage for acceleration measurement can be obtained.

Figure 38:
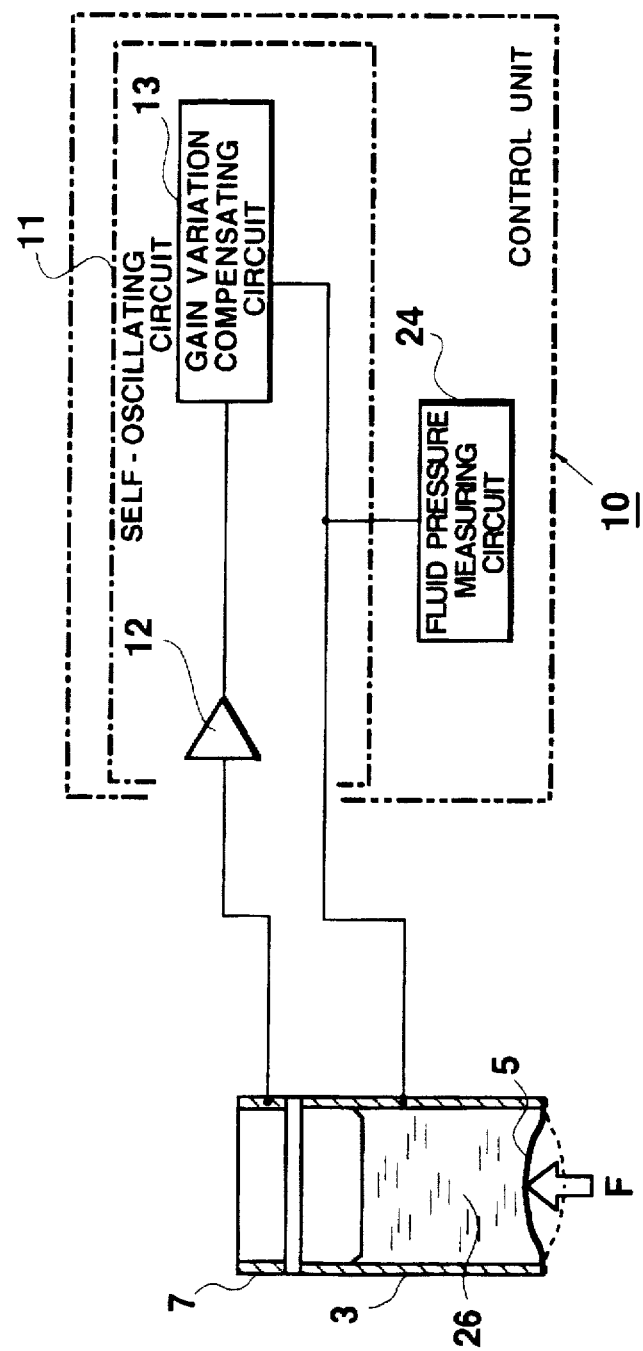
FIG. 38 shows the system structure of a fluid pressure measuring apparatus according to a modification of Embodiment 3 of the present invention.

FIG. 38 shows the system structure of a fluid pressure measuring apparatus according to a modification of Embodiment 3 of the present invention. This fluid pressure measuring apparatus comprises an oscillator 3 having a cylindrical shape. A fluid contact element 5, which is deformed by a fluid pressure F, is disposed at an end of the cylindrical-shaped oscillator 3. A moving body 26 which moves in response to a change in the shape of the fluid contact element 5 is stored in a space formed by the cylindrical-shaped oscillator 3 and fluid contact element 5. A diaphragm or the like is used as the fluid contact element 5. A liquid, such as water or mercury, gas, such as an inert gas, or fine particles, such as sand or powder, is used as the moving body 26.

In a fluid pressure measuring apparatus having such a structure, when a pressure is applied to the fluid contact element, the fluid contact element 5 is deformed 5, and then the moving body 26 stored inside the oscillator 3 moves. The position of the oscillator 3 is relatively changed by the movement of the moving body 26, and then the oscillation mode of the oscillator 3 is changed. As in the aforementioned fluid pressure measuring apparatus, a change in the pressure of the fluid 25 can be determined by a change in the frequency of an electromechanical oscillation system. In addition, since the gain variation compensating circuit 13 can increase the gain of the electromechanical oscillation system, a sufficient detection voltage for acceleration measurement can be obtained.

While there has been described what are at present considered to be preferred embodiments of the present invention, it will be understood that various modifications may be made thereto, and it is intended that the appended claims cover all such modifications as fall within the true spirit and scope of the present invention.

I claim:

1. A frequency deviation detecting circuit comprising:

an oscillator for generating a mechanical oscillation;

a self-oscillating circuit for feeding back oscillation information of the oscillator, and for generating a resonant state in the oscillator, wherein the oscillator and the self-oscillating circuit form an electromechanical oscillation system; and a gain variation compensating circuit which is disposed in the self-oscillating circuit, has a central frequency different from that of the self-oscillating circuit, and increases gain of the self-oscillating circuit in response to a change in frequency of the electromechanical oscillation system;

wherein the effective resonance frequency band of the electromechanical oscillation system is expanded.

2. A frequency deviation detecting circuit according to claim 1, wherein the gain variation compensating circuit comprises means, including a phase transfer function, for adjusting the difference between the input and output phases, called phase difference, of the self-oscillating circuit to zero, and for promoting feedback oscillation, shifting the frequency so that the phase difference becomes zero, and increasing the gain.

3. A hardness measuring apparatus for obtaining hardness information of a subject comprising:

a contact element adapted to contact a subject;

an oscillator for oscillating the contact element;

a self-oscillating circuit which feeds back oscillation information of the oscillator oscillating the contact element in contact with the subject to generate a resonant state in the oscillator, wherein the oscillator and the self-oscillating circuit form an electromechanical oscillation system; and a gain variation compensating circuit which is disposed in the self-oscillating circuit, has a central frequency different from that of the self-oscillating circuit, and increases gain of the self-oscillating circuit in response to a change in frequency of the electromechanical oscillation system;

wherein the effective resonance frequency band of the electromechanical oscillation system is expanded.

4. A hardness measuring apparatus according to claim 3, wherein the hardness of the subject is measured using a change in the frequency of the electromechanical oscillation system.

5. A hardness measuring apparatus according to claim 3, wherein the hardness of the subject is measured using a change in the phase of the electromechanical oscillation system.

6. A hardness measuring apparatus according to claim 3, wherein the gain compensating circuit increases the gain with a decrease in frequency, and the effective resonance frequency band of the electromechanical oscillation system is expanded in a frequency range used for measuring the hardnesses of soft subjects.

7. A hardness measuring apparatus according to claim 3, wherein the oscillator is any one of a piezoelectric ceramic oscillator, layered ceramic oscillator, PVDF-based oscillator, magnetostrictive element, bimorph oscillator, quartz oscillator or surface acoustic wave (SAW) element.

8. A hardness measuring apparatus according to claim 3, wherein the self-oscillating circuit has an amplifying circuit for amplifying the oscillation information of the oscillator.

9. A hardness measuring apparatus according to claim 8, wherein the gain variation compensating circuit is disposed between an output terminal of the oscillator and an input terminal of the amplifying circuit of the self-oscillating circuit, or between an output terminal of the amplifying circuit of the self-oscillating circuit and an input terminal of the oscillator.

10. A hardness measuring apparatus according to claim 3, wherein the gain variation compensating circuit comprises any of a band-pass filter circuit, a low-pass filter circuit, a high-pass filter circuit, a notch filter circuit, an integrating circuit, a differentiating circuit, a peaking amplifying circuit, an active filter circuit or a passive filter circuit.

11. A hardness measuring apparatus according to claim 3, wherein the gain variation compensating circuit comprises means, including a phase transfer function, for adjusting the difference between the input and output phases, called phase difference, of the self-oscillating circuit to zero, and for promoting feedback oscillation, shifting the frequency so that the phase difference becomes zero, and increasing the gain.

12. A hardness measuring apparatus according to claim 3, wherein hardness information of the subject is obtained by using one of a change in the frequency of the electromechanical oscillation system and a change in a phase of the electromechanical oscillation system, and the subject is a biological tissue, and the contact element is adapted to come into contact with the biological tissue when the hardness of the biological tissue is measured.

13. A hardness measuring apparatus according to claim 12, wherein the biological tissue is any of skin, internal organs, body cavities, bones, teeth or nails, and its hardness is measured.

14. A hardness measuring apparatus according to claim 12, further comprising:

a main probe in which the oscillator is contained, and the contact element is fixed; and a monitor for displaying hardness information based on the oscillation information.

15. A hardness measuring apparatus according to claim 14, further comprising:

a fiberscope unit, wherein an observation image obtained by the fiberscope unit is displayed on the monitor.

16. A hardness measuring apparatus according to claim 14, wherein the contact element comprises a contact needle, and an outer needle disposed around the contact needle is placed at the tip portion of the main probe for puncturing a biological tissue.

17. A hardness measuring apparatus according to claim 14, wherein the tip portion of the main probe is formed by a soft tube.

18. A hardness measuring apparatus for obtaining hardness information of a subject comprising:

a contact element in contact with a subject;

an oscillator for oscillating the contact element;

a self-oscillating circuit which feeds back oscillation information of the oscillator oscillating the contact element in contact with the subject to generate a resonant state in the oscillator, wherein the oscillator and the self-oscillating circuit form an electromechanical oscillation system;

a gain variation compensating circuit which is disposed in the self-oscillating circuit, has a central frequency different from that of the self-oscillating circuit, and increases gain in response to a change in frequency of the electromechanical oscillation system; and a frequency measuring circuit for detecting a change in the frequency of the electromechanical oscillation system.

19. A hardness measuring apparatus according to claim 18, further comprising:

a detecting element for detecting the oscillation information of the oscillator, wherein the oscillator comprises a layered piezoelectric ceramic oscillator formed by stacking a plurality of piezoelectric ceramic layers, and the detecting element comprises a film-shaped bimorph oscillator.

20. A hardness measuring apparatus according to claim 18, further comprising:

a detecting element for detecting the oscillation information of the oscillator, wherein both the oscillator and detecting element comprise a layered piezoelectric ceramic oscillator formed by stacking a plurality of piezoelectric ceramic layers.

21. A hardness measuring apparatus according to claim 18, further comprising a detecting element for detecting the oscillation information of the oscillator, wherein both the oscillator and detecting element comprise a film-shaped piezoelectric material.

22. A hardness measuring apparatus for obtaining hardness information of a subject comprising:

a contact element adapted to contact a subject;

an oscillator for oscillating the contact element;

a phase lock loop circuit which feeds back oscillation information of the oscillator oscillating the contact element in contact with the subject to generate a resonant state in the oscillator, wherein the contact element, the oscillator and the phase lock loop circuit form an electromechanical oscillation system; and a gain variation compensating circuit which is disposed in the phase lock loop circuit, has a central frequency different from that of the phase lock loop circuit, and increases gain of the phase lock loop circuit in response to a change in frequency of the electromechanical oscillation system;

wherein the effective resonance frequency band of the electromechanical oscillation system is expanded.

23. An acceleration measuring apparatus for measuring a change in the acceleration of a moving substance comprising:

an oscillator which is placed on the moving substance, and generates a mechanical oscillation;

a self-oscillating circuit which feeds back oscillation information of the oscillator to generate a resonant state in the oscillator, wherein the oscillator and the self-oscillating circuit form an electromechanical oscillation system; and a gain variation compensating circuit which is disposed in the self-oscillating circuit, has a central frequency different from that of the self-oscillating circuit, and increases gain of the self-oscillating circuit in response to a change in frequency of the electromechanical oscillation system;

wherein the effective resonance frequency band of the electromechanical oscillation system is expanded.

24. A fluid viscosity measuring apparatus for measuring a change in the viscosity of a fluid comprising:

any of an oscillator for generating oscillation in a fluid and an oscillator for oscillating a fluid contacting element put in the fluid;

a self-oscillating circuit which feeds back oscillation information of the oscillator to generate a resonant state in the oscillator, wherein the oscillator and the self-oscillating circuit form an electromechanical oscillation system; and a gain variation compensating circuit which is disposed in the self-oscillating circuit, has a central frequency different from that of the self-oscillating circuit, and increases gain of the self-oscillating circuit in response to a change in frequency of the electromechanical oscillation system;

wherein the effective resonance frequency band of the electromechanical oscillation system is expanded.

25. A fluid pressure measuring apparatus for measuring a change in the pressure of a fluid comprising:

a fluid contacting element whose shape is changed in response to the pressure of a fluid;

an oscillator which generates oscillation, and the position of which is moved in response to the change in the pressure of the fluid;

a self-oscillating circuit which feeds back oscillation information of the oscillator to generate a resonant state in the oscillator, wherein the oscillator and the self-oscillating circuit form an electromechanical oscillation system; and a gain variation compensating circuit which is disposed in the self-oscillating circuit, has a central frequency different from that of the self-oscillating circuit, and increases gain of the self-oscillating circuit in response to a change in frequency of the electromechanical oscillation system, wherein the effective resonance frequency band of the electromechanical oscillation system is expanded.

26. A measuring apparatus according to claim 22, wherein the gain variation compensating circuit has a phase transfer function of adjusting the difference between the input and output phases, called phase difference, of the self-oscillating circuit to zero, and of promoting feedback oscillation, shifts the central frequency so that the phase difference becomes zero, and increases the gain.

* * * * *